(12) United States Patent
Caldwell et al.

(10) Patent No.: US 11,305,115 B2
(45) Date of Patent: Apr. 19, 2022

(54) PERCUTANEOUS LEAD PLACEMENT ASSEMBLY

(71) Applicant: Avent, Inc., Alpharetta, GA (US)

(72) Inventors: Ryan Caldwell, Alpharetta, GA (US);
Eric A. Schepis, Alpharetta, GA (US);
Phillip A. Schorr, Alpharetta, GA (US);
Shyamant R. Sastry, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 171 days.

(21) Appl. No.: 16/355,670

(22) Filed: Mar. 15, 2019

(65) Prior Publication Data
US 2019/0282267 A1 Sep. 19, 2019

Related U.S. Application Data

(60) Provisional application No. 62/643,216, filed on Mar. 15, 2018.

(51) Int. Cl.
*A61N 1/36* (2006.01)
*A61N 1/20* (2006.01)
(Continued)

(52) U.S. Cl.
CPC ...... *A61N 1/36021* (2013.01); *A61B 17/3468* (2013.01); *A61N 1/05* (2013.01);
(Continued)

(58) Field of Classification Search
None
See application file for complete search history.

(56) References Cited

U.S. PATENT DOCUMENTS

| 5,344,438 A | 9/1994 | Testerman et al. |
| 5,755,750 A | 5/1998 | Petruska et al. |
| (Continued) |

FOREIGN PATENT DOCUMENTS

| WO | 2006029257 | 3/2006 |
| WO | 2008/106174 | 9/2008 |
| (Continued) |

OTHER PUBLICATIONS

Office Action issued for U.S. Appl. No. 16/355,660, dated Dec. 9, 2020.
(Continued)

*Primary Examiner* — Carl H Layno
*Assistant Examiner* — Manolis Pahakis
(74) *Attorney, Agent, or Firm* — Meunier Carlin & Curfman LLC

(57) ABSTRACT

The exemplified systems and methods facilitate a nerve conduction block at a target nerve using electrical stimulation applied from one or more electrodes located on a percutaneous lead that are placed in parallel, or substantially in parallel, and without direct contact, to a long axis of the peripheral nerve over an overlapping nerve region of greater than about 3 millimeters. The exemplified system and method can be further configured to block nerve condition without eliciting onset activity and co-excitation of non-targeted structures. The exemplified method and system can be performed using conventional percutaneous leads, though an improved percutaneous lead design is disclosed herein. In an aspect, an introducer is disclosed that facilitates accurate and consistent insertion of the percutaneous lead to the specified or intended position relative to the target nerve. In another aspect, a treatment kit comprising the various system components to treat pain is disclosed.

12 Claims, 32 Drawing Sheets

(51) Int. Cl.
*A61N 1/05* (2006.01)
*A61N 1/06* (2006.01)
*A61B 17/34* (2006.01)

(52) U.S. Cl.
CPC ......... *A61N 1/0502* (2013.01); *A61N 1/0553* (2013.01); *A61N 1/06* (2013.01); *A61N 1/20* (2013.01); *A61N 1/36017* (2013.01); *A61N 1/36034* (2017.08); *A61N 1/36057* (2013.01); *A61N 1/0551* (2013.01); *A61N 1/0556* (2013.01); *A61N 1/36071* (2013.01); *A61N 1/36128* (2013.01)

(56) References Cited

U.S. PATENT DOCUMENTS

| | | | |
|---|---|---|---|
| 6,319,241 B1 | 11/2001 | King et al. | |
| 6,602,248 B1* | 8/2003 | Sharps | A61B 18/1402 606/32 |
| 6,981,967 B2 | 1/2006 | Massengale et al. | |
| 7,389,145 B2 | 6/2008 | Kilgore et al. | |
| 7,403,821 B2* | 7/2008 | Haugland | A61N 1/36003 607/49 |
| 8,027,718 B2 | 9/2011 | Spinner et al. | |
| 8,060,208 B2 | 11/2011 | Kilgore et al. | |
| 8,463,383 B2 | 6/2013 | Sakai et al. | |
| 8,612,020 B2 | 12/2013 | Donofrio | |
| 8,644,953 B1 | 2/2014 | Finley et al. | |
| 8,700,177 B2 | 4/2014 | Strother et al. | |
| 8,731,676 B2 | 5/2014 | Fang et al. | |
| 8,751,009 B2 | 6/2014 | Wacnik | |
| 8,774,913 B2* | 7/2014 | Demarais | A61N 1/056 607/3 |
| 8,843,188 B2 | 9/2014 | Kilgore et al. | |
| 8,855,776 B2 | 10/2014 | Lin et al. | |
| 8,965,516 B2 | 2/2015 | Bennett et al. | |
| 8,983,612 B2 | 3/2015 | Fang et al. | |
| 8,983,614 B2 | 3/2015 | Kilgore et al. | |
| 9,008,800 B2 | 4/2015 | Ackermann, Jr. et al. | |
| 9,037,248 B2 | 5/2015 | Durand et al. | |
| 9,119,966 B2 | 9/2015 | Franke et al. | |
| RE45,718 E | 10/2015 | Kilgore et al. | |
| 9,205,258 B2 | 12/2015 | Simon et al. | |
| 9,205,265 B2 | 12/2015 | Franke | |
| 9,248,289 B2 | 2/2016 | Bennett et al. | |
| 9,259,571 B2 | 2/2016 | Straka et al. | |
| 9,259,578 B2 | 2/2016 | Torgerson | |
| 9,295,841 B2 | 3/2016 | Fang et al. | |
| 9,333,356 B2 | 5/2016 | Franke et al. | |
| 9,339,647 B2 | 5/2016 | Strother et al. | |
| 9,358,374 B2 | 6/2016 | Dacey, Jr. et al. | |
| 9,364,661 B2 | 6/2016 | Kilgore et al. | |
| 9,387,322 B2 | 7/2016 | Bhadra et al. | |
| 9,403,014 B2 | 8/2016 | Kilgore et al. | |
| 9,409,020 B2 | 8/2016 | Parker | |
| 9,415,211 B2 | 8/2016 | Bradley et al. | |
| 9,498,621 B2 | 11/2016 | Ackermann et al. | |
| 9,555,245 B2 | 1/2017 | Boggs, II et al. | |
| 9,566,426 B2 | 2/2017 | Simon et al. | |
| 9,636,497 B2 | 5/2017 | Bradley et al. | |
| 9,694,181 B2 | 7/2017 | Bhadra et al. | |
| 9,707,394 B2 | 7/2017 | Bennett et al. | |
| 9,884,192 B2 | 2/2018 | Kilgore et al. | |
| 9,889,291 B2 | 2/2018 | Bhadra et al. | |
| 10,039,917 B2 | 8/2018 | Kilgore et al. | |
| 10,071,241 B2 | 9/2018 | Bhadra et al. | |
| 10,195,434 B2 | 2/2019 | Bhadra et al. | |
| 10,360,511 B2 | 7/2019 | Lujan et al. | |
| 2001/0032001 A1* | 10/2001 | Ricart | A61B 18/1485 607/99 |
| 2002/0120259 A1* | 8/2002 | Lettice | A61B 18/1492 606/32 |
| 2003/0014047 A1* | 1/2003 | Woloszko | A61B 18/1492 606/41 |
| 2003/0100924 A1* | 5/2003 | Foreman | A61N 1/36114 607/9 |
| 2003/0158545 A1* | 8/2003 | Hovda | C07D 491/04 606/32 |
| 2003/0195602 A1 | 10/2003 | Boling | |
| 2005/0177202 A1* | 8/2005 | Classen | A61N 1/40 607/46 |
| 2005/0197678 A1 | 9/2005 | Boveja et al. | |
| 2005/0288730 A1* | 12/2005 | Deem | A61B 18/18 607/42 |
| 2006/0184211 A1* | 8/2006 | Gaunt | A61N 1/05 607/48 |
| 2006/0200121 A1* | 9/2006 | Mowery | A61B 18/1477 606/41 |
| 2007/0191915 A1 | 8/2007 | Strother | |
| 2008/0027505 A1* | 1/2008 | Levin | A61N 1/36071 607/46 |
| 2008/0071321 A1* | 3/2008 | Boggs, II | A61N 1/0524 607/39 |
| 2008/0132962 A1 | 6/2008 | Diubaldi | |
| 2008/0147155 A1 | 6/2008 | Swoyer et al. | |
| 2008/0208287 A1 | 8/2008 | Palermo et al. | |
| 2008/0294221 A1 | 11/2008 | Kilgore | |
| 2009/0149926 A1* | 6/2009 | Dacey, Jr. | A61F 7/00 607/96 |
| 2009/0259279 A1 | 10/2009 | Dobak, III | |
| 2010/0016929 A1* | 1/2010 | Prochazka | A61N 1/36021 607/72 |
| 2010/0152808 A1 | 6/2010 | Boggs, II | |
| 2010/0191311 A1 | 7/2010 | Scheiner et al. | |
| 2010/0274318 A1 | 10/2010 | Walker et al. | |
| 2011/0159748 A1 | 6/2011 | Lim et al. | |
| 2011/0224665 A1* | 9/2011 | Crosby | A61N 1/06 606/33 |
| 2011/0301670 A1* | 12/2011 | Gross | A61N 1/36171 607/62 |
| 2012/0046715 A1 | 2/2012 | Moffitt et al. | |
| 2012/0197372 A1* | 8/2012 | Burgher | A61N 1/0558 607/118 |
| 2012/0277823 A1 | 11/2012 | Gerber et al. | |
| 2012/0290031 A1 | 11/2012 | Bjorling et al. | |
| 2012/0290053 A1 | 11/2012 | Zhang et al. | |
| 2012/0296389 A1 | 11/2012 | Fang et al. | |
| 2012/0330218 A1* | 12/2012 | Bradley | A61N 1/0551 604/20 |
| 2013/0066393 A1 | 3/2013 | Gross et al. | |
| 2013/0110194 A1* | 5/2013 | Wei | A61N 1/36071 607/46 |
| 2013/0116752 A1 | 5/2013 | Parker et al. | |
| 2013/0138193 A1 | 5/2013 | Durand et al. | |
| 2013/0238066 A1* | 9/2013 | Boggs, II | A61N 1/0551 607/116 |
| 2013/0253299 A1* | 9/2013 | Weber | A61B 5/4255 600/377 |
| 2013/0257625 A1 | 10/2013 | Holle | |
| 2013/0261697 A1 | 10/2013 | Parker | |
| 2013/0296966 A1 | 11/2013 | Wongsarnpigoon et al. | |
| 2013/0317303 A1 | 11/2013 | Deshmukh et al. | |
| 2014/0058495 A1 | 2/2014 | Sakai et al. | |
| 2014/0135858 A1* | 5/2014 | Ahmed | A61N 1/36082 607/3 |
| 2014/0148753 A1 | 5/2014 | Leven | |
| 2014/0163660 A1 | 6/2014 | Fang et al. | |
| 2014/0324129 A1 | 10/2014 | Franke et al. | |
| 2014/0343655 A1 | 11/2014 | Rao et al. | |
| 2014/0358191 A1 | 12/2014 | Kilgore et al. | |
| 2015/0012063 A1* | 1/2015 | Chen | A61N 1/0553 607/59 |
| 2015/0100106 A1 | 4/2015 | Shishilla et al. | |
| 2015/0105840 A1* | 4/2015 | Boggs, II | A61N 1/0558 607/46 |
| 2015/0127068 A1* | 5/2015 | Simon | A61N 1/36153 607/60 |
| 2015/0148878 A1* | 5/2015 | Yoo | A61N 1/0456 607/118 |
| 2015/0174397 A1 | 6/2015 | Bhadra et al. | |
| 2015/0182742 A1 | 7/2015 | Ackermann et al. | |

(56) References Cited

U.S. PATENT DOCUMENTS

| | | | |
|---|---|---|---|
| 2015/0238259 A1* | 8/2015 | Albeck | A61N 5/0622 |
| | | | 606/3 |
| 2015/0238764 A1 | 8/2015 | Franke | |
| 2015/0320481 A1 | 11/2015 | Cosman et al. | |
| 2016/0030408 A1 | 2/2016 | Levin | |
| 2016/0128767 A1* | 5/2016 | Azamian | A61B 18/1492 |
| | | | 606/41 |
| 2016/0213927 A1 | 7/2016 | McGee et al. | |
| 2016/0235969 A1 | 8/2016 | Kilgore et al. | |
| 2016/0331976 A1 | 11/2016 | Kilgore et al. | |
| 2016/0339239 A1 | 11/2016 | Yoo et al. | |
| 2016/0339241 A1 | 11/2016 | Hargrove et al. | |
| 2017/0173329 A1 | 6/2017 | Boggs, II et al. | |
| 2017/0197079 A1 | 7/2017 | Illegems et al. | |
| 2017/0209695 A1* | 7/2017 | Solomon | A61B 18/203 |
| 2017/0224989 A1* | 8/2017 | Schepis | A61N 1/0556 |
| 2017/0246453 A1 | 8/2017 | Fang et al. | |
| 2017/0312523 A1 | 11/2017 | Bennett et al. | |
| 2018/0028804 A1 | 2/2018 | Pianca et al. | |
| 2018/0085587 A1 | 3/2018 | Kilgore et al. | |
| 2018/0250506 A1 | 9/2018 | Kilgore et al. | |
| 2018/0256886 A1 | 9/2018 | Bhadra et al. | |
| 2018/0361155 A1 | 12/2018 | Bhadra et al. | |
| 2019/0060640 A1 | 2/2019 | Bhadra et al. | |

FOREIGN PATENT DOCUMENTS

| | | |
|---|---|---|
| WO | 2009/061813 | 5/2009 |
| WO | 2012021583 | 2/2012 |
| WO | 2012/159002 | 11/2012 |
| WO | 2014126718 | 8/2014 |
| WO | 2015/003561 | 1/2015 |
| WO | 2016/039768 | 3/2016 |
| WO | 2016/094728 | 6/2016 |
| WO | 2017/044542 | 3/2017 |
| WO | 2017/066734 | 4/2017 |
| WO | 2018/085611 | 5/2018 |

OTHER PUBLICATIONS

Office Action issued for U.S. Appl. No. 15/501,450, dated Feb. 23, 2021.

Kapural et al.; "Novel 10-kHz High-frequency Therapy (HH10 Therapy) Is Superior to Traditional Low-frequency Spinal Cord Stimulation for the Treatment of Chronic Back and Leg Pain"; Anesthesiology 2015, Dated: 2015; 11 pages.

Finch et al.; "High-Frequency (10 kHz) Electrical Stimulation of Peripheral Nerves for Treating Chronic Pain: A Double-Blind Trial of Presence vs Absence of Stimulation"; Neuromodulation 2018; Dated: 2018; 8 pages.

English translation of Decision of Rejection dated Sep. 3, 2019, in Japanese Application No. 2016-511173, 10 pages.

English translation of First Office Action dated Sep. 2, 2019, in Chinese Application No. 201580052460.1, 24 pages.

Office Action issued for U.S. Appl. No. 16/355,651, dated Aug. 26, 2019.

Office Action issued for U.S. Appl. No. 16/355,673, dated Sep. 11, 2019.

Office Action issued for U.S. Appl. No. 15/501,450, dated Aug. 26, 2019.

Franke, Manfred, et al. "Combined KHFAC+ DC nerve block without onset or reduced nerve conductivity after block." Journal of neural engineering 11.5 (2014): 056012.

Frahm, Ken Steffen, et al. "Nerve fiber activation during peripheral nerve field stimulation: importance of electrode orientation and estimation of area of paresthesia." Neuromodulation: Technology at the Neural Interface 19.3 (2016): 311-318.

International Search Report issued for Application No. PCT/US2019/022626, dated Oct. 23, 2019.

Office Action issued for U.S. Appl. No. 16/355,673, dated Dec. 18, 2019.

Joseph et al., High-Frequency Stimulation Selectively Block Different Types of Fibers in Frog Sciatic Nerve. IFEE Transactions on Neural Systems and Rehabilitaion Eng. 19(5), 2011, 8 pages.

International Search report and Written Opinion issued for PCT/US2015/046482, dated Mar. 22, 2016, 20 pages.

Kilgore, et al., Reversible Nerve Conduction Block Using Kilohertz Frequency Alternating Current. Neuromodulation: Technology at the Neural Interface, 17(3): 242-255 (2013).

Office Action issued for U.S. Appl. No. 15/501,450, dated Feb. 22, 2018.

Office Action issued for U.S. Appl. No. 15/501,450, dated Jul. 2, 2018.

Office Action issued for U.S. Appl. No. 15/501,450, dated Mar. 14, 2019.

Office Action issued for U.S. Appl. No. 16/355,660, dated Apr. 19, 2021.

Office Action issued for U.S. Appl. No. 16/355,660, dated Nov. 1, 2021.

M.H. Lev, et al., CT Angiography and CT Perfusion Imaging. Brain Mapping: The Methods (2nd Ed.) 2002, 427-484.

Office Action issued for U.S. Appl. No. 15/501,450, dated Aug. 27, 2021.

* cited by examiner

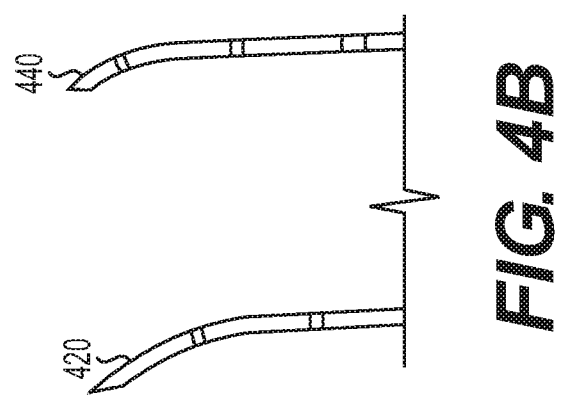

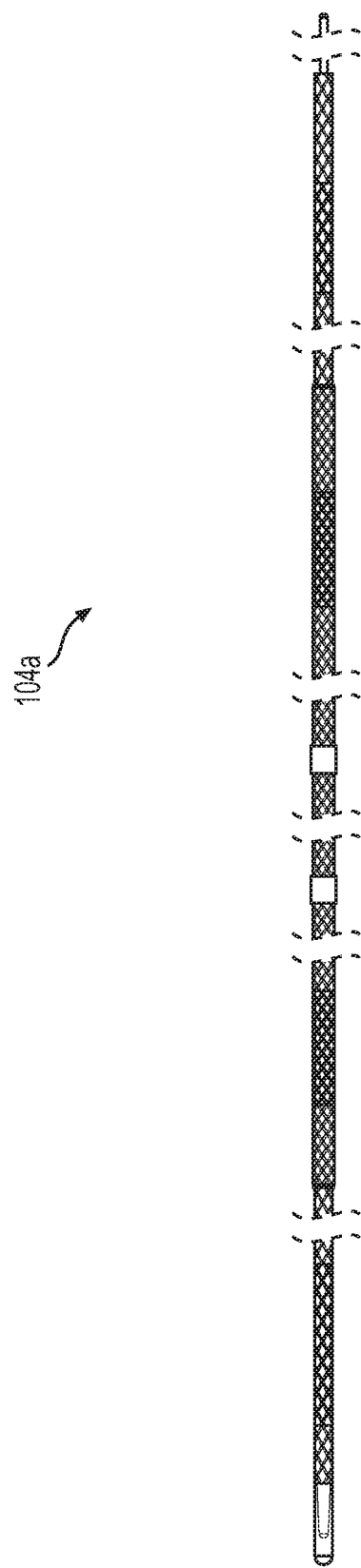

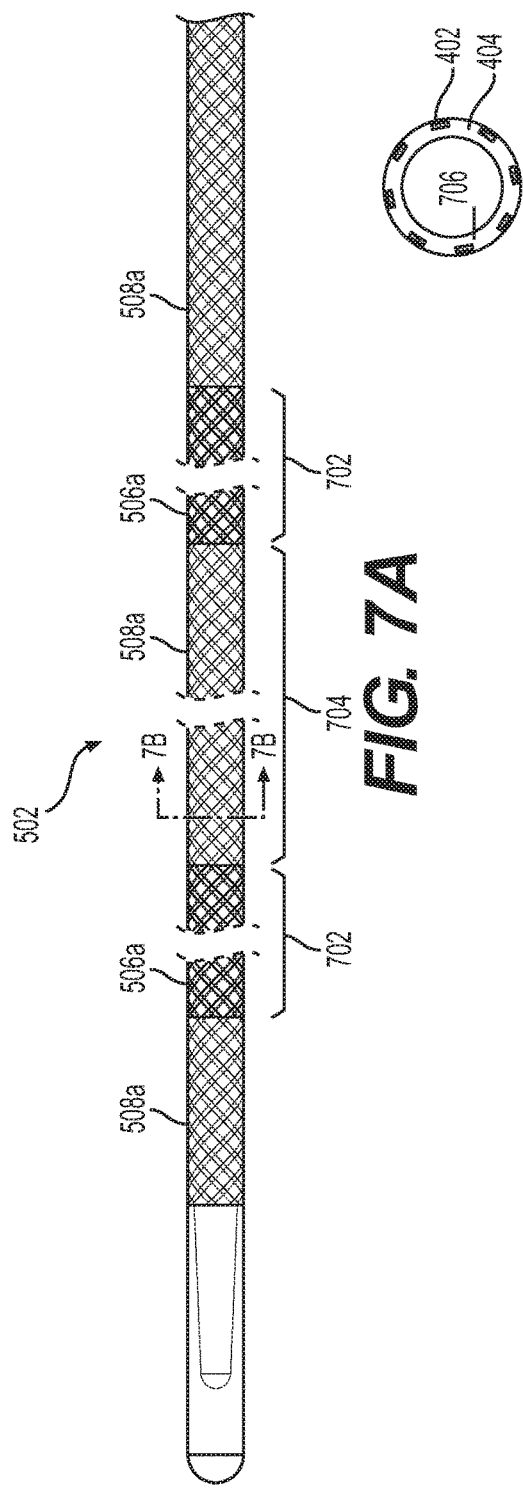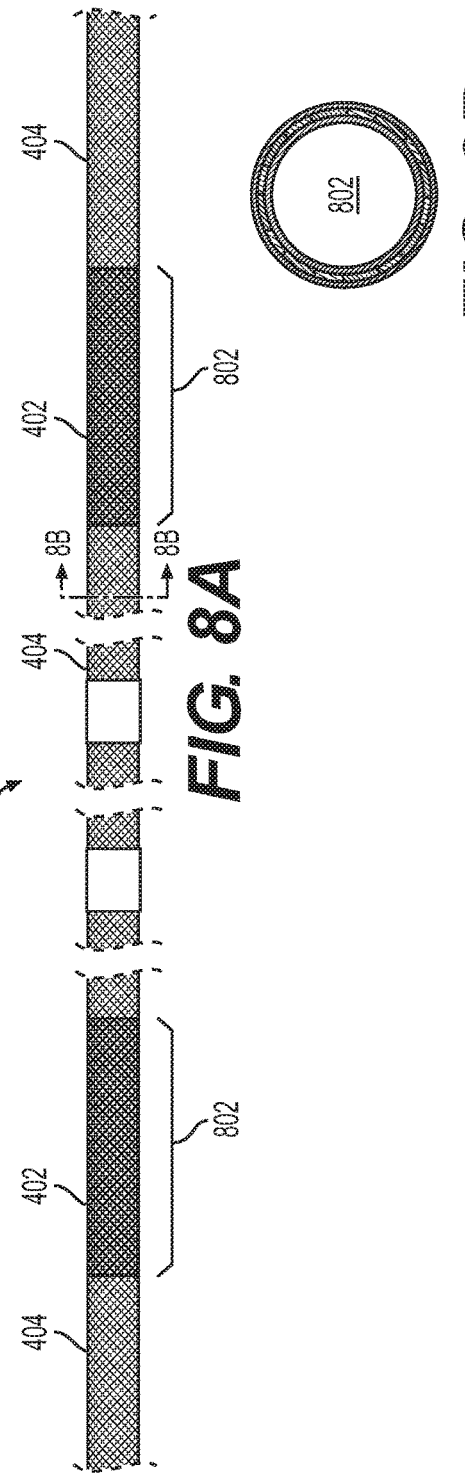

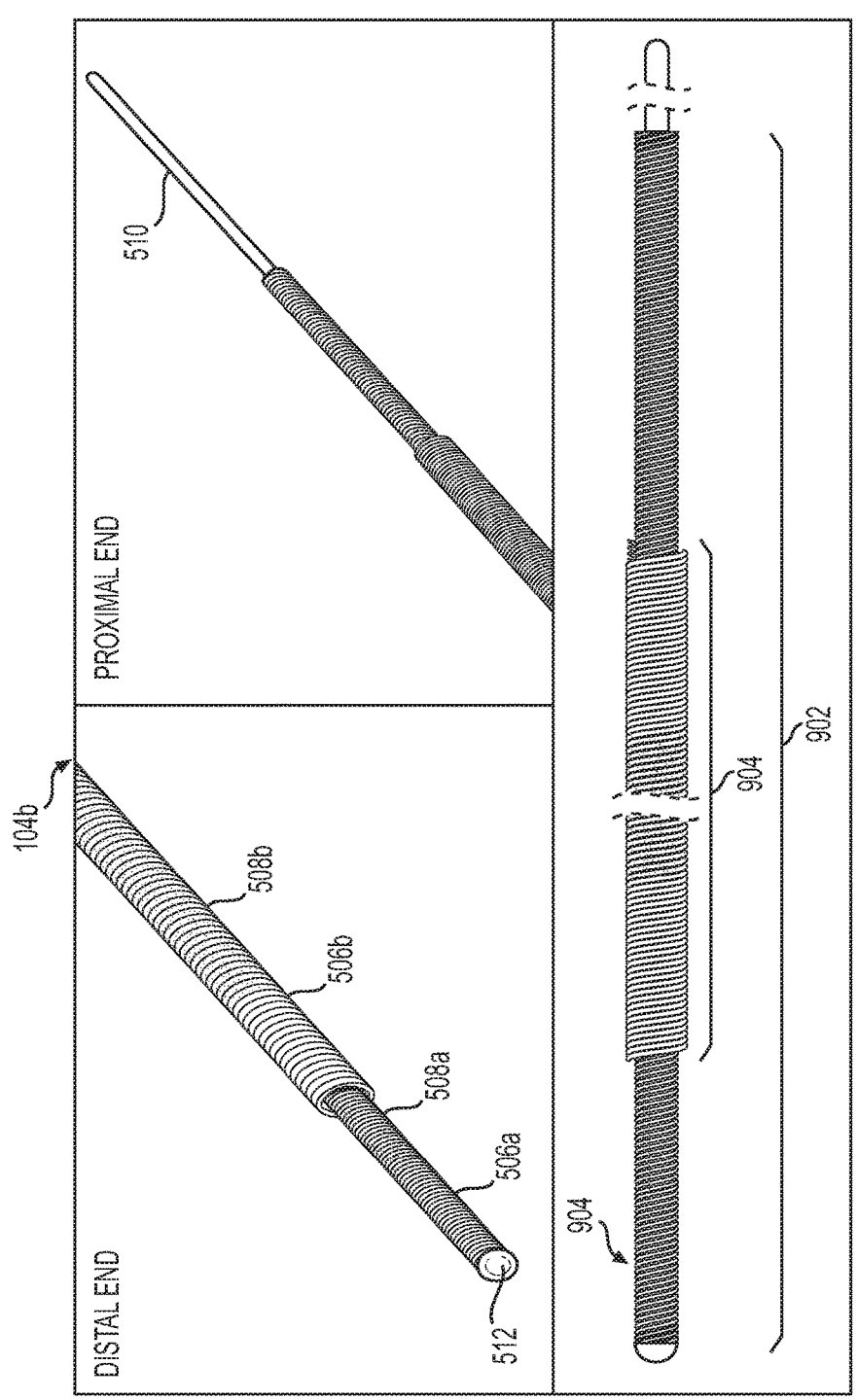
FIG. 9
FIG. 10

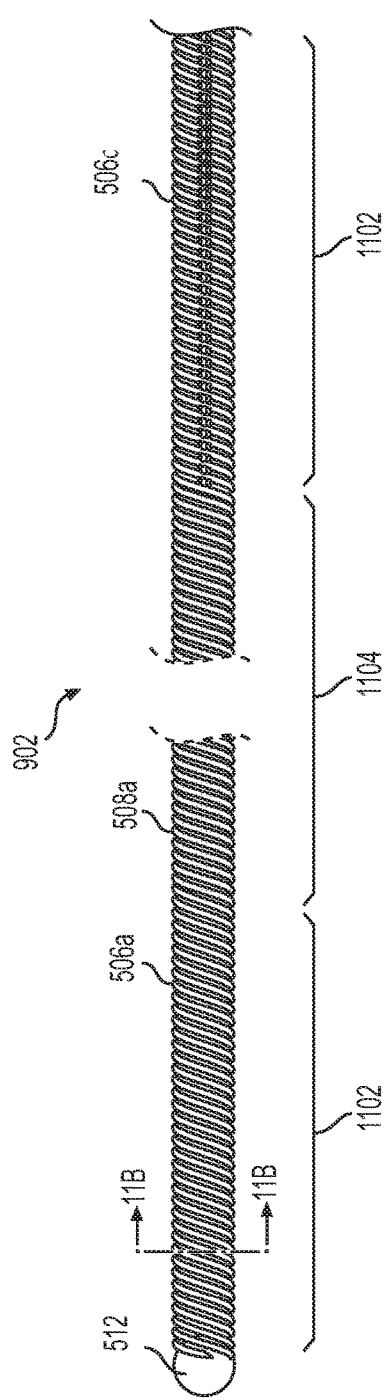
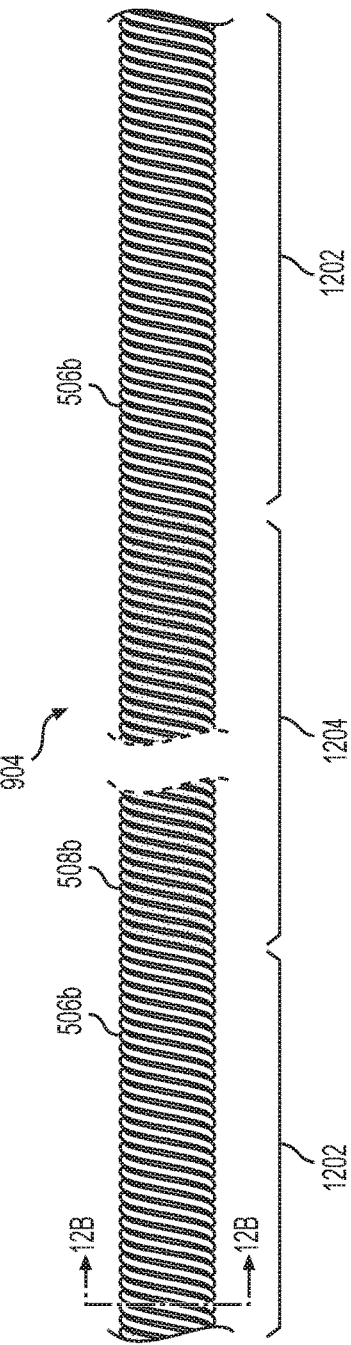
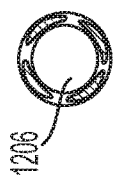
FIG. 11A
FIG. 11B
FIG. 12A
FIG. 12B

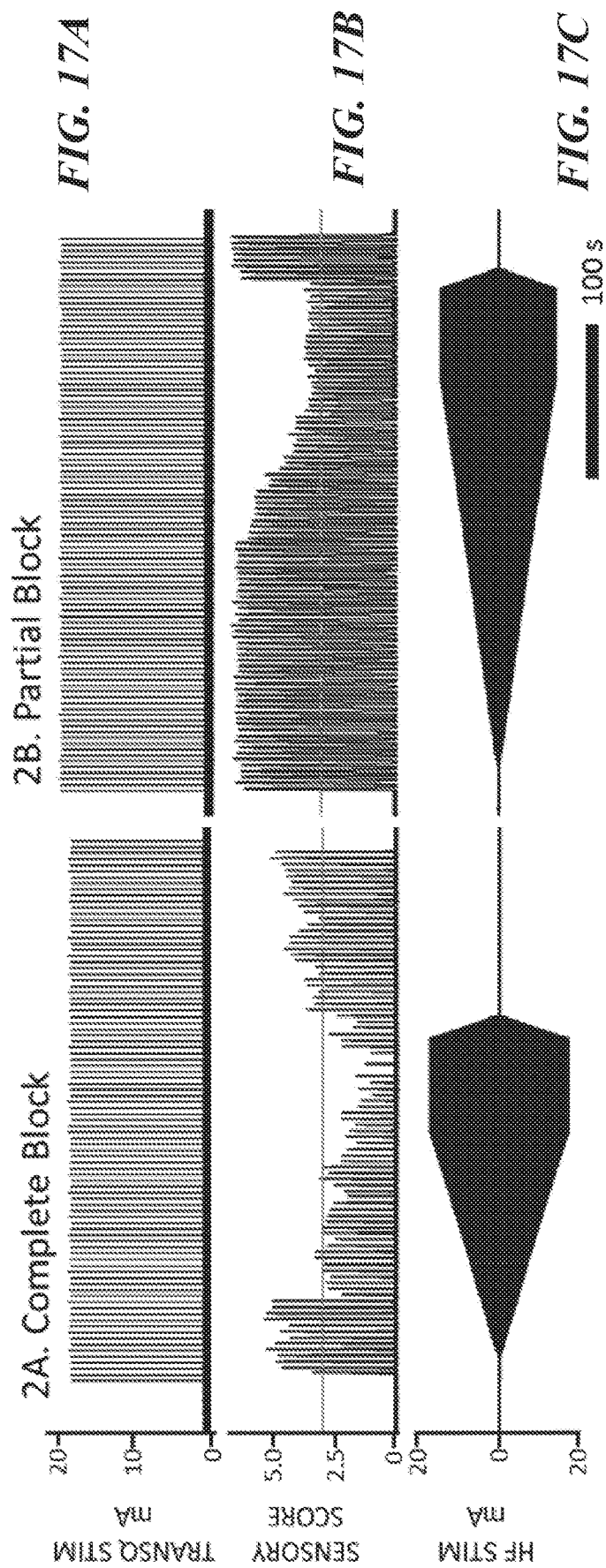

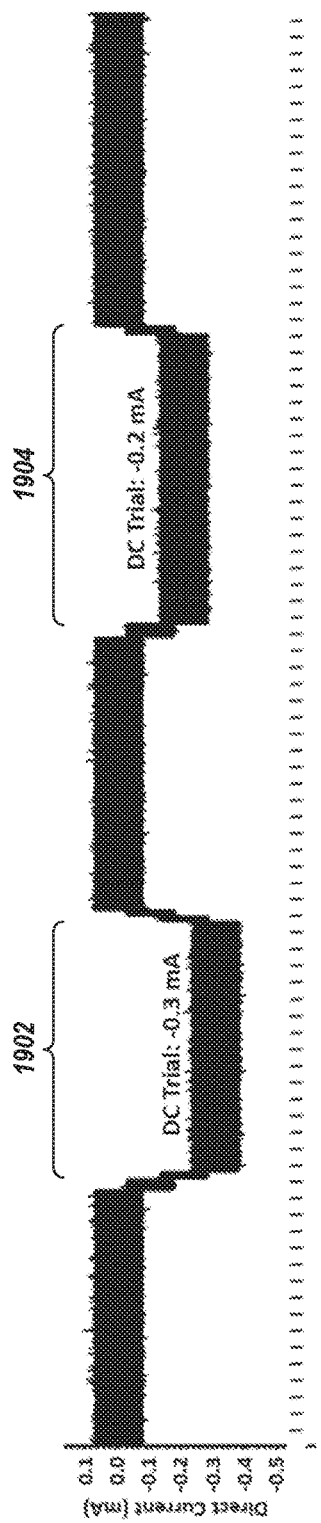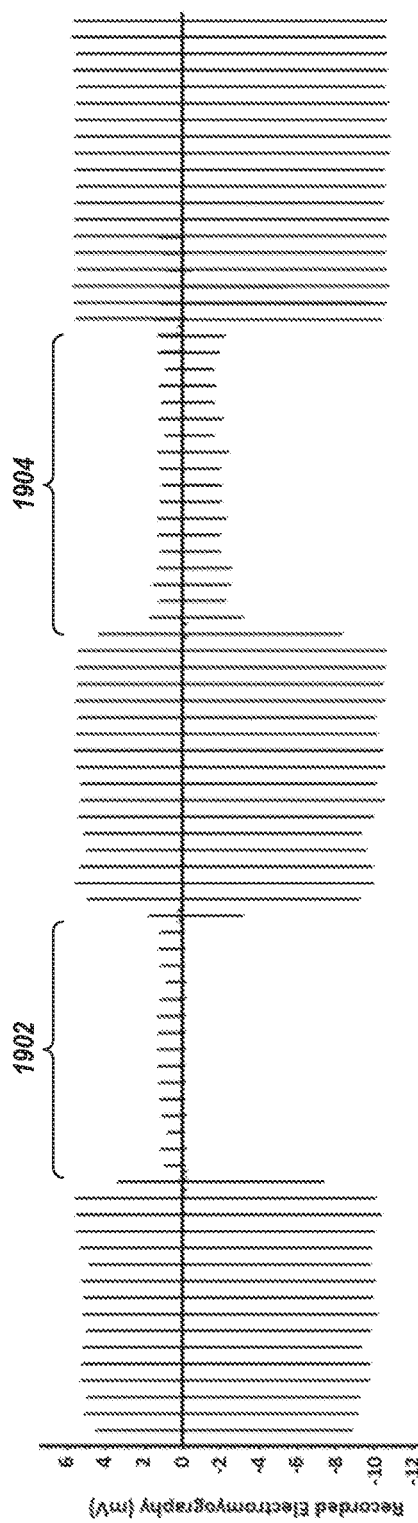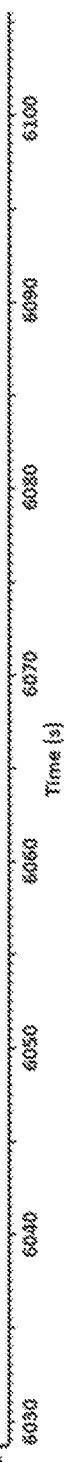
FIG. 18A
FIG. 18B
FIG. 19A   FIG. 19B   FIG. 19C   FIG. 19D   FIG. 19E

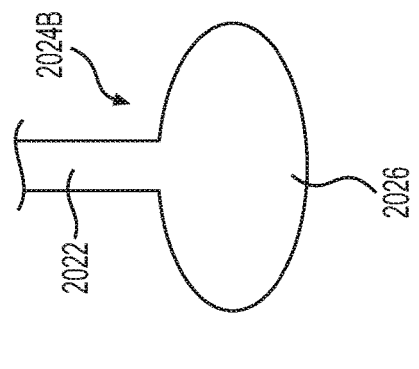
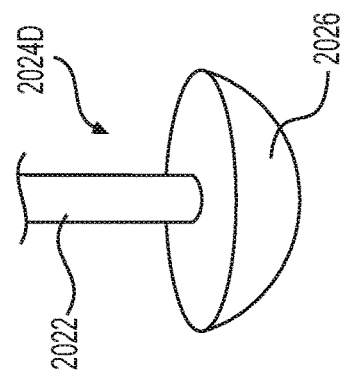
FIG. 23B
FIG. 23D
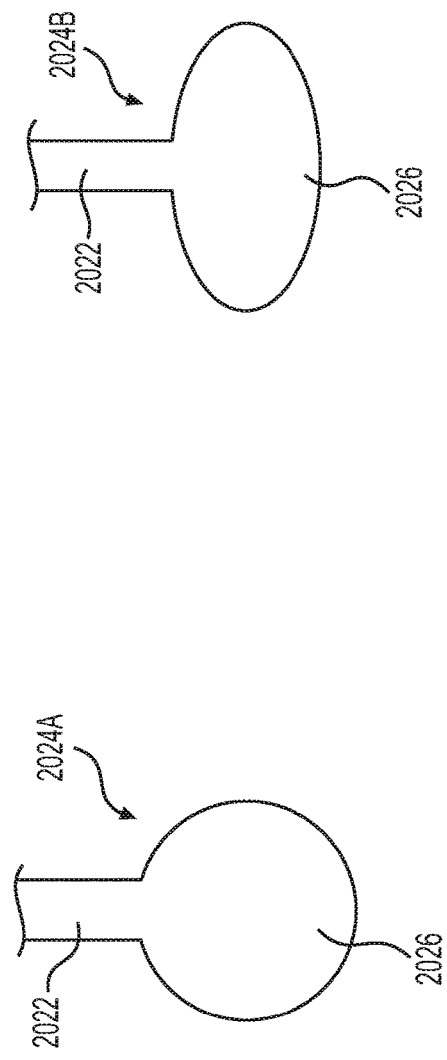
FIG. 23A
FIG. 23C

PERCUTANEOUS LEAD PLACEMENT ASSEMBLY

RELATED APPLICATION

This application claims priority to, and the benefit of, U.S. Provisional Application No. 62/643,216, filed Mar. 15, 2018, titled "System and Method to Percutaneously Block Painful Sensations Elicited by a Peripheral Nerve Without Eliciting Non-Targeted Motor and Sensor Activity," which is incorporated by referenced herein in its entirety.

FIELD OF THE INVENTION

The disclosure relates generally to a system and method to block nerve fiber activity, e.g., to treat pain, particularly, to block peripheral nerve activity through electrical stimulation of a lead, e.g., a percutaneous lead.

BACKGROUND OF THE INVENTION

Pain can be treated by destructive and non-destructive methods that interfere with the transmission of pain signals sent to the brain. Destructive methods, such as radiofrequency ablation, are treatments of last resort, and are typically not used for treating acute (i.e., post-surgical) pain. Non-destructive methods to treat pain include the use of local anesthetic injections and electrical stimulation.

Two types of electrical stimulation have been used to treat pain originating from the periphery: (1) conventional stimulation, and (2) high-frequency stimulation. Conventional electrical stimulation (stimulation at less than 1 KHz) of a peripheral nerve has been used to treat chronic pain and generally involves attenuating or reducing perception of the pain by eliciting a sensory paresthesia within the receptive field of the treated nerve. One type of high-frequency stimulation treatment delivers electrical stimulation (e.g., to the spine) that is below the subsensory threshold to attenuate the pain without causing paresthesia. Such high-frequency and conventional electrical stimulation treatment do not fully block nerve conduction as a means to treat pain. Another type of high-frequency stimulation has been used to treat post-amputation pain in people but requires open surgical procedures to place an electrode in direct physical contact with a target nerve. Further, the usability of high-frequency electrical stimulation is challenged by "onset activity" and the "co-excitation" of nearby excitable tissues.

Onset activity refers to a short (milliseconds-to-seconds duration) burst of action potentials that are elicited at the onset of a high-frequency electrical stimulation. It has been suggested that the onset activity is inherent to the mechanisms responsible for the block effect: each nerve fiber must be depolarized at least once before it can be blocked. Onset response elicited in a peripheral nerve may lead to uncomfortable sensations (i.e., pain), or uncomfortable motor contractions. Animal studies have demonstrated motor onset activity with subsequent muscle contractions. Different strategies have been employed to diminish the onset activity, including increasing the stimulation amplitude and/or increasing the stimulation frequency to greater than 20 kHz, combining other types of nerve blocks such as cooling or direct current stimulation, and adjusting the stimulation electrode configuration. However, the investigated techniques have been either impractical for clinical implementation or have not eliminated the onset response to high frequency electrical stimulation. It has been reported that slowly ramping the amplitude of a high frequency stimulation from zero to block threshold amplitude will enhance the onset response. Kilgore, et al., "Reversible Nerve Conduction Block Using Kilohertz Frequency Alternating Current," *Neuromodulation: Technology at the Neural Interface* (2013).

When high-frequency electrical stimulation is delivered in a percutaneous fashion, it is also challenged by a phenomenon described herein as "co-excitation." That is, regions within close proximity of the stimulating electrodes may effectively receive stimulation amplitude and frequency ample for blocking, whereas the more distal regions may not. As a result, the targeted nerve which is in close proximity to electrode may be blocked, but the more distant excitable tissues (i.e., muscles, blood vessels) may be activated, potentially causing motor contraction and/or vasospasm. Animal studies have consistently shown co-excitation of surrounding muscles and blood vessel following percutaneous high-frequency electrical nerve stimulation.

There is a benefit to having methodologies and electrical stimulation delivery systems that can treat pain by blocking nerve conduction and that does not involve open surgical procedures.

SUMMARY OF THE INVENTION

The exemplified systems and methods facilitate a nerve conduction block at a target nerve (e.g., peripheral nerve) using electrical stimulation applied from one or more electrodes located on a percutaneous lead that are placed in parallel, or substantially in parallel, and without direct contact, to a long axis of the peripheral nerve over an overlapping nerve region of greater than about 3 millimeters. The complete block of nerve conduction also ensures that the patient does not feel any pain or discomfort. Further, without having to directly contact the target nerve, the exemplified system and method provides a large delivery window for the percutaneous electrode to be placed without requiring an open surgical procedure. It is observed that the exemplary method completely and consistently blocks nerve conduction through the overlapping nerve region, thereby arresting any conduction, e.g., of pain sensation from regions of the body downstream of the overlapping nerve region. Indeed, the percutaneous electrode when deployed in such orientation can facilitate complete, or near complete, block of nerve conduction. The exemplified system and method can be further configured to block nerve condition without eliciting onset activity and co-excitation of non-targeted structures.

The exemplified method and corresponding system can employ direct current stimulation or high-frequency stimulation. Indeed, the exemplified method and system provides an eloquent solution to manage and treat pain via electrical stimulation.

The exemplified method and system can be performed using conventional percutaneous leads, though several improved percutaneous lead designs are disclosed herein having features that can facilitate many improvements—e.g., improve block efficacy, improve reliability of treatment, improve titratability, improve reduced onset response and/or co-excitation, and/or improved insertion and retention of the percutaneous lead for longer treatment periods, e.g., up to greater than 6 weeks. Percutaneous leads can be more readily positioned at the specified or intended position relative to the target nerve without need to complex paddle lead structures.

In an aspect, an introducer is disclosed that facilitates accurate and consistent insertion of the percutaneous lead to the specified or intended position relative to the target nerve. In another aspect, a treatment kit comprising the various system components to treat pain is disclosed.

In an aspect, a method is disclosed to percutaneously block nerve conduction (e.g., to inhibit a subject's perception of pain). The method includes delivering electrical stimulation to one or more exposed conductive regions of a lead (e.g., a percutaneous lead) defining one or more electrodes, wherein the one or more electrodes are placed at a treatment site of a subject to block nerve conduction at the treatment site via the electrical stimulation (e.g., high frequency stimulation having frequency between about 2 kHz and 100 kHz or direct current (DC) stimulation), and wherein the one or more electrodes are placed in parallel, or substantially in parallel (e.g., to put an electrode of the lead in parallel, or substantially parallel) to a long axis of a peripheral nerve over an overlapping nerve region (e.g., a collective overlapping nerve region) of greater than about 3 millimeters (e.g., from about 3 millimeters to about 10 centimeters) (e.g., wherein an electrical field generated by the high-frequency electrical stimulation at the overlapping nerve region sufficiently block nerve conduction through the overlapping nerve region).

In some embodiments, an electrical field generated between an electrode of the one or more electrodes and the overlapping nerve region from the application of the electrical stimulation sufficiently blocks nerve conduction through the overlapping nerve region.

In some embodiments, the method further includes surgically placing the lead into the treatment site in an orientation parallel, or substantially parallel, to the long axis of the peripheral nerve.

In some embodiments, the method further includes interventionally placing the lead into the treatment site in an orientation parallel, or substantially parallel, to the long axis of the peripheral nerve.

In some embodiments, the placement of the one or more electrodes places a long axis of the lead (e.g., percutaneous lead) in parallel, or substantially in parallel, to the long axis of the peripheral nerve.

In some embodiments, the one or more electrodes are placed in parallel, or substantially in parallel to, the overlapping nerve region over a distance selected from the group consisting of greater than about 4 millimeters (mm), greater than about 5 mm, greater than about 6 mm, greater than about 7 mm, greater than about 8 mm, greater than about 9 mm, greater than about 1 centimeter (cm), greater than about 2 cm, greater than about 2.5 cm, greater than about 3 cm, greater than about 3.5 cm, greater than about 4 cm, greater than about 4.5 cm, greater than about 5 cm, greater than about 5.5 cm, greater than about 6 cm, greater than about 6.5 cm, greater than about 7 cm, greater than about 7.5 cm, greater than about 8 cm, greater than about 8.5 cm, greater than about 9 cm, greater than about 9.5 cm, and up to about 10 cm.

In some embodiments, the electrical stimulation is predominantly a sinusoidal waveform.

In some embodiments, the electrical stimulation comprises high-frequency stimulation having one or more primary frequency harmonics between about 2 KHz and about 100 KHz. In some embodiments, the high-frequency electrical stimulation is predominantly a sinusoidal waveform, a square waveform, a triangular waveform, a sinc waveform, a noisy waveform (e.g., an unstructured waveform having a pre-defined frequency distribution), or a chirp waveform. In some embodiments, the electrical stimulation is predominantly charged balanced. In some embodiments, the electrical stimulation is charged unbalanced.

In some embodiments, the electrical stimulation comprises direct current stimulation.

In some embodiments, the one or more exposed conductive regions of the lead comprise a cathode region and a return anodic region, and wherein the cathode region and return anodic region collectively form a multi-polar electrode (e.g., bipolar, tripolar, etc., electrode).

In some embodiments, the one or more exposed conductive regions of the lead are configured as a monopolar electrode (e.g., with a return electrode placed at the surface of the skin).

In some embodiments, the one or more exposed conductive regions of the lead comprise a first exposed conductive region and a second exposed conductive region, and wherein the first exposed conductive region (e.g., a cathode electrode) is placed in closer proximity to the peripheral nerve at the overlapping nerve region than the second exposed conductive region (e.g., a return electrode) being placed in proximity to the peripheral nerve.

In some embodiments, the one or more electrodes do not directly contact a portion of the peripheral nerve at the overlapping nerve region and is in proximity to the overlapping nerve region by less than about 15 millimeters.

In some embodiments, an electrode of the lead directly contacts a portion of the peripheral nerve at the overlapping nerve region.

In some embodiments, the peripheral nerve is selected from the group consisting of an enteric nerve, an autonomic nerve, and a cranial nerve (e.g., femoral nerve, saphenous nerve, sciatic nerve, tibial nerve, pudendal nerve, phrenic nerve, radial nerve, median nerve, ulnar nerve, intercostal nerve, suprascapular nerve, axillary nerve, lateral femoral cutaneous, lateral pectineal nerve).

In some embodiments, the method includes placing the lead proximal to the mid-thigh saphenous nerve block, e.g., to treat post-surgical knee pain.

In some embodiments, the method includes placing the lead proximal to the mid-thigh saphenous nerve block, e.g., to treat post-surgical knee pain.

In another aspect, a method is disclosed to inhibit a subject's perception of pain (e.g., acute pain, post-surgical pain, neuropathic pain, chronic pain, and head-and-face pain) by percutaneously blocking nerve conduction of a peripheral nerve (e.g., an afferent peripheral nerve) at a treatment site located proximal to the site of pain origination. The method includes delivering electrical stimulation to one or more exposed conductive regions of a percutaneous lead defining one or more electrodes, wherein the one or more electrodes are each placed at a treatment site of the subject to block nerve conduction via the electrical stimulation, wherein the one or more electrodes is placed in parallel, or substantially in parallel, to a long axis of a peripheral nerve over an overlapping nerve region (e.g., a collective overlapping region) of greater than about 3 mm, wherein an electrical field generated between an electrode of the percutaneous lead and the overlapping nerve region from the application of the electrical stimulation completely blocks action potential from forming at the overlapping nerve region.

In some embodiments, the method further includes surgically placing the percutaneous lead into the treatment site in an orientation parallel, or substantially parallel, to the long axis of the peripheral nerve.

In some embodiments, the method further includes interventionally placing the percutaneous lead into the treatment site in an orientation parallel, or substantially parallel, to the long axis of the peripheral nerve.

In some embodiments, the placement of the one or more electrodes places the percutaneous lead in an orientation parallel, or substantially parallel, to the long axis of the peripheral nerve.

In some embodiments, the one or more electrodes are placed in parallel, or substantially in parallel, to the long axis of the peripheral nerve over a distance selected from the group consisting of greater than about 4 mm, greater than about 5 mm, greater than about 6 mm, greater than about 7 mm, greater than about 8 mm, greater than about 9 mm, greater than about 1 cm, greater than about 2 cm, greater than about 2.5 cm, greater than about 3 cm, greater than about 3.5 cm, greater than about 4 cm, greater than about 4.5 cm, greater than about 5 cm, greater than about 5.5 cm, greater than about 6 cm, greater than about 6.5 cm, greater than about 7 cm, greater than about 7.5 cm, greater than about 8 cm, greater than about 8.5 cm, greater than about 9 cm, greater than about 9.5 cm, and up to about 10 cm.

In some embodiments, the electrical stimulation is predominantly a sinusoidal waveform.

In some embodiments, the electrical stimulation comprises high-frequency stimulation having one or more primary frequency harmonics between about 2 KHz and about 100 KHz. In some embodiments, the high-frequency stimulation is predominantly a sinusoidal waveform, a square waveform, a triangular waveform, a sinc waveform, a noisy waveform (e.g., an unstructured waveform having a pre-defined frequency distribution), or a chirp waveform (e.g., wherein any of which can having a high frequency component). In some embodiments, the electrical stimulation is predominantly charged balanced. In some embodiments, the electrical stimulation is charged unbalanced.

In some embodiments, the electrical stimulation comprises direct current stimulation.

In some embodiments, the one or more exposed conductive regions of the lead is configured as a monopolar electrode (e.g., with a return electrode placed at the surface of the skin).

In some embodiments, the one or more exposed conductive regions of the lead comprises a cathode region and an anodic region, and wherein the cathode region and anodic region collectively forms a multi-polar electrode (e.g., bipolar, tripolar, etc., electrode).

In some embodiments, the one or more exposed conductive regions of the lead include a first exposed conductive region and a second exposed conductive region, and wherein the first exposed conductive region (e.g., a cathode) is placed in closer proximity to the peripheral nerve at the overlapping nerve region than that of the second exposed conductive region (e.g., a return electrode).

In some embodiments, the method includes placing the lead proximal to the mid-thigh saphenous nerve block, e.g., to treat post-surgical knee pain.

In another aspect, a method is disclosed to percutaneously block nerve conduction (e.g., to inhibit a subject's perception of pain), the method includes percutaneously placing one or more exposed conductive regions of a percutaneous lead defining one or more electrodes into a treatment site, wherein the one or more exposed conductive regions of the percutaneous lead are placed in an orientation parallel, or substantially parallel, to a long axis of a peripheral nerve located at the treatment site; and applying electrical energy (e.g., constant high-frequency AC current or DC current) to the one or more exposed conductive regions of the percutaneous lead; wherein an electrical field generated by the high-frequency electrical stimulation at the overlapping nerve region sufficiently block nerve conduction through the overlapping nerve region.

In another aspect, a system is disclosed comprising an electronic control system configured to output electrical energy to one or more exposed conductive regions of a lead (e.g., a percutaneous lead) defining one or more electrodes, wherein the one or more electrodes are placed at a treatment site of a subject to block nerve conduction at the treatment site via an electrical stimulation (e.g., high frequency electrical stimulation between about 2 kHz and 100 kHz or DC electrical stimulation), and wherein the one or more electrodes are placed in parallel, or substantially in parallel (e.g., to put an electrode of the lead in parallel, or substantially parallel) to a long axis of a peripheral nerve over an overlapping nerve region (e.g., a collective overlapping nerve region) of greater than about 3 millimeters (e.g., from about 3 millimeters to about 10 centimeters) (e.g., wherein an electrical field generated by the high-frequency electrical stimulation at the overlapping nerve region sufficiently block nerve conduction through the overlapping nerve region). The electrical field generated between an electrode of the one or more electrodes and the overlapping nerve region from the application of the electrical stimulation can sufficiently block nerve conduction through the overlapping nerve region, e.g., to inhibit pain.

The electrical stimulation may predominantly a sinusoidal waveform, or may be a square waveform, a triangular waveform, a sinc waveform, a noisy waveform (e.g., an unstructured waveform having a pre-defined frequency distribution), or a chirp waveform (e.g., wherein any of which can having a high frequency component).

The electrical stimulation may comprise a high-frequency output (e.g., high-frequency AC current) or may comprise a constant flow of electric charge (e.g., DC current).

In another aspect, a non-transitory computer readable medium is disclosed having instructions stored thereon, wherein execution of the instructions by the processor, cause the processor to output electrical energy to one or more exposed conductive regions of a percutaneous lead defining one or more electrodes, wherein the one or more electrodes are placed at a treatment site of a subject to block nerve conduction at the treatment site via an electrical stimulation, and wherein the one or more electrodes are placed in parallel, or substantially in parallel to a long axis of a peripheral nerve over an overlapping nerve region of greater than about 3 millimeters, wherein an electrical field generated by the electrical stimulation at the overlapping nerve region sufficiently block nerve conduction through the overlapping nerve region.

In another aspect, a system for blocking (e.g., selectively and temporarily blocking) painful sensations hosted by a target nerve is provided. The system includes one or more percutaneous electrodes; and an electronic control system electrically attached to each electrode. The electronic control system is configured to deliver electrical stimulation to the target nerve from an external waveform generator, wherein the electrical stimulation has a frequency that is greater than about 1.5 kilohertz and less than about 75 kilohertz, wherein a ramp rate of less than about 2 milliamps/second is utilized to gradually increase an intensity at which the electrical stimulation is delivered until a desired stimulation intensity is reached.

In some embodiments, the painful sensations can be associated with acute pain.

In some embodiments, the target nerve can be a peripheral nerve.

In yet another embodiment, non-targeted motor activity and non-targeted sensory activity are not blocked via the system.

In some embodiments, the one or more percutaneous electrodes can be configured for placement a distance away from the target nerve, wherein the distance ranges from about 0.5 millimeters to about 15 millimeters.

In some embodiments, the electrical stimulation can include a high-frequency oscillating waveform.

In some embodiments, the electrical stimulation comprises direct current stimulation.

In some embodiments, the electric stimulation comprises high-frequency stimulation, wherein the electrical stimulation is less than about 50 milliamps peak.

In some embodiments, the electrical stimulation intensity is delivered for a time period ranging from about 1 hour to about 6 weeks (e.g., to treat and/or manage pain, e.g., acute pain and/or chronic pain). Further, the system can facilitate a carry-over blocking effect, wherein the blocking of painful sensations hosted by the target nerve can extend for a time period that is up to about 1000% of the time period during which the desired stimulation intensity is delivered.

In some embodiments, the one or more percutaneous electrodes can include an fixable element (e.g., having inflatable material).

In one more embodiment, the electronic control system can be configured to determine a sensory threshold of a patient via patient feedback, wherein the sensory threshold can be used to predict a threshold for painful sensations elicited by the electrical stimulation, predict a blocking amplitude, predict an optimal ramp rate, or a combination thereof. Further, the electronic control system can be configured to adjust the blocking amplitude to range from about 110% to about 1000% of the sensory threshold.

In some embodiments, the system can include one or more electromyography electrodes, wherein the electronic control system can be configured to deliver a test electrical stimulation prior to delivery of the electrical stimulation and monitor for nociceptive reflect activity in the patient via electromyography (e.g., via SNAP recording to help guide probe to therapeutic range) to confirm accurate placement of the one or more percutaneous electrodes, wherein an absence of short bursts of muscle activity within about 5 milliseconds to about 15 milliseconds after delivery of the test electrical stimulation confirms accurate placement of the one or more percutaneous electrodes.

In some embodiments, the target nerve can be the saphenous nerve, wherein the one or more percutaneous electrodes can be configured for insertion into the adductor canal. Moreover, the one or more percutaneous electrodes can be configured for insertion into a cavity defined by an intermuscular septum of the adductor canal.

In some embodiments, a method for blocking (e.g., selectively and temporarily blocking) painful sensations hosted by a target nerve is provided. The method includes identifying the target nerve; inserting one or more percutaneous electrodes near the target nerve (e.g., in parallel, or substantially parallel to the target nerve over an overlapping region of at least 3 mm); and delivering electrical stimulation to the target nerve from a waveform generator (e.g., external or implantable waveform generator), wherein the electrical stimulation has a frequency that is greater than about 1.5 kilohertz and less than about 75 kilohertz, and wherein a ramp rate of less than about 2 milliamps/second is utilized to gradually increase the electrical stimulation until a desired or specified electrical stimulation is reached.

In one embodiment, the painful sensations can be associated with acute pain.

In some embodiments, the target nerve can be a peripheral nerve.

In some embodiments, non-targeted motor activity and non-targeted sensory activity are not blocked via the method.

In some embodiments, the one or more percutaneous electrodes are inserted a distance away from the target nerve, wherein the distance ranges from about 0.5 millimeters to about 15 millimeters.

In some embodiments, the electrical stimulation include a sinusoidal waveform.

In some embodiments, the electrical stimulation comprises direct current stimulation.

In some embodiments, the electrical stimulation comprises high-frequency current stimulation, wherein the electrical stimulation is less than about 50 milliamps peak.

In some embodiments, the electrical stimulation is delivered for a time period ranging from about 1 hour to about 6 weeks. Further, a carry-over blocking effect, in some embodiments, may be observed upon delivery of the electrical stimulation, wherein the blocking of painful sensations hosted by the target nerve can extend for a time period that is up to about 1000% of the time period during which the desired stimulation intensity is delivered.

In some embodiments, the one or more percutaneous electrodes can include a fixation element (e.g., having inflatable material).

In some embodiments, the method includes the step of determining a sensory threshold of a patient via patient feedback, wherein the sensory threshold can be used to predict a threshold for painful sensations hosted by the electrical stimulation, predict a blocking amplitude, predict an optimal ramp rate, or a combination thereof.

In some embodiments, the electronic control system is configured to adjust the blocking amplitude to range from about 110% to about 1000% of the sensory threshold.

In some embodiments, the method includes the steps of delivering a test electrical stimulation prior to delivery of the electrical stimulation and monitoring for nociceptive reflect activity in the patient by electromyography via one or more electromyography electrodes; and confirming accurate placement of the one or more percutaneous electrodes, wherein an absence of short bursts of muscle activity within about 5 milliseconds to about 15 milliseconds after delivering the test electrical stimulation confirms accurate placement of the one or more percutaneous electrodes.

In some embodiments, the target nerve is the saphenous nerve, wherein the one or more percutaneous electrodes can be inserted into the adductor canal.

In some embodiments, the one or more percutaneous electrodes is configured to be inserted into a cavity defined by an intermuscular septum of the adductor canal.

In some embodiments, the method includes placing the lead proximal to the mid-thigh saphenous nerve block, e.g., to treat post-surgical knee pain.

In another aspect, a percutaneous lead (e.g., bi-polar lead) is disclosed comprising: a longitudinal body having a first end and a second end that define a long axis of the longitudinal body, wherein the first end terminates to form a distal tip (e.g., a distal ball tip), the longitudinal body comprising two or more concentric members, including a first concentric member and a second concentric member, wherein an outer surface of the first concentric member contacts an inner surface of the second concentric member, wherein the first concentric member has a first insulated body having a first length defined at least by the first end, the first concentric member comprising a first set of conductive members formed in the insulated body, wherein the insulated body includes one or more exposed surface regions located proximal to the first end to form a first set of electrodes, wherein the first set of electrode has an exposed length, or collective exposed length, between about 1 mm and 10 cm (e.g., between about 3 mm and about 10 mm) (e.g., between about 4 mm and about 8 mm); wherein the second concentric member has a second insulated body having a second length, wherein the second length is less than, and overlaps with, the first length, the second concentric member comprising a second set of conductive members formed in the second insulated body, wherein the second insulated body includes one or more exposed surface regions to form a second set of electrodes, wherein the second set of electrode has an exposed length, or collective exposed length, between about 1 mm and 10 cm.

In some embodiments, the first insulated body forms a lumen configured to receive and mate with a removable stiffening stylet (e.g., wherein the removable stiffening stylet collectively the longitudinal body has a combined stiffness suitable for advancement of the percutaneous lead through at least about 1 cm of body tissue (e.g., up to at least about 5 cm of body tissue, e.g., up to at least about 10 cm of body tissue)).

In some embodiments, the first set of electrodes can be placed in parallel, or substantially in parallel (e.g., to put an electrode of the lead in parallel, or substantially parallel) to a long axis of a peripheral nerve over an overlapping nerve region (e.g., a collective overlapping nerve region) of greater than about 3 millimeters (e.g., from about 3 millimeters to about 10 centimeters) (e.g., wherein an electrical field generated by the high-frequency electrical stimulation at the overlapping nerve region sufficiently block nerve conduction through the overlapping nerve region, e.g., to inhibit pain).

In some embodiments, the first set of electrodes and second set of electrodes can be placed in parallel, or substantially in parallel (e.g., to put an electrode of the lead in parallel, or substantially parallel) to a long axis of a peripheral nerve over an overlapping nerve region (e.g., a collective overlapping nerve region) of greater than about 3 millimeters (e.g., from about 3 millimeters to about 10 centimeters) (e.g., wherein an electrical field generated by the high-frequency electrical stimulation at the overlapping nerve region sufficiently block nerve conduction through the overlapping nerve region, e.g., to inhibit pain).

In some embodiments, conductive elements of the first set of conductive members are interlaced (e.g., to form a braid or mesh).

In some embodiments, conductive elements of the first set of conductive members are coiled.

In some embodiments, conductive elements of the first set of conductive members are interlaced (e.g., to form a braid or mesh), and wherein conductive elements of the second set of conductive members are interlaced (e.g., to form a braid or mesh) (e.g., to form a braided percutaneous lead).

In some embodiments, conductive elements of the first set of conductive members are coiled, and wherein conductive elements of the second set of conductive members are coiled (e.g., to form a coiled percutaneous lead).

In some embodiments, conductive elements of the first set of conductive members are interlaced (e.g., to form a braid or mesh), and wherein conductive elements of the first set of conductive members are coiled (e.g., to form braided-coiled percutaneous lead).

In some embodiments, conductive elements of the first set of conductive members are coiled, and wherein conductive elements of the first set of conductive members are interlaced (e.g., to form a braid or mesh) (e.g., to form coiled-braided percutaneous lead).

In some embodiments, the percutaneous lead further includes a third concentric member, wherein an outer surface of the second concentric member contacts an inner surface of the third concentric member, wherein the third concentric member has a third insulated body having a third length, wherein the third length is less than, and overlaps with, the second length, the third concentric member comprising a third set of conductive members formed in the third insulated body, wherein the third insulated body includes one or more exposed surface regions to form a third set of electrodes, wherein the third set of electrode has an exposed length, or collective exposed length, between about 1 mm and 10 cm.

In some embodiments, the percutaneous lead further includes a third concentric member, wherein an outer surface of the first concentric member contacts an inner surface of the third concentric member, wherein the third concentric member has a third insulated body having a third length, wherein the third length does not overlap with the second length, the third concentric member comprising a third set of conductive members formed in the third insulated body, wherein the third insulated body includes one or more exposed surface regions to form a third set of electrodes, wherein the third set of electrode has an exposed length, or collective exposed length, between about 1 mm and 10 cm.

In some embodiments, the insulated body of the first concentric member includes one or more exposed surface regions located proximal to the second end to form a third set of electrodes.

In some embodiments, the insulated body of the second concentric member includes one or more exposed surface regions located proximal to the second end to form a fourth set of electrodes.

In some embodiments, conductive elements of the first set of conductive members are interlaced (e.g., to form a braid or mesh with a first pitch), wherein conductive elements of the second set of conductive members are interlaced (e.g., to form a braid or mesh with a second pitch), and wherein an associated spacing between conductive elements of the first set of conductive members is the same as an associated spacing between conductive elements of the second set of conductive members.

In some embodiments, conductive elements of the first set of conductive members are interlaced (e.g., to form a braid with a first pitch), wherein conductive elements of the second set of conductive members are interlaced (e.g., to form a braid with a second pitch), and wherein an associated spacing between conductive elements of the first set of conductive members is different than an associated spacing between conductive elements of the second set of conductive members.

In some embodiments, the longitudinal body has a predominantly circular cross-section.

In some embodiments, the longitudinal body has a non-circular cross-section.

In some embodiments, the removable stiffening stylet has a cross-sectional profile between about 50 $mils^2$ (0.00005 $inch^2$) and about 80 $mils^2$ (0.00008 $inch^2$).

In some embodiments, the longitudinal body has a first constant cross-section and a second constant cross-section.

In some embodiments, the first constant cross-section is located proximal to, or defines a portion of, the distal tip.

In some embodiments, the second insulated body encapsulates the conductive members to form a wire, the wire being coiled to form the first concentric member.

In some embodiments, the first insulated body encapsulates the conductive members to form a wire, the wire being coiled to form the first concentric member.

In some embodiments, the second insulated body encapsulates a second conductive member of the second set of conductive members to form a second wire, the second wire being coiled to form the second concentric member.

In some embodiments, the first concentric member comprises multiple wires, each having a insulated body encapsulating a respective conductive member. In some embodiments, the multiple wires comprises a number of wires selected from the group consisting of 2, 3, 4, 5, 6, 7, and 8.

In some embodiments, the second concentric member comprises multiple wires, each having a insulated body encapsulating a respective conductive member. In some embodiments, the multiple wires comprises a number of wires selected from the group consisting of 2, 3, 4, 5, 6, 7, and 8.

In some embodiments, each of the first set of conductive members has a defined coil spacing to a nearby adjacent conductor.

In some embodiments, the defined coil spacing is uniform.

In some embodiments, the defined coil spacing is non-uniform.

In some embodiments, the first concentric member has a flat cross-sectional profile or a flat cross-sectional profile.

In some embodiments, the longitudinal body comprises an opening proximal to, or at, the second end, and wherein the opening is configured to communicatively engage with a syringe or an adapter for fluid injection.

In some embodiments, the longitudinal body comprises a distal opening proximal to, or at, the second end, and wherein the distal opening is defined in the longitudinal body for delivery of fluid injection at the distal opening.

In some embodiments, the longitudinal body comprises a plurality of markings indicative of depth of insertion.

In some embodiments, the longitudinal body comprises one or more markings at, or proximal to, the first end (e.g., indicate that full length of lead has been removed).

In some embodiments, the percutaneous lead further includes a cable adaptor coupled to the second end, wherein the cable adaptor comprises a transparent material and is configured to provide visual confirmation of proper contact (e.g., alignment and connection) between the electrode and an external electrical stimulation system.

In some embodiments, the percutaneous lead further includes a second cable adaptor coupled to the second end, wherein the second cable adaptor provides a port for fluid delivery through the percutaneous lead (e.g., after lead has been connected to adapter).

In some embodiments, the percutaneous lead further includes a third cable adaptor coupled to the second end, wherein the third cable adaptor is configured for one-handed connection between the third cable adaptor and the percutaneous lead (e.g., further comprising a rubber components which secures the percutaneous lead near the third cable adaptor; and a rotatable body that moves the percutaneous lead into contact with the third cable adaptor when moved to a closed configuration).

In some embodiments, the insulation member comprises a polymer (e.g., selected from the group consisting of i) polyimide, ii) a thermoplastic elastomer consist of polyamide and polyether backbone blocks (e.g., Pebax®), silicone, and polyurethane).

In some embodiments, the conductive member that forms the one or more exposed surface regions comprises a metal or a metal alloy (e.g., selected from the group consisting of 304 stainless steel, 316 stainless steel, platinum, platinum iridium, carbon, and a combination thereof).

In some embodiments, the percutaneous lead comprise a material suitable to be imaged via ultrasound. In some embodiments, the percutaneous lead comprise a material suitable to be imaged via CT scanner, MRI scanner, or x-ray scanner.

In some embodiments, the percutaneous lead is configured to be placed proximal to the mid-thigh saphenous nerve block, e.g., to treat post-surgical knee pain.

In another aspect, a percutaneous lead (e.g., monopolar lead) is disclosed comprising a longitudinal body having a first end and a second end that define a long axis of the longitudinal body, wherein the first end terminates to form a distal tip (e.g., a distal ball tip), the longitudinal body comprising a insulated body having a length defined at least by the first end, the insulated body comprising a set of conductive members, wherein the insulated body includes one or more exposed surface regions located proximal to the first end to form a set of electrodes, wherein the set of electrode has an exposed length, or collective exposed length, between about 1 mm and 10 cm (e.g., between about 3 mm and about 10 mm) (e.g., between about 4 mm and about 8 mm), wherein the insulated body forms a lumen configured to receive and mate with a removable stiffening stylet (e.g., wherein the removable stiffening stylet collectively the longitudinal body has a combined stiffness suitable for advancement of the percutaneous lead through at least about 1 cm of body tissue (e.g., up to at least about 5 cm of body tissue, e.g., up to at least about 10 cm of body tissue)). In some embodiments, conductive elements of the set of conductive members are interlaced (e.g., to form a braid or mesh). In other embodiments, conductive elements of the set of conductive members are coiled.

In another aspect, a kit is disclosed (e.g., a single use or reusable kit) (e.g., to place a percutaneous lead into a treatment site of a subject that aligns a long axis associated with the percutaneous lead in parallel, or substantially in parallel, to a long axis of a peripheral nerve). The kit includes a percutaneous lead; and a placement apparatus having a body comprising an entry port configured to receive the percutaneous lead, wherein the percutaneous lead is placed at a first angle of insertion defined with respect to an associated surface of the treatment site, and wherein the first angle of insertion is between about 10 degrees and about 90 degrees, and wherein the body includes a fixed curve region or a flexible region that is bendable to form a curve, to direct the percutaneous lead to a second angle that is parallel, or substantially parallel, to a long axis of a peripheral nerve to provide placement of one or more electrodes of the percutaneous lead over an overlapping nerve region greater than about 3 mm, wherein an electrical field generated between the electrode and the overlapping nerve region prevent action potential from forming at the overlapping nerve region to block nerve conduction through the overlapping nerve region.

In some embodiments, the body of the placement apparatus forms a needle, wherein the needle includes a fixed curve (e.g., unbendable curve) or a flexible region configured to be bent (e.g., reversibly bent, e.g., by the physician to a desired curvature) to direct the percutaneous lead from the first angle to the second angle.

In some embodiments, the body forms an introducer, wherein the introducer includes a fixed curve (e.g., unbendable curve) or the flexible region to direct the percutaneous lead from the first angle to the second angle.

In some embodiments, the kit further includes a needle or an introducer; wherein the body of the placement apparatus forms a sheath, wherein the sheath is insertable through or around the needle or introducer, and wherein retraction of the needle or introducer from the sheath shapes the sheath with a curve to direct the percutaneous lead from the first angle to the second angle.

In some embodiments, the body of the placement apparatus is configured to direct a leading point of the percutaneous lead at least about 1 cm (e.g., between about 1 cm and 10 cm) (e.g., between about 3 cm and 4 cm) at the second angle parallel, or substantially parallel, to the long axis of the peripheral nerve.

In some embodiments, the kit further includes a cable adaptor configured to be coupled to percutaneous lead, wherein the cable adaptor comprises a transparent material and is configured to provide visual confirmation of proper contact (e.g., alignment and connection) between the one or more electrode and an external electrical stimulation system.

In some embodiments, the kit further includes a second cable adaptor configured to be coupled to percutaneous lead, wherein the second cable adaptor provides a port for fluid delivery through the percutaneous lead (e.g., after lead has been connected to adapter).

In some embodiments, the kit further includes a third cable adaptor configured to be coupled to percutaneous lead, wherein the third cable adaptor is configured for one-handed connection between the third cable adaptor and the percutaneous lead (e.g., comprising a rubber components which secures the percutaneous lead near the third cable adaptor; and a rotatable body that moves the percutaneous lead into contact with the third cable adaptor when moved to a closed configuration.

In some embodiments, the kit includes a cable adaptor configured to be coupled to percutaneous lead, wherein the cable adaptor comprises a transparent material and is configured to provide visual confirmation of proper contact between the one or more electrode and an external electrical stimulation system, wherein the cable adaptor is configured to provide a port for fluid delivery through the percutaneous lead, and wherein the cable adaptor is configured for one-handed connection between the third cable adaptor and the percutaneous lead.

In some embodiments, the kit includes a cable adaptor configured to be coupled to percutaneous lead, wherein the cable adaptor comprises a transparent material and is configured to provide visual confirmation of proper contact between the one or more electrode and an external electrical stimulation system, and wherein the cable adaptor is configured to provide a port for fluid delivery through the percutaneous lead.

In some embodiments, the kit includes percutaneous lead configured to be placed proximal to the mid-thigh saphenous nerve block, e.g., to treat post-surgical knee pain.

In some embodiments, the kit further includes an electrical stimulation system configured to deliver electrical stimulation to the one or more electrodes; and electrical cable to connect a connector of the electrical stimulation system to a connector of the percutaneous lead to establish electrical contact with the one or more electrodes.

In some embodiments, the electrical stimulation system is an external electrical stimulation system.

In some embodiments, the electrical stimulation system is an implantable electrical stimulation system.

In some embodiments, the electrical stimulation system is configured to deliver high-frequency stimulation having at least one predominant frequency harmonic between about 2 kHz and 100 kHz.

In some embodiments, the electrical stimulation system is configured to deliver direct current stimulation.

In some embodiments, a controller of the electrical stimulation system is configured to adjust the delivered electrical stimulation (direct current stimulation or high-frequency stimulation) at a pre-defined ramp rate, wherein the ramp rate is less than about 2 milliamps/second (e.g., to prevent onset activity).

In another aspect, a method is disclosed of operating an introducer to place a percutaneous lead into a treatment site of a subject to block nerve conduction (e.g., to treat pain). The method includes receiving a percutaneous lead inserted into an entry port of a placement assembly (e.g., a needle, introducer, or sheath), wherein the percutaneous lead is placed at a first angle of insertion defined with respect to an associated surface of the treatment site, and wherein the first angle of insertion is between about 10 degrees and about 90 degrees (e.g., between about 25 degrees and 60 degrees, e.g., at about 30 degrees), directing the percutaneous lead to a second angle that is parallel, or substantially parallel, to a long axis of a peripheral nerve to place one or more electrodes of the percutaneous lead over an overlapping nerve region of greater than about 3 mm, wherein an electrical field generated between the electrode and the overlapping nerve region prevent action potential from forming at the overlapping nerve region to block nerve conduction through the overlapping nerve region.

In some embodiments, the placement of the percutaneous lead orients an electrode of the percutaneous lead in parallel, or substantially in parallel, to the overlapping nerve region over a length of at least about 3 mm.

In some embodiments, the method further includes percutaneously placing the placement assembly into the treatment site, wherein during the placement a tip comprising an exit port of the placement assembly is placed at a pre-defined distance or pre-defined orientation from the peripheral nerve.

In some embodiments, the placement assembly establishes a path for insertion of the percutaneous lead into tissue to put the one or more electrodes in parallel, or substantially parallel, to the long axis of the peripheral nerve.

In some embodiments, the method further includes percutaneously placing the placement assembly into the treatment site, wherein the placement assembly includes a fixed curve (e.g., unbendable curve) or includes a flexible region configured to be bent (e.g., reversibly bent, e.g., by the physician to a desired curvature) to direct the percutaneous lead from the first angle to the second angle.

In some embodiments, the method further includes percutaneously placing a second placement assembly comprising a needle or introducer into the treatment site; and placing (e.g., percutaneously placing) the placement assembly comprising a sheath through, or around, the second placement assembly, wherein retraction of the second placement assembly directs the placement assembly into a pre-defined angle configured to direct the percutaneous lead from the first angle to the second angle.

In some embodiments, the placement assembly is engaged to the second placement assembly, wherein the placement assembly and second placement assembly are engaged to the second placement assembly.

In some embodiments, the method further includes locking via a member of the percutaneous lead with the placement assembly, wherein the percutaneous lead is advanced with the placement assembly when the member is engaged.

In some embodiments, the percutaneous lead comprises a stylet inserted into a lumen of the percutaneous lead, the method further includes removing the stylet once the one or more electrodes of the percutaneous lead are placed over the overlapping nerve region.

In some embodiments, the placement assembly comprises one or more placement electrodes, the method further includes: applying an electrical energy to the one or more placement electrodes of the placement assembly to confirm placement of the placement assembly.

In some embodiments, the method further includes locking, via the placement assembly, retraction of the percutaneous lead from the placement assembly.

In some embodiments, the method further includes locking, via the placement assembly, advancement of the percutaneous lead through the placement assembly during a first instance during the placement of the percutaneous lead; and locking, via the placement assembly, retraction of the percutaneous lead from the placement assembly during a second instance during the placement of the percutaneous lead.

In some embodiments, a leading point of the percutaneous lead is advanced at least about 1 cm (e.g., between about 1 cm and 10 cm) (e.g., between about 3 cm and 4 cm) at the second angle parallel, or substantially parallel, to the long axis of the peripheral nerve.

In some embodiments, the method further includes receiving a portion of the percutaneous lead having a predominantly non-circular cross-section (e.g., wherein the non-circular cross-section has a cross-sectional profile between about 0.4 mm and 0.75 mm in diameter) In some embodiments, the method further includes receiving a portion of the percutaneous lead having a circular cross-section, or near circular cross-section (e.g., wherein the non-circular cross-section has a cross-sectional profile between about 0.4 mm and 0.75 mm in diameter).

In some embodiments, the placement of the percutaneous lead into the treatment site is guided by an imaging system (e.g., ultrasound).

In some embodiments, the placement of the percutaneous lead into the treatment site is guided by a stimulation needle.

In some embodiments, the placement of the percutaneous lead into the treatment site is performed without prior incisions at the treatment site (e.g., and without use of fluid injection).

In some embodiments, the percutaneous lead is placed proximal to the mid-thigh saphenous nerve block, e.g., to treat post-surgical knee pain.

In another aspect, an apparatus is disclosed, the apparatus being (e.g., placement assembly, e.g., needle, introducer, sheath, or combination thereof) configured to place a percutaneous lead into a treatment site of a subject that aligns a long axis associated with the percutaneous lead in parallel, or substantially in parallel (e.g., to put an electrode of the lead in parallel, or substantially parallel) to a long axis of a peripheral nerve (e.g., phrenic, radial, median, ulnar, intercostal, femoral, sciatic, etc.). The apparatus includes a body comprising an entry port configured to receive a percutaneous lead, wherein the percutaneous lead is placed at a first angle of insertion defined with respect to an associated surface of the treatment site, wherein the first angle of insertion is between about 10 degrees and about 90 degrees, and wherein the body includes a fixed curve region or a flexible region that is bendable to form a curve, to direct the percutaneous lead to a second angle that is parallel, or substantially parallel, to a long axis of a peripheral nerve to provide placement of one or more electrodes of the percutaneous lead over an overlapping nerve region greater than about 3 mm.

In some embodiments, the body forms a needle, and wherein the needle includes the fixed curve (e.g., unbendable curve) or the flexible region to direct the percutaneous lead from the first angle to the second angle.

In some embodiments, the body forms an introducer, wherein the introducer includes a fixed curve (e.g., unbendable curve) or the flexible region to direct the percutaneous lead from the first angle to the second angle.

In some embodiments, apparatus further includes a second body, wherein the body forms a sheath, wherein the second body forms a needle or introducer through which, or over which, the sheath can be inserted through or around, and wherein retraction of the needle or introducer from the sheath shapes the sheath with a curve to direct the percutaneous lead from the first angle to the second angle.

In some embodiments, the apparatus further includes a lock engage-able at a control end of the body, wherein the lock is configured to restrain advancement of the percutaneous lead through the body of the apparatus.

In some embodiments, the apparatus further includes a lock engage-able at a control end of the body, wherein the lock is configured to restrain retraction of the percutaneous lead from the body of the apparatus.

In some embodiments, the apparatus further includes a lock engage-able at a control end of the body, wherein the lock is configured to restrain advancement of the percutaneous lead through the body of the apparatus and to restrain retraction of the percutaneous lead from the body of the apparatus.

In some embodiments, an electrical field generated by an oscillating electrical stimulation applied between an electrode of the inserted percutaneous lead and the overlapping nerve region modulates the targeted neural tissue to selectively block nerve conduction through the overlapping nerve region while preserving sensory function upstream to the treatment site and motor function.

In some embodiments, the body is configured to direct a leading point of the percutaneous lead at least about 1 cm (e.g., between about 1 cm and 10 cm) (e.g., between about 3 cm and 4 cm) at the second angle parallel, or substantially parallel, to the long axis of the peripheral nerve.

In some embodiments, the apparatus is configured to be placed proximal to the mid-thigh saphenous nerve block, e.g., to treat post-surgical knee pain.

In some embodiments, the apparatus (e.g., body of the apparatus) is configured to be placed proximal to the mid-thigh saphenous nerve block, e.g., to treat post-surgical knee pain.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which:

FIG. 4B is a diagram of an example placement assemblies that may be used to deliver the percutaneous lead to the treatment at an orientation parallel, or substantially parallel, to the target nerve, in accordance with an embodiment.

FIGS. 5, 6, 7A, 7B, 8A, and 8B are schematics of a percutaneous lead configured with braided electrodes to be delivered parallel, or substantially in parallel, to a long axis of a target nerve, in accordance with an illustrative embodiment.

FIGS. 9, 10, 11A, 11B, 12A, and 12B are schematics of a percutaneous lead configured with coiled electrodes to be delivered parallel, or substantially in parallel, to a long axis of a target nerve, in accordance with another illustrative embodiment.

FIGS. 16, 17A, 17B, and 17C show experimental results of a percutaneous method of treating pain via percutaneous electrodes placed in parallel orientation to a target nerve and stimulated via high-frequency electrical stimulation, in accordance with an illustrative embodiment.

FIGS. 18A, 18B, 19A, 19B, 19C, 19D, and 19E show experimental results from an animal study of a method of treating pain via electrodes placed in parallel orientation to a target nerve and stimulated via direct-current electrical stimulation, in accordance with an illustrative embodiment.

FIGS. 23A, 23B, 23C, and 23D each shows a perspective side view of an exemplary percutaneous electrode as illustrated in FIG. 22.

FIG. 30 is diagram of experimental results illustrating that simulated acute pain hosted on the nociceptive reflex as elicited by conventional electrical stimulation of the nerve at the foot can be treated via percutaneous high frequency electrical stimulation of the saphenous nerve at a site proximal to the ankle to block nerve conduction there at.

Figure 1:
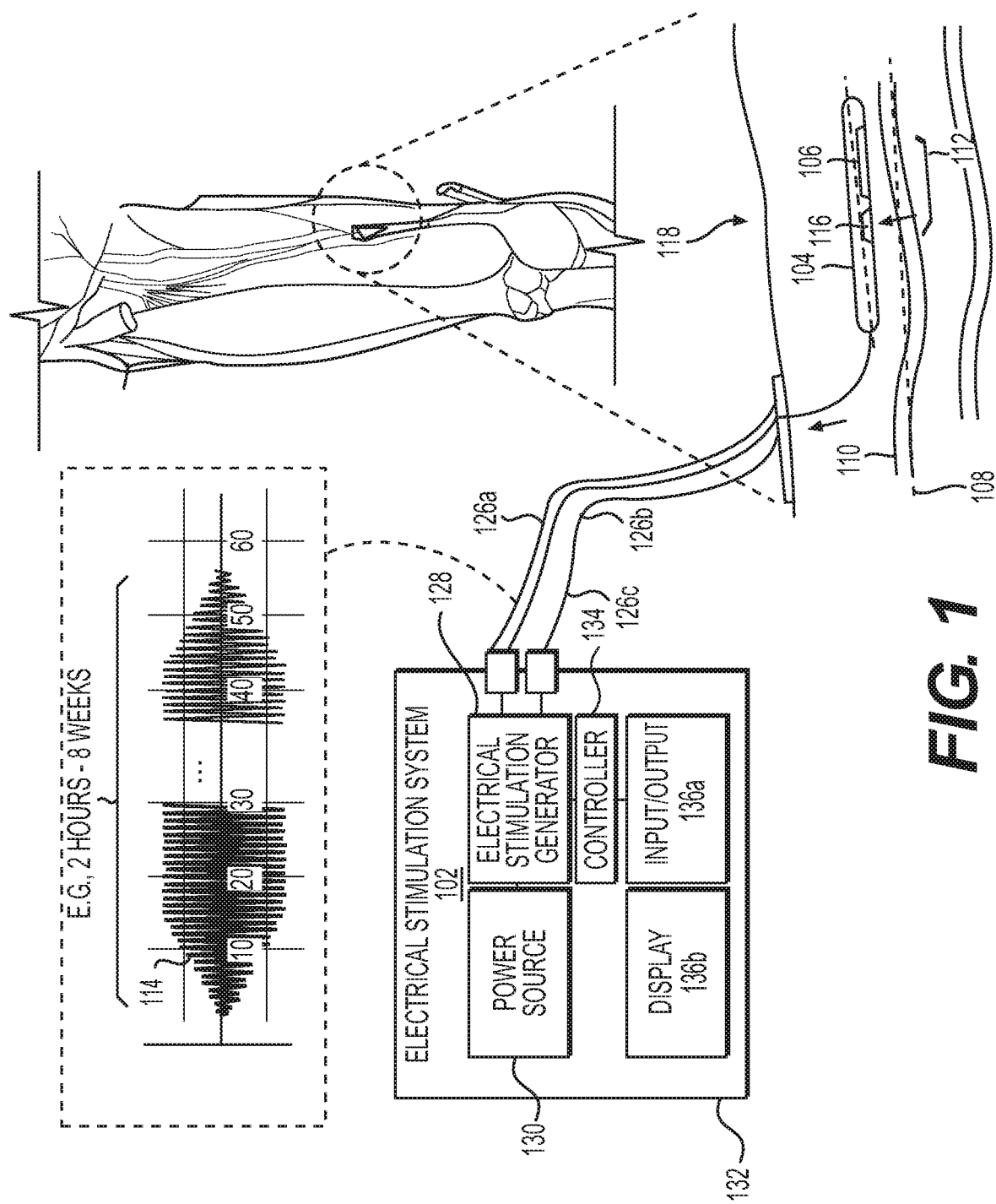
FIG. 1 is a diagram of an exemplary electrical stimulation system configured to deliver electrical stimulation from a percutaneous lead comprising one or more percutaneous electrode(s) placed in parallel, or substantially in parallel, and without direct contact, to a long axis of a target nerve over an overlapping nerve region of greater than about 3 millimeters, to block nerve conduction through the overlapping nerve region, in accordance with an illustrative embodiment.

Repeat use of reference characters in the present specification and drawings is intended to represent the same or analogous features or elements of the present invention.

DEFINITIONS

As used herein, the terms "electrical stimulation" or "electrical nerve-blocking stimulation" or "electrical nerve-block" refer to electrical energy delivered by a controller to the tissues by means of one or more electrodes. The electrical energy, upon reaching an axon of a neuron, blocks the propagation of action potentials through the stimulation site, resulting in a partial or complete cessation of nerve conduction, e.g., that partially or completely inhibit painful sensations by the patient at the stimulation site. Where the electrical stimulation does so without eliciting non-targeted motor and sensory activity, the disclosure will indicate as such.

The electrical energy, in some embodiments, is characterized as a high-frequency temporally-varying voltage, current, power, and/or other electrical measure, e.g., as a high-frequency alternating current. In other embodiments, the electrical energy is characterized as a constant current. Delivery of the electrical energy to the target tissue is referred to as an electrical treatment, an electrical therapy, or simply a treatment or a therapy. The electrical energy creates an electrical field in the tissue such that control of the electrical energy strongly influences control of the electrical field in the tissue.

As used herein, the term "nerve block" refers to an interrupting, hindering or preventing the passage of impulses along a neuron's axon within a nerve. The term also encompasses a form of regional anesthesia in which insensibility is produced in a part of the body by interrupting, hindering or preventing the passage of action potentials along a neuron's axon, making the nerve inoperable.

As used herein, the term "nervous structure" or "neural structure" refers to a structure including neural and non-neural tissue. In addition to neural tissue (such as neurons and components of neurons including axons, cell bodies, dendrites and synapses of neurons), nervous structures may also include non-neural tissue such as glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc.

As used herein, the terms "percutaneous" and/or "percutaneously" refer to electrical stimulation applied utilizing one or more electrodes penetrating through the surface of the skin so an electrode delivering electrical stimulation to a target nerve beneath the skin is also located beneath the skin. It is contemplated that return electrodes or anodes may be located beneath the skin or on the surface of the skin.

As used herein, the term "percutaneous electrode" refers to electrode assemblies, e.g., in a percutaneous lead, inserted through the skin and directed into the vicinity of the nerve (mm to cm distance), without having to contact the nerve, in a minimally invasive fashion to electrically affect neural structure.

As used herein, the term "painful sensation" refers to a disagreeable sensation generated by the activation of sensory nociceptors or nerve fibers. Nociception describes the perception of acute pain and is generally caused by activation of sensory nociceptors or by disruption of nociceptor pathways (e.g. severed neurons or disrupted nociceptors). Chronic pain sensation can also be generated by activation of nerve fibers which result in a disagreeable perception similar in nature to that generated by activation of nociceptors (for example, neuropathic pain). In some cases, such as following a surgery intended to treat chronic pain, both acute pain sensation and chronic pain sensation may contribute in a mixed manner to the overall pain sensation.

As used herein, the term "target nerve" may refer to mixed nerves containing motor nerve fibers and sensory nerve fibers. It may additionally refer to sensory nerves containing only sensory nerve fibers and/or to motor nerves containing only motor nerve fibers.

As used herein, the term "peripheral nerve" refers to motor and/or sensory nerves or ganglia structure outside of the central nervous system that connect the brain and spinal cord (the central nervous system) to the entire human body.

The terms "proximal" and "distal" are used herein as relative terms that refer to regions of a nerve, positions of nerves, or regions of a stimulation device. "Proximal" means a position closer to the spinal cord, brain, or central nervous system, whereas "distal" indicates a position farther from the spinal cord, brain, or central nervous system. When referring to the position on a neural structure in the peripheral nervous system or along an appendage, proximal and distal refer to positions either closer to the central nervous system or further from the central nervous system along the pathway followed by that neural structure or appendage. When referring to the position on a neural structure in the spinal cord, proximal and distal refer to positions either closer to the brain or further from the brain along the pathway followed by the neural structure.

As used herein, the term "stimulating electrode," also referred to in the case of monopolar stimulation as "the cathode," refers to an electrode responsible for delivering the therapeutic energy to the nerve. In the case of bipolar or multipolar stimulation, all of the electrical contacts are considered to be stimulating electrodes.

As used herein, "return electrode," also referred to in the case of monopolar stimulation as "the anode," refers to an electrode responsible for providing a return path for current that flows through the body. For example, the return electrode provides a return path for the current which is delivered to the target neural structure via the stimulating electrode.

As used herein, "modulate" refers to modifying or changing the transmission of action potential. For example, this includes both excitation, pacing, and inhibition/interruption of the passage of impulses along a neuron's axon within a nerve. Modulating nerve fiber activity includes inhibiting nerve signal transmission to the point of creating a blocking effect, including a partial and a complete blocking effect. Modulating nerve activity also includes modifying the trafficking of molecules such as macromolecules along the nerve fiber. Modulating nerve activity also includes changing downstream function of the neuron (for example at cell bodies and synapses), modifying signaling in a way that changes signaling in other neurons (for example neurons in the central nervous system such as the spinal cord or the brain), modifying the function of non-neural tissue in the neural structure, or otherwise modifying the processes, function, or activity in the target neural or non-neural tissue.

As used herein, the terms "inhibit" and "attenuate" refer to any level of reduction, including partial reduction or complete reduction of nerve signal activity through a nervous structure, e.g., the reduction of the passage of impulses along a neuron's axion within a nerve.

DETAILED DESCRIPTION OF THE INVENTION

Reference will now be made in detail to one or more embodiments of the invention, examples of which are illustrated in the drawings. Each example and embodiment is provided by way of explanation of the embodiment and is not meant as a limitation of the disclosure. For example, features illustrated or described as part of one embodiment may be used with another embodiment to yield still a further embodiment. It is intended that the embodiments include these and other modifications and variations as coming within the scope and spirit of the invention.

In general, embodiments is disclosed directed to a system and method that can percutaneously block nerve conduction at a target nerve (e.g., a peripheral nerve such as the saphenous nerve, femoral nerve, pudendal nerve, brachial plexus nerves, radial nerve, median nerve, ulnar nerve, tibial nerve, sciatic nerve, ilioinguinal nerve, intercostal nerve, occipital nerve, suprascapular nerve, axillary nerve, lateral femoral cutaneous, lateral pectineal nerve, or the pelvic nerve), as well as the enteric nerve, the autonomic nerve, and the cranial nerve, e.g., to inhibit pain sensation, using electrical stimulation from a percutaneous lead placed in parallel, or substantially in parallel, and without direct contact, to a long axis of the peripheral nerve over an overlapping nerve region of greater than about 3 millimeters. The electrical stimulation can be delivered with a ramp that does not elicit sensations corresponding to onset activity.

The system includes, in some embodiments, one or more percutaneous electrodes integrated in a percutaneous lead and an electronic control system electrically attached to each electrode. The electronic control system delivers electrical stimulation to the target nerve either via a constant direct current waveform or via an alternating current stimulation waveform. The intensity of the electrical stimulation (e.g., the maximum or average output of the electrical stimulation) can be established based on a selection by the patient being treated or by a medical professional monitoring the treatment. When high-frequency stimulation is used, the delivered stimulation has a frequency that is greater than about 1.5 kilohertz and less than about 100 kilohertz. Changes to maximum intensity levels (or either a DC or high-frequency AC output) may be effectuated with a ramp rate of less than about 2 milliamps/second. The ramp gradually increase or decrease an intensity at which the electrical stimulation is delivered until a specified or desired stimulation intensity is reached. High frequency stimulation waveform may include a purely or predominantly sinusoidal waveform, square waveform, triangular waveform, sinc waveform, chirp waveform, noisy waveform, or any other structured or unstructured waveform having a pre-defined frequency distribution. Noisy waveform may have a pre-defined distribution such as Gaussian frequency distribution, exponential distribution, and etc.

Specifically, the system can include a waveform generator (e.g., electrical stimulator) to deliver electrical energy to a target nerve or target nerve tissue through a percutaneously-placed lead and electrode. The waveform generator may be embodied in a handheld or portable device that can be easily manipulated to deliver the therapy. The waveform generator may be embodied in an implantable device. The waveform generator and leads may be either reusable or disposable.

Example System #1

FIG. 1 is a diagram of an exemplary electrical stimulation system 102 configured to deliver electrical stimulation 114 from a percutaneous lead 104 comprising one or more percutaneous electrode(s) 106 placed in parallel, or substantially in parallel, and without direct contact, to a long axis 108 of a target nerve 110 over an overlapping nerve region 112 of greater than about 3 millimeters, to block nerve conduction through the overlapping nerve region 112, in accordance with an illustrative embodiment. This overlapping nerve region 112 is also referred to herein as a point of nerve conduction block 112. A percutaneous electrode 106 does not have to directly contact the nerve trunk, e.g., the epineurium, though it can, and the electrode and its associated assembly can be offset from the nerve trunk by up to 15 millimeters. The intensity or power of the electrical stimulation may be adjusted to compensate for individual patient perception of pain as well as for percutaneous electrode 106 placement and proximity to the nerve trunk of interest.

The electrical stimulation 114 can be delivered as a direct current stimulation (also referred to herein as DC stimulation) or as a charged-balanced high-frequency stimulation (also referred to herein as high-frequency electrical stimulation). The delivered electrical stimulation causes electrode surfaces to be charged or powered such that electrical charge are deposited on the electrodes and effect the movement of ions in the body. Generally, no electrical current (e.g., via electrons) leaves the electrodes and passes through the tissue.

Figure 3:
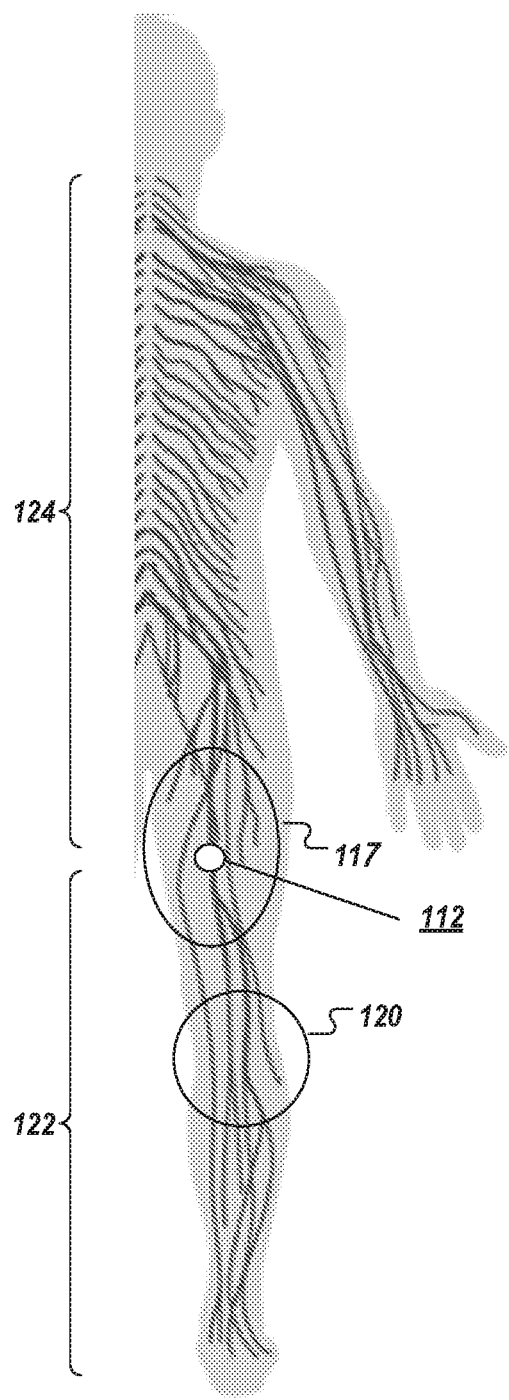
FIG. 3 is a diagram illustrating a method of treatment of pain, in accordance with an illustrative embodiment.

The electrical stimulation as applied to the overlapping nerve region 112 at a treatment site 117 can prevent an action potential from conducting across the point of nerve conduction block 112. Indeed, the point 112 of nerve conduction block (see also FIG. 3 in which a treatment is performed at the mid-thigh saphenous nerve, e.g., to treat post-surgical knee pain) can be used to inhibit and/or cease the sensation of pain by a patient or subject 118 at regions 120 (see FIG. 3) of the body proximal 122 to the point 112 of the nerve conduction block. Because action potentials are arrested at the point 112 of treatment, the treatment does not produce any discomfort that can be attributed to nerve conduction (as there is not any) while also preserves the ability of the patient to sense at regions 124 (see FIG. 3) distal to the point 112 of the nerve conduction block and that regions downstream to the point 112 that are served by a different sensory nerve other than the target nerve.

When high-frequency stimulation is delivered, the high-frequency stimulation may have a frequency component (e.g., one or more primary harmonics) in the range between about 1.5 kHz and about 100 kHz. In some embodiments, the high-frequency electrical stimulation has a frequency component (e.g., any harmonics) in the range between about 1.5 kHz and about 15 kHz. In some embodiments, the high-frequency electrical stimulation has a frequency component (e.g., any harmonics) in the range between about 1.5 kHz and about 25 kHz. In some embodiments, high-frequency electrical stimulation has any frequency component (e.g., any harmonics) in the range between about 1.5 kHz and about 50 kHz. In some embodiments, high-frequency electrical stimulation has any frequency component (e.g., any harmonics) in the range between about 1.5 kHz and about 75 kHz.

The high-frequency stimulation may be a charged-balanced sinusoidal waveform. In other embodiments, the high-frequency stimulation has other shaped waveforms, e.g., triangular waveform, a square waveform, sinc waveform, a rectangular waveform, a noisy waveform (e.g., an unstructured waveform having a pre-defined frequency distribution), or a chirp waveform. In some embodiments, the high-frequency stimulation includes multiple phases.

Referring still to FIG. 1, in some embodiments, a long axis 115 of the electrode 106 is placed in parallel, or substantially in parallel to the overlapping nerve region over a distance selected from the group consisting of greater than about 4 millimeters (mm), greater than about 5 mm, greater than about 6 mm, greater than about 7 mm, greater than about 8 mm, greater than about 9 mm, greater than about 1 centimeter (cm), greater than about 2 cm, greater than about 2.5 cm, greater than about 3 cm, greater than about 3.5 cm, greater than about 4 cm, greater than about 4.5 cm, greater than about 5 cm, greater than about 5.5 cm, greater than about 6 cm, greater than about 6.5 cm, greater than about 7 cm, greater than about 7.5 cm, greater than about 8 cm, greater than about 8.5 cm, greater than about 9 cm, greater than about 9.5 cm, and up to about 10 cm.

The percutaneous electrode 106 may be delivered, via an interventional procedure, and secured at a treatment site to manage pain associated with a surgical procedure (e.g., acute pain) or a diagnosed chronic pain. The percutaneous electrode 106 may be delivered at the treatment site via a procedure immediately following the surgical procedure. Though shown to be completely located beneath the skin, the percutaneous electrode 106 may have a length that allows it to extend from its intended placement location (e.g., next to and parallel to a target nerve) to terminate at a location outside the body (see, e.g., FIGS. 10, 13).

Referring still to FIG. 1, the percutaneous lead 104, in some embodiments, includes one or more return anodic electrodes 116 (e.g., as a bipolar lead) that are disposed, or affixed, beneath the skin or on the surface of the skin. In other embodiments, the percutaneous leads is configured as a monopolar lead in which a separate return electrode is placed, e.g., at a surface location on the skin where the lead wires are secured. In some embodiments, a patch used to secure the lead wires on the surface location also serves as the return electrode. Indeed, the exemplary methods can be performed using existing percutaneous leads. Examples of percutaneous leads that can be used to place an electrode in parallel, or substantially in parallel, to a target nerve includes the Octrode (St. Jude Medical) and InterStim (Medtronic), and the like, among others. The instant disclosure also provides for several embodiments of percutaneous leads that are suitable to do the same. The exemplary percutaneous leads may be specially configured to beneficially improve block efficacy in the exemplary placement configuration (e.g., in the parallel, or substantially parallel orientation to the target nerve), to improve reliability of insertion into the exemplary placement configuration, to improve titratability, to improve and/or provide reduced onset response and co-excitation, and/or to improve insertion and retention in the exemplary placement configuration.

Referring still to FIG. 1, the exemplary electrical stimulation system 102 is configured as an external signal generator that is electrically and physically coupled, via a cable 126 (show as 126a, 126b, 126c) to lead 104 carrying the electrodes 106. One of the electrode 106 provides electrical stimulation to the target tissue and the other electrode 116 provides a return path for the stimulation. The cable(s) 126 may have one or more conductors encapsulated therein and may include separate distinct cables to each carry the electrical stimulation as well as feedback signals or may include a single combined cable that comprises internal cables for the electrical stimulation and feedback signals.

The exposed electrode(s) 106 of a given percutaneous lead 104 may be inserted into the tissue at a distance of about 0.5 millimeters to about 15 millimeters from the target nerve, e.g., a distance from about 0.75 millimeters to about 10 millimeters, a distance from about 1 millimeter to about 5 millimeters. In some embodiments, the exposed electrodes are located only at a tip of the percutaneous lead. In other embodiments, the exposed electrodes are located at multiple locations at the tip region of the percutaneous lead. In some embodiments, the exposed electrodes are located at multiple locations that runs along a longitudinal length defining a percutaneous lead (e.g., where the percutaneous lead is shaped as a cuff or paddle).

As shown in FIG. 1, the exemplary electrical stimulation system 102 includes an electrical-stimulation generator 128 and one or more power source 130 that are each housed in a carrier 132 (e.g., housing). The electrical-stimulation generator 128 is configured to generate an electrical waveform output defining the electrical stimulation. In some embodiments, the electrical-stimulation generator 128 is configured to deliver a high-frequency stimulation. In other embodiments, the electrical-stimulation generator 128 is configured to deliver direct current stimulation. The one or more power sources 130 provide power for the electrical stimulation and, in some embodiments, for the underlying controls and electronics of the exemplary portable electrical stimulation system 102. In some embodiments, the power sources 130 include a second energy storage modules configured to provide energy while a first energy storage is replaced in a hot-swap operation.

Referring still to FIG. 1, the exemplary electrical stimulation system 102 includes a controller 134 that directs the operation of the electrical-stimulation generator 128 and provides the user interface 136 (shown as "input/output" 136a and "display" 136b). The user interface 136, in some embodiments, is configured to receive inputs from the patient or healthcare professional in which the input include, e.g., a selected intensity or power level from a set of pre-defined selectable intensity/power output levels. The controls may be based on a selected power level, current level, voltage level, intensity level, or based on a percentage of the maximum power output, maximum current output, maximum voltage output, maximum intensity output, and etc. The user interface 136, in some embodiments, further includes a display (136b) to provide indication of system on/off status, electrical stimulation on/off status, signal delivery output (e.g., power level, intensity output, etc.), system status, battery storage status (e.g., remaining battery capacity, low/high battery status, etc.), to the user regarding the electrical stimulation system 102. In some embodiments, the user interface 136 includes an audio output for indication of an alert or alarm condition or state. In some embodiments, the user interface 136 includes a communication port to external devices, such as a tablet, mobile computing device, desktop computing device, etc., to set schedules for the electrical-stimulation generator 128, and track usage of the electrical stimulation system 102 (e.g., power settings of the electrical stimulation).

Example System #2

Implantable Stimulator

Figure 2:
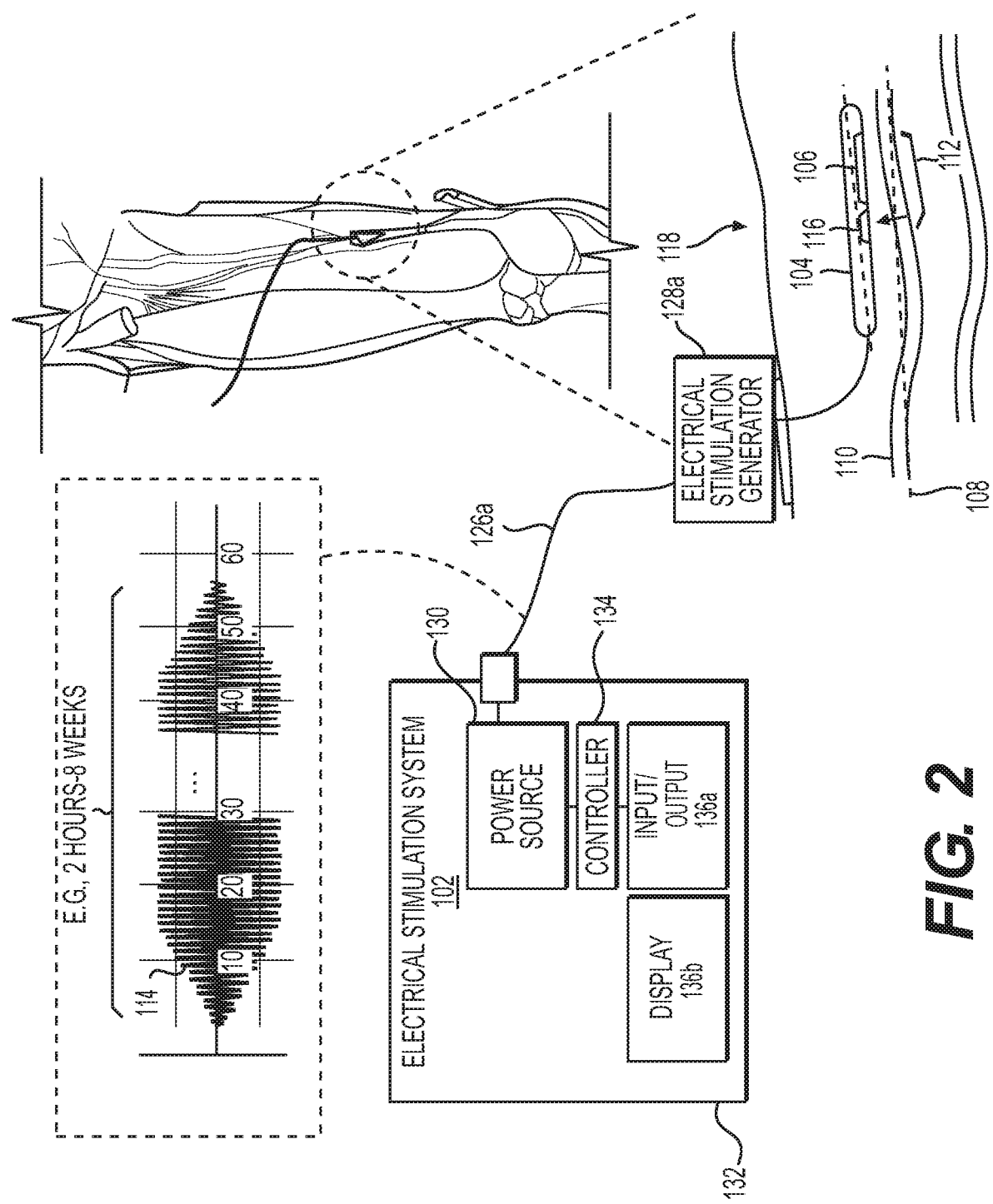
FIG. 2 is a diagram of another exemplary electrical stimulation system configured to deliver electrical stimulation from a percutaneous leads comprising one or more percutaneous electrode(s) placed in parallel, or substantially in parallel, and without direct contact, to a long axis of a target nerve over an overlapping nerve region of greater than about 3 millimeters, to block nerve conduction through the overlapping nerve region, in accordance with an illustrative embodiment.

FIG. 2 is a diagram of another exemplary electrical stimulation system 102a configured to deliver electrical stimulation (114) from a percutaneous leads 104 comprising one or more percutaneous electrode(s) 106 placed in parallel, or substantially in parallel, and without direct contact, to a long axis 108 of a target nerve 110 over an overlapping nerve region 112 of greater than about 3 millimeters, to block nerve conduction through the overlapping nerve region 112, in accordance with an illustrative embodiment.

Rather than an external electrical stimulator 128, the electrical stimulation system 102a includes an implantable stimulator 128a that can be placed on, or under, the skin of the patient 118.

Method of Treatment By Placement of Percutaneous Electrode in Parallel Orientation to a Target Nerve In another aspect, a method of treatment is provided to place a percutaneous lead at a treatment site of a subject to block nerve conduction at the treatment site via an electrical stimulation.

Figure 4A:
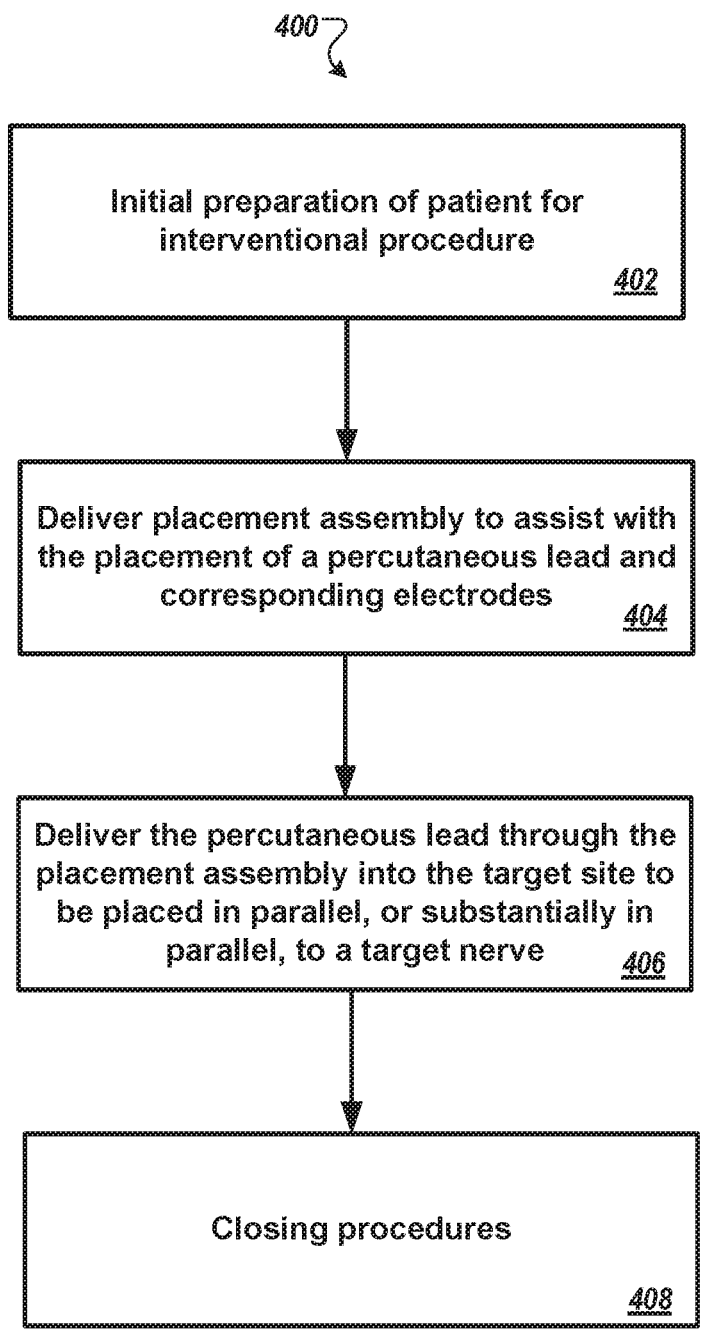
FIG. 4A is a diagram illustrating a method of placing a percutaneous lead at a treatment site of a subject to block nerve conduction at the treatment site via an electrical stimulation in which an electrode of the lead is placed in parallel, or substantially in parallel to a long axis of a target nerve over an overlapping nerve region of greater than about 3 millimeter, in accordance with an illustrative embodiment.

FIG. 4A is a diagram illustrating a method 400 of placing a percutaneous lead at a treatment site of a subject to block nerve conduction at the treatment site via an electrical stimulation in which an electrode of the lead is placed in parallel, or substantially in parallel to a long axis of a target nerve over an overlapping nerve region of greater than about 3 millimeter, in accordance with an illustrative embodiment. The method 400 may be performed without an open surgical procedure.

The method 400 includes, in some embodiments, an initial preparation (step 402) of the patient for the interventional procedure. The initial preparation step may include pre-op preparation for the stimulator, percutaneous lead, and return electrode as well as grounding the patient via application of a grounding electrode to the surface of the skin.

In some embodiments, the percutaneous lead is configured to operate with a central stylet that is inserted into a lumen of the percutaneous lead to stiffen the lead for insertion into the treatment site. The percutaneous lead may be assembled, in some embodiments, with the central stylet during the pre-op preparation. In other embodiment, the percutaneous lead is provided pre-assembled with the central stylet.

The initial preparation may include imaging the region of interest, e.g., via ultrasound imaging, to identify the target nerve and the nerve region to block nerve conduction. With ultrasound imaging, the oblique view may be first used. The initial preparation step may include inserting needle to deliver a local anesthetic along the anticipated lead insertion path.

The method 400 may then include delivering (step 404) a placement assembly to assist with the placement of the percutaneous lead and corresponding electrodes. The placement assembly, in some embodiments, is configured to receive a percutaneous lead inserted into an entry port of the placement assembly (e.g., a needle, introducer, or sheath) in which the percutaneous lead is placed at a first angle of insertion as defined with respect to an associated surface of the treatment site. The placement assembly then directs the percutaneous lead to a second angle that is parallel, or substantially parallel, to a long axis of a peripheral nerve to place the percutaneous lead over an overlapping nerve region of greater than about 3 mm. The first angle of insertion, in some embodiments, is between about 10 degrees and about 90 degrees with respect to the surface of the skin. In other embodiments, the first angle of insertion is between about 25 degrees and about 60 degrees, e.g., about 30 degrees. In some embodiments, the placement assembly is a needle. In other embodiments, the placement assembly is a Tuohy needle. In other embodiments, the placement assembly is an introducer. In some embodiments, the practitioner may ask the patient to provide an initial pain score associated with the pain area downstream to the treatment site.

In some embodiments, the method step 404 includes positioning the placement assembly (e.g., a curved Tuohy) into a target site while guided by ultrasound imaging. The placement of the placement assembly may include inserting the placement assembly into the target set and connecting the placement assembly to a stimulator (e.g., a signal waveform equipment that is used for this part of the procedure). The method step 404 may then include stimulating the placement assembly to stimulate the target nerve to confirm placement and directing the distal end of the placement assembly in an orientation parallel to the target nerve. Indeed, the electrical stimulation through the needle (i.e., placement assembly) is only used to guide the needle placement. In some embodiments, the practitioner may ask the patient to provide a pain score associated with the treatment site.

The method 400 includes delivering (step 406) a percutaneous lead through the placement assembly into the target site. The step of delivering the percutaneous lead may include placing the distal end of the percutaneous lead into the placement assembly and advancing the lead to a first lead marker indicated on the percutaneous lead. The step 406 may then include re-orienting the ultrasound imager to image the regions parallel to the target nerve and then advancing the percutaneous lead to a specified or desired distance, e.g., up to a second lead marker indicated on the percutaneous lead. Indeed, the stylet as inserted, or fixed, inside the percutaneous lead may provide stiffness to the structure of the percutaneous lead to facilitate its insertion into the tissue. In some embodiments, the practitioner may ask the patient to provide an updated pain score associated with the pain area downstream to the treatment site and/or of the treatment site.

The method 400 then includes closing procedures (step 408). The closing procedure may include removing the needle, stylet, needle, connection, and initial ground pad. Indeed, the stylet may be released from the locked state to be removed from the percutaneous lead. The closing procedure may include connecting the electrical connection of the percutaneous lead to a stimulator (e.g., a portable stimulator). The stimulator may be activated to confirm placement location. In some embodiments, the practitioner may ask the patient to provide a pain score associated with the pain area downstream to the treatment site.

The percutaneous lead may be used to deliver additional local anesthetic to the tip area of, or other areas along, the percutaneous lead. Indeed, a syringe may be connected to a connector of the percutaneous lead to deliver the local anesthetic to the lead. The treatment site may then be bandaged and the treatment site closed. The practitioner may provide instructions on the operation of the stimulator and initiate delivery of the electrical stimulation, e.g., to treat the pain.

In some embodiments, the placement assembly is configured (e.g., suitably dimensioned and shaped) to be placed proximal to the mid-thigh saphenous nerve block, e.g., to treat post-surgical knee pain.

FIG. 4B is a diagram of an example placement assemblies (e.g., 420, 440) that may be used to deliver the percutaneous lead to the treatment at an orientation parallel, or substantially parallel, to the target nerve, in accordance with an embodiment. The first example placement assembly 420 is shown as a fixed-angle introducer having a gradual bend.

The second example placement assembly 440 is also shown as a fixed-angle introducer having a sharper bend and a shorter arc length as compared to the first placement assembly 420. Indeed, either example placement assemblies may be used to deliver the percutaneous lead to the treatment at intended or specified orientation.

In some embodiments, the placement assembly comprises an introducer subsystem configured to orient the electrode(s) parallel to the nerve. The placement assembly may include a tip that facilitate advancement of the introducer into the tissue without the need of fluid injection, or other methods, to pre-open a space in the tissue to provides for passage of the percutaneous lead. The tip, or other portion, of the placement assembly may be conductive to facilitate application of an electrical stimulation to confirm placement of the placement assembly. Introducer subsystem includes, in some embodiments, a needle and an introducer. The needle can be removed from the introducer through which the percutaneous lead insertion can occur. The tip of the introducer may be angled with respect to the entry port to redirect the initial percutaneous lead insertion from the initial angle to a redirected angle between 10° and 90°, more specifically 25°-60°, for example 30°, to facilitate turning the electrodes to be parallel to the nerve.

In some embodiments, the redirection is caused by use of a needle or introducer with a fixed tip curve.

In other embodiment, the redirection is caused by use of a sheath that is inserted through or around a straight needle/introducer. The sheath assumes a bent shape once the needle/introducer is retracted.

In yet another embodiment, the redirection is via use of a needle/introducer which can be reversibly bent.

The placement assemblies and/or percutaneous leads may be provided in a kit for an electrical nerve block procedure. The kit may provide for articles and/or components depicted in FIGS. 1 through 15. In some embodiments, the kit includes ECG and EMG electrodes may be included in the kit.

The kit may include a container that may be, for example, a suitable tray having a removable sealed covering in which the articles are contained. In some embodiments, the kit may include drape, site dressings, tape, skin-markers. The kit, in some embodiments, may additionally include one or more containers of electrically conductive liquids or gels, antiseptics, and/or skin-prep liquids. The kit may include pre-packaged wipes such as electrically conductive liquid or gel wipes, antiseptic wipes, or skin-prep wipes. The kit may contain medicinal liquids and/or electrolytic solutions (e.g., the electrolytic solution may be or may include a bioresorbable gel material that is injected in liquid form but becomes substantially viscous or even solid-like after exiting the openings in the percutaneous electrode). In some embodiments, the kit includes a portable stimulator system 102 and corresponding cables 126.

Percutaneous Lead

In another aspect, several percutaneous lead designs are disclosed each having features that facilitate the improved insertion of the percutaneous lead in an intended orientation, parallel, or substantially in parallel, to a long axis of a target nerve. The percutaneous lead may be inserted through an introducer/needle.

To assist in advancing the percutaneous lead into the target tissue space parallel to the target nerve, the percutaneous lead includes, in some embodiments, a removable stylet (e.g., a removable central stylet) that is inserted into a central region of the percutaneous lead to support, i.e., stiffen, the percutaneous lead during the insertion procedures. In some embodiments, the percutaneous lead is configured with a stiffness that facilitates advancement of the lead in to the target tissue space parallel to the target nerve for a distance of up to 10 cm out of the needle. In some embodiments, the percutaneous lead has a stiffness that facilitates advancement of the lead in to the target tissue space for a distance of up to 4 cm out of the needle. In some embodiments, the percutaneous lead has a stiffness that facilitates advancement of the lead in to the target tissue space for a distance of up to 3 cm out of the needle.

In some embodiments, the central stylet has a diameter between about 0.008" and 0.010". The central stylet may be made of stainless steel, tungsten, titanium, carbon, or other suitable medical grade material. The central stylet may be reversibly or irreversibly locked to the percutaneous lead to facilitate insertion.

In some embodiments, the percutaneous lead includes a clamp to reversible lock with the central stylet. The clamp creates friction between a lead lumen and the stylet. In some embodiments, the central stylet includes the clamp.

Alternatively, or in combination with, the percutaneous lead includes metal reinforcement of the electrode body to provide the desired stiffness to advance the lead in to the target tissue space parallel to the target nerve for a distance of up to 10 cm out of a needle.

Percutaneous Lead Example #1

Figure 5:
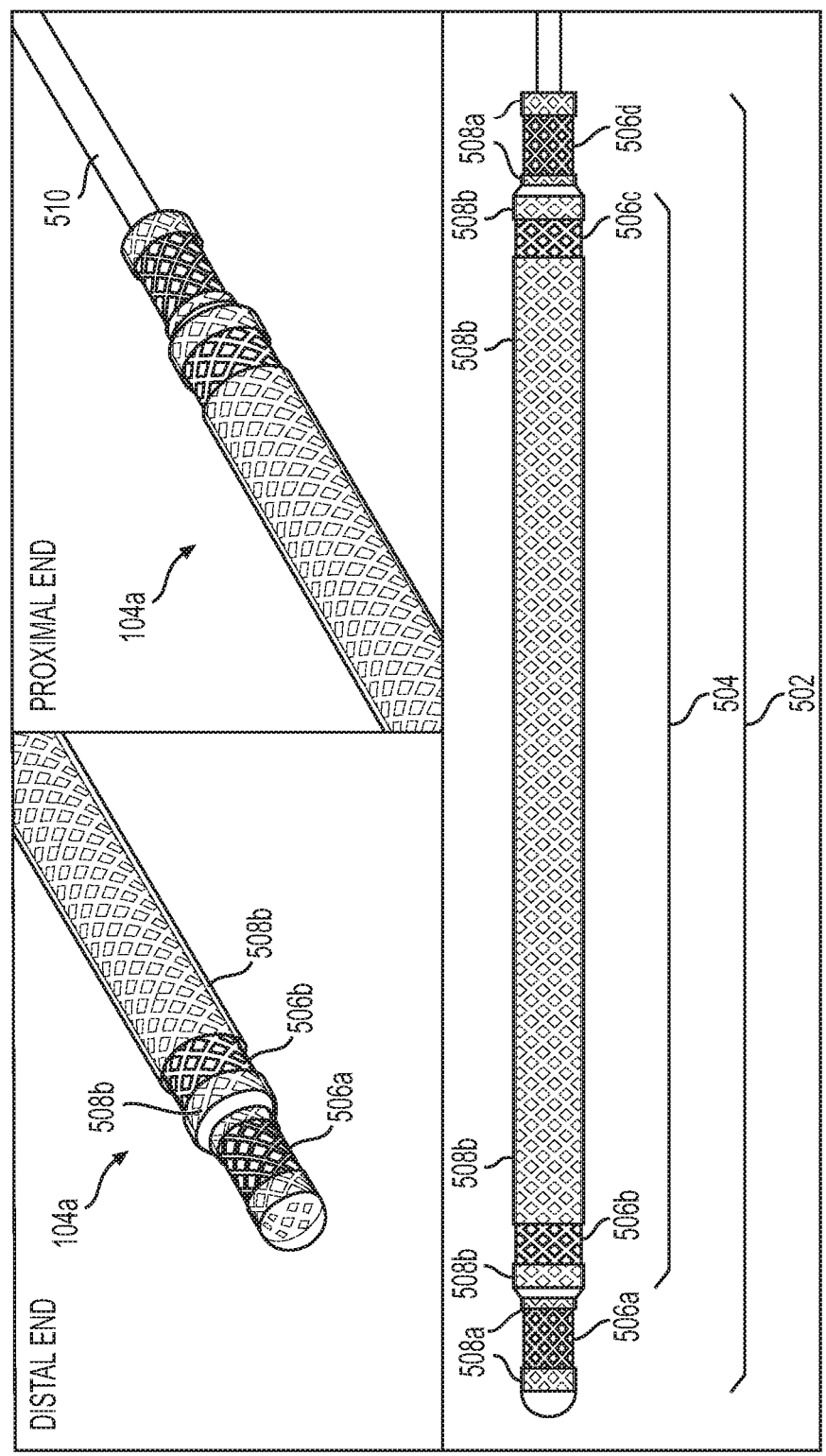

FIGS. 5, 6, 7A, 7B, 8A, and 8B are schematics of a percutaneous lead 104 (shown as 104a) configured with braided electrodes to be delivered parallel, or substantially in parallel, to a long axis of a target nerve, in accordance with another illustrative embodiment. The percutaneous lead 104a may be configured with one or more tube members (FIG. 5 shows two tube members 502, 504) in which each tube members (e.g., 502, 504) includes an inner conductive layers 506 (shown as 506a, 506b) that is partially or completely surrounded an external insulated layer 508 (shown as 508a, 508b) to form an electrode pair. The inner conductive layer 506 and outer insulated 508 are configured as coaxial tubes, in some embodiments, with one electrode-contact pair formed per tube. In other embodiments, only a single electrode-contact is formed per tube. In yet other embodiments, the inner conductive layer 506 and outer insulated 508 are configured to form multiple electrode regions. The inner conductive layers 506 (shown as 506c, 506d) are exposed, in some embodiments, at a distal end of the percutaneous lead 104a to provide location for electrical contact and connection to a stimulator system (e.g., 102, 102a). In some embodiments, the longitudinal body of the percutaneous lead 104 has a length sufficient to allow placement of the electrodes of the lead 104 (and associated electrodes 106) in the parallel orientation to the target nerve and to provide access for electrical connection to the contacts (e.g., 506c and/or 506d) outside the body. In other embodiments, the inner conductive layers 506 of each of the tube members are coupled to a lead-wire (not shown) that provide electrical connection to the contacts.

Insulation of the wire tube may occur through insulation of individual wire(s), or by embedding the conductive tubing in insulated tubing. In some embodiments, each individual wire may be encapsulated to form the inner conductive layer 506 and outer insulated 508. In other embodiments, a single outer insulated 508 is encapsulated over a coiled inner conductive layer 506.

Wires may be close-packed, with no space between coils (e.g., a closed coil), or open, with a space between adjacent coils (e.g., with uniform or non-uniform spacing between adjacent coils) along the length of the lead to enable, for example, as anti-migration measures or ultrasound visibility.

In some embodiments, the percutaneous lead 104a forms a full braid assembly comprising a longitudinal body that includes two or more coaxial conducting members in which each member includes multiple conductors (e.g., steel ribbon, carbon ribbon, platinum ribbon, carbon, etc.) interlaced and formed into a mesh tube embedded in a polymer and in which each tube has one or more exposure regions defined by the polymer.

Indeed, the percutaneous lead 104a may form two or more electrodes configured to operate in bipolar fashion in which at least one of the electrode serves as the cathode and another electrodes serves as the return anode. In other embodiments, the percutaneous lead 104a forms a single electrode with an electrical return being provided through a surface electrode placed on the skin. In yet another embodiment, the percutaneous lead 104a is configured with or more than two electrodes to operate in a multipolar operation. The multiple electrodes may be used for electrode positional tuning and/or current steering.

Referring still to FIG. 5, the conductive material of the inner conductive layer 506a, in some embodiments, forms one or more electrode site(s) 106 (shown as 506a, 506b) intended to reside parallel to the target nerve to deliver electrical therapy. The external insulated layer 508 (e.g., 508a, 508b) encapsulates the inner conductive layer 506 (e.g., 506a, 506b) and includes openings to expose the portions of the inner conductive layer 506a, 506b that define the electrodes.

Tubes (e.g., 502, 504) may comprise coiled wire(s) with a specified wire count and/or coil pitch, formed into a tube of a given inner and outer diameter. The wires may be flat or rounded. Coiled wires may be crossed over one another to form a braided mesh. In other embodiments, a braided mesh is formed as a single unitary structure that is affixed to the tube.

In some embodiments, the conductive material is exposed at contact site(s) (e.g., 506c, 506d) residing outside the body of the patient and connect to cabling that transmits the treatment waveform from a waveform generator to the implanted electrode(s).

Referring still to FIG. 5, the percutaneous lead 104a is configured with a continuous individual electrodes. In other embodiments, the percutaneous lead 104a is configured with multiple electrode segments in which the segments have a specified length and distance between them. For example, an electrode comprising of 3 segments may have an electrode length of 1 mm each in which each is separated by space of 4 mm to provide a lead length of about 11 mm.

The percutaneous lead 104a may be configured with an electrode length between about 1 mm and about 10 cm, e.g., between about 3 mm and about 10 mm. For multiple electrodes on the lead body, the electrodes may be separated by a space of 1 mm to 10 cm, for example 10 mm.

Referring still to FIG. 5, the inner conductive layer 506 (e.g., of layers 502 or 504) may be made of a metal such as 304 or 316 stainless steel, platinum, carbon, and other suitable medical-grade electrode material, and the outer insulated 404 is made of a polymer such as polyimide, Pebax®, other suitable medical-grade insulators.

Referring still to FIG. 5, the distal end of the percutaneous lead 104a includes a ball tip 512. The ball tip 512 facilitates advancement of the percutaneous lead 104a into the tissue by minimizing the likelihood of it piercing and/or damaging a blood vessel or nerve trunk.

The percutaneous lead 104a includes a central stylet 510 that stiffens the elongated wall of the percutaneous lead (e.g., the first and second members 502, 504). In some embodiments, the central stylet 510 is fixably connected into a lumen of the percutaneous lead 104a (e.g., the inner surface of the first member 502). In other embodiments, the central stylet 510 is removable having a clamp that fixes the central stylet 510 to the lumen of the percutaneous lead 104a (e.g., the inner surface of the first member 502) when engaged.

FIG. 6 shows a schematic view of the assembled braided percutaneous lead 104a of FIG. 5, in accordance with an illustrative embodiment. This percutaneous lead 104a may be dimensioned for placement next to the saphenous nerve as well as other peripheral nerves discussed herein. FIGS. 7A, 7B, 8A and 8B each shows schematic views of components of the braided percutaneous lead 104a of FIG. 6, in accordance with an illustrative embodiment. Indeed, the percutaneous lead 104a may be dimensioned with other suitable lengths and dimensions for other types of peripheral and target nerves discussed herein.

Referring to FIG. 7A, the braided percutaneous lead 104a of FIG. 6 includes a first tube member 502 formed of an inner conductive layer 506a and an outer insulated layer 508a. The first tube member 502 is hollow, forming a lumen 706 for insertion of the central stylet 510 (see FIG. 5) and/or for delivery of fluids to the tip of the percutaneous lead 104a. The outer insulated layer 508a includes one or more opening regions 702 that each exposes the portions of inner conductive layer that form the electrode(s) 506a or contact(s) 506c for the lead 104a.

Referring to FIG. 8A, the braided percutaneous lead 104a of FIG. 6 includes a second tube member 504 also formed of an inner conductive layer 506b and an outer insulated layer 508b. The second tube member 504 is concentrically placed over the first tube member 502 to form the braided percutaneous lead 104a. The second tube member 504 is also hollow, forming a lumen 806 for placement of the first tube member 502. The outer insulated layer 508b includes opening regions 802 that exposes the portions of inner conductive layer that form another set of electrode(s) 506b or contact(s) 506d. The second tube member 504 has a length that covers, e.g., only a central longitudinal section 704 of the first tube member 502, or a portion thereof, to provide access to the electrode regions 702 of the first tube member 502.

Percutaneous Lead Example #2

FIGS. 9, 10, 11A, 11B, 12A, and 12B are schematics of a percutaneous lead 104 (shown as 104b) configured with coiled electrodes to be delivered parallel, or substantially in parallel, to a long axis of a target nerve, in accordance with another illustrative embodiment. The percutaneous lead 104b may be configured with one or more coiled members (FIG. 9 shows two coiled members 902, 904) in which each coiled members (e.g., 902, 904) includes an inner conductive layers 506 (shown as 506a, 506b) that is partially or completely surrounded an external insulated layer 508 (shown as 508a, 508b). The inner conductive layer 506 and outer insulated 508 are configured as coaxial tubes, in some embodiments, with one electrode-contact pair formed per tube. In other embodiments, only a single electrode-contact is formed per tube. In yet other embodiments, the inner conductive layer 506 and outer insulated layer 508 are configured to form multiple electrode regions. A single tube may include 2, 4, 8 wires, or any other number of wires.

Insulation of the wire tube may occur through insulation of individual wire(s), or by embedding the conductive tubing in insulated tubing. In some embodiments, each individual wire may be encapsulated to form the inner conductive layer 506 and outer insulated layer 508. In other embodiments, a single outer insulated layer 508 is encapsulated over a coiled inner conductive layer 506.

Wires may be close-packed, with no space between coils, or open, with a space between adjacent coils (e.g., with uniform or non-uniform spacing) along the length of the lead to facilitate, for example, anti-migration measures or ultrasound visibility.

In some embodiments, the percutaneous lead 104b forms a fully coiled assembly comprising a longitudinal body that includes two or more coaxial conducting members in which each member includes multiple conductors (steel wire) individually insulated and coiled into a tube, and each tube has one or more exposure regions defined by the wire insulation (and lack thereof). The percutaneous lead 104b may include a removable stylet/stiffening member passing through the central conducting member.

Indeed, the percutaneous lead 104b may form two or more electrodes configured to operate in bipolar fashion in which at least one of the electrode serves as the cathode and another electrodes serves as the anode. In other embodiments, the percutaneous lead 104b forms a single electrode with an electrical return being provided through a surface return electrode placed on the skin. In yet another embodiment, the percutaneous lead 104b is configured with or more than two electrodes to operate in a multipolar operation. The multiple electrodes may be used for electrode positional tuning.

Referring still to FIG. 9, the conductive material of the inner conductive layer 506a, in some embodiments, forms one or more electrode site(s) 106 (shown as 506a) intended to reside parallel to the target nerve to deliver electrical therapy. The external insulated layer 508 encapsulates the inner conductive layer 506 and includes openings to expose the portions of the inner conductive layer 506 that define the electrode(s) and the contact(s) for the lead 104b.

Tubes (e.g. 902, 904) may comprise coiled wire(s) with a specified wire count and/or coil pitch, formed into a tube of a given inner and outer diameter. The wires may be flat or rounded.

In some embodiments, the conductive material is exposed at contact site(s) residing outside the body of the patient and connect to cabling that transmits the electrical stimulation from a waveform generator to the percutaneous electrode(s).

Referring still to FIG. 9, the percutaneous lead 104b is configured with a continuous individual electrodes. In other embodiments, the percutaneous lead 104b is configured with multiple electrode segments in which the segments have a specified length and distance between them. For example, an electrode comprising of 3 segments may have an electrode length of 1 mm each in which each is separated by space of 4 mm to provide a lead length of about 11 mm.

The percutaneous lead 104b may be configured with an electrode length between about 1 mm and about 10 cm, e.g., between about 3 mm and about 10 mm. For multiple electrodes on the lead body, the electrodes may be separated by a space of 1 mm to 10 cm, for example 10 mm.

Referring still to FIG. 9, the inner conductive layer 506 (e.g., of layers 902 or 904) may be made of a metal such as 304 or 316 stainless steel, platinum, as well as carbon, or other suitable medical-grade electrode material, and the outer insulated 508 is made of a polymer such as polyimide, Pebax®, other suitable medical-grade insulators.

Referring still to FIG. 9, the distal end of the percutaneous lead 104b includes a ball tip 512. The ball tip 512 facilitates advancement of the percutaneous lead 104b into the tissue by minimizing the likelihood of it piercing and/or damaging a blood vessel or nerve trunk.

The percutaneous lead 104b includes a central stylet 510 that stiffens the elongated wall of the percutaneous lead (e.g., the first and second members 902, 904). In some embodiments, the central stylet 510 is fixably connected into a lumen of the percutaneous lead 104b (e.g., the inner surface of the first member 902). In other embodiments, the central stylet 510 is removable having a clamp that fixes the central stylet 510 to the lumen of the percutaneous lead 104b (e.g., the inner surface of the first member 902) when engaged.

FIG. 10 shows a schematic view of the assembled coiled percutaneous lead 104b of FIG. 9, in accordance with an illustrative embodiment. The percutaneous lead 104b may be dimensioned for placement next to the saphenous nerve. FIGS. 11A, 11B, 12A and 12B each shows schematic views of components of the coiled percutaneous lead 104b of FIG. 10, in accordance with an illustrative embodiment. Indeed, the percutaneous lead 104a may be dimensioned with other suitable lengths and dimensions for other types of peripheral and target nerves discussed herein.

Referring to FIG. 11A, the coiled percutaneous lead 104b includes a first tube member 902 formed of an inner conductive layer 506a and an outer insulated layer 508a. The first tube member 902 is hollow, forming a lumen 1106 for insertion of the central stylet 510 (see FIG. 5). The outer insulated layer 508a spans regions 1104 and includes one or more non-insulated regions 1102 that each exposes the portions of inner conductive layer that form the electrode(s) 506a and the contact(s) 506c for the lead 104b.

Referring to FIG. 12A, the coiled percutaneous lead 104b includes a second tube member 904 also formed of an inner conductive layer 506b and an outer insulated layer 508b. The second tube member 904 is concentrically placed over the first tube member 902 to form the coiled percutaneous lead 104b. The second tube member 904 is also hollow, forming a lumen 1206 for placement of the first tube member 902. The outer insulated layer 508b includes opening regions 1202 that exposes the portions of inner conductive layer that form another set of electrode(s) 506b and contact(s) 506d. The second tube member 904 has a length that covers, e.g., only a central longitudinal section 1104 of the first tube member 902, or a portion thereof, to provide access to the electrode regions 1102 of the first tube member 902.

Percutaneous Lead Example #3

Figure 13:
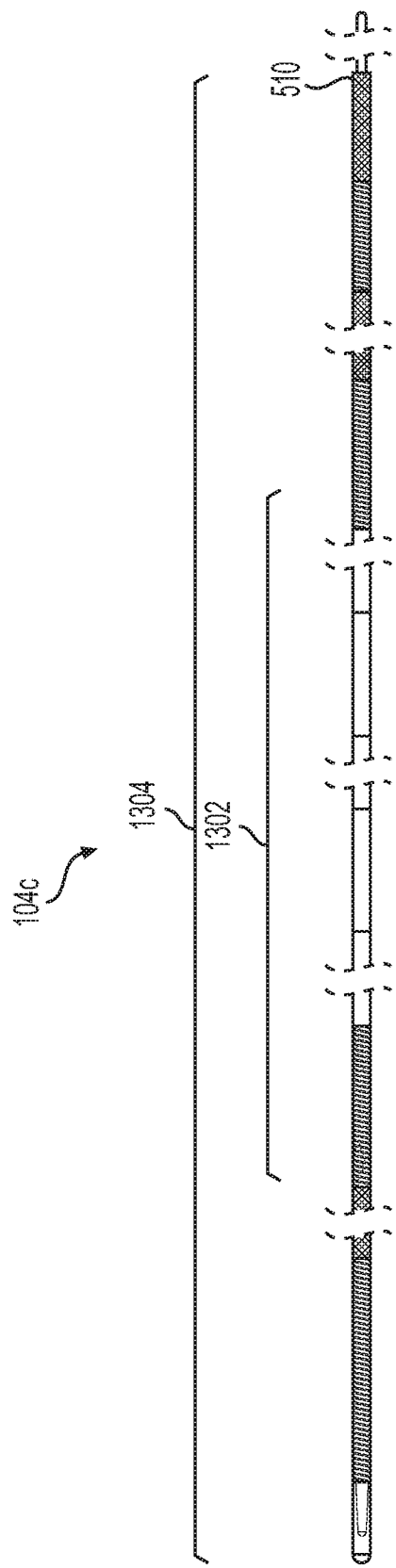
FIGS. 13, 14, 15 are schematics of a percutaneous lead configured with braided and coiled electrodes to be delivered parallel, or substantially in parallel, to a long axis of a target nerve, in accordance to another illustrative embodiment.
Figure 14:
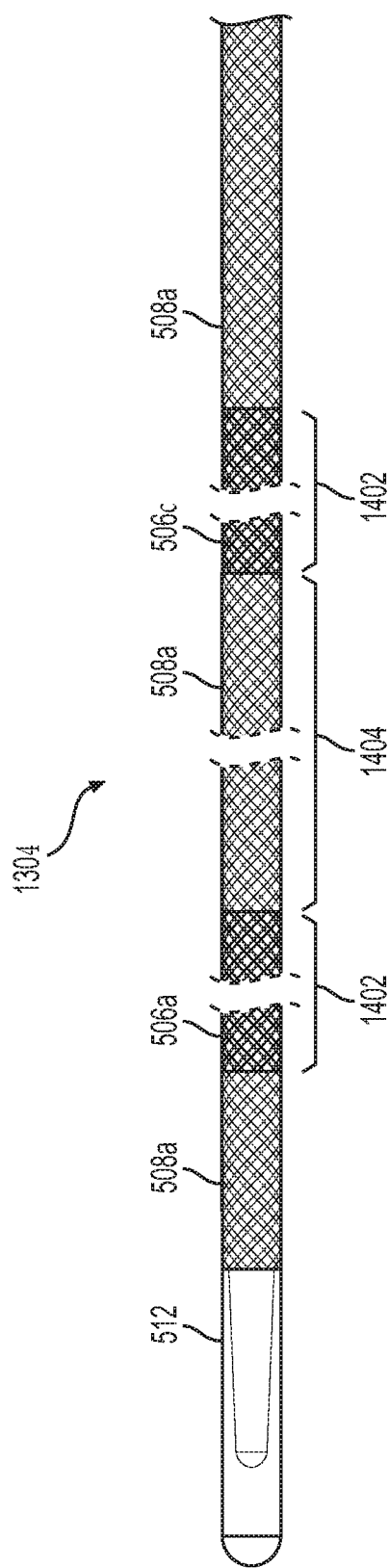
Figure 15:
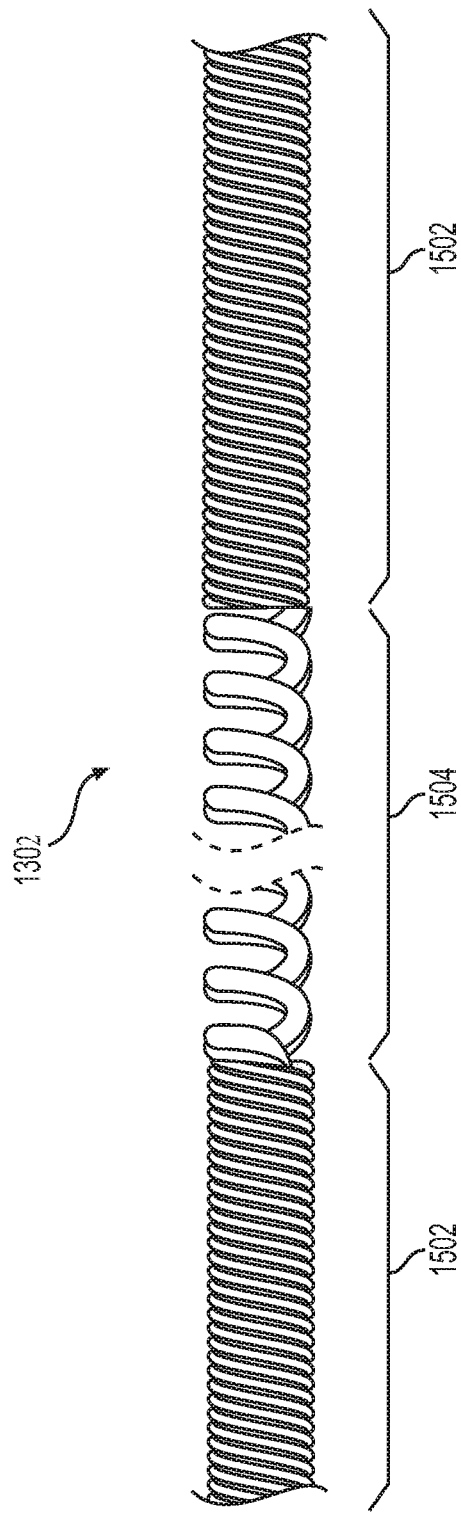
Figure 16:
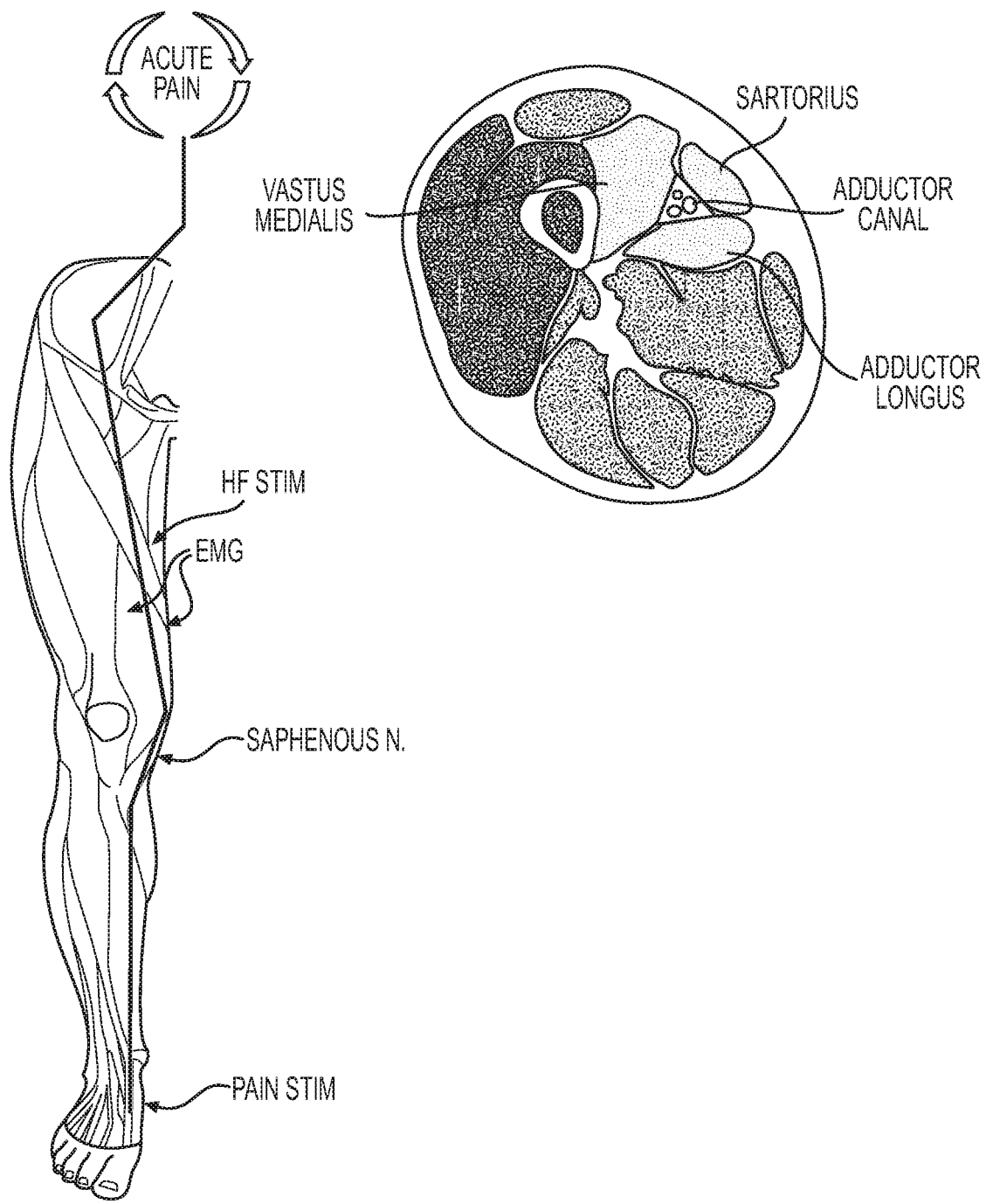

FIGS. 13, 14, and 15 are schematics of a percutaneous lead 104 (shown as 104c) configured with braided and coiled electrodes to be delivered parallel, or substantially in parallel, to a long axis of a target nerve, in accordance to another illustrative embodiment. The percutaneous lead 104c is a hybrid assembly that includes both a set of one or more braided electrodes (e.g., as discussed in relation to FIGS. 5-8) and a set of one or more coiled electrodes (e.g., as discussed in relation to FIGS. 9-12). In FIG. 13, the braided layer 1304 is shown as an inner tube and the coiled layer 1302 is shown as an outer tube. The percutaneous lead 104c may include two or more coiled layers 1302 (not shown). As noted above, wires may be close-packed, with no space between coils, or open, with a space between adjacent coils (e.g., with a uniform or non-uniform spacing) along the length of the lead to facilitate, for example, anti-migration measures or ultrasound visibility. A single tube, e.g., of braided layer 1304 may include 2, 4, 8 wires, or any other number of wires.

In some embodiments, the percutaneous lead 104*c* forms a longitudinal body comprising two coaxial conducting members in which the first member 1304 is formed, e.g., of a steel mesh tube (braid) and the second member 1302 is formed of a coil including having a region with an opened pitch.

Indeed, the percutaneous lead 104*c* may form two or more electrodes configured to operate in bipolar fashion in which at least one of the electrodes serves as the cathode and another electrodes serves as the anode. In other embodiments, the percutaneous lead 104*c* forms a single electrode with an electrical return being provided through a surface return electrode placed on the skin. In yet another embodiment, the percutaneous lead 104*c* is configured with or more than two electrodes to operate in a multipolar operation. The multiple electrodes may be used for electrode positional tuning.

Referring to FIG. 14, the conductive material of the inner conductive layer 506 (shown as 506*a*), in some embodiments, forms one or more electrode site(s) 106 intended to reside parallel to the target nerve to deliver electrical therapy. The external insulated layer 508 (shown as 508*a*) encapsulates the inner conductive layer 506 and includes openings to expose the portions of the inner conductive layer that define the electrodes (506*a*) and the contacts (506*c*) for the lead 106*c*. Tubes (1304, 1302) may comprise coiled wire(s) with a specified wire count and/or coil pitch, formed into a tube of a given inner and outer diameter. The wires may be flat or rounded. The coiled wires may have a pitch of zero or may have a pitch to provide for an open coil.

In some embodiments, the conductive material is exposed at contact site(s) residing outside the body of the patient and connect to cabling that transmits the treatment waveform from a waveform generator to the implanted electrode(s).

Referring still to FIG. 14, the percutaneous lead 104*c* is configured with a continuous individual electrodes. In other embodiments, the percutaneous lead 104*c* is configured with multiple electrode segments in which the segments have a specified length and distance between them. For example, an electrode comprising of 3 segments may have an electrode length of 1 mm each in which each is separated by space of 4 mm to provide a lead length of about 11 mm.

The percutaneous lead 104*c* may be configured with an electrode length between about 1 mm and about 10 cm, e.g., between about 3 mm and about 10 mm. For multiple electrodes on the lead body, the electrodes may be separated by a space of 1 mm to 10 cm, for example 10 mm.

Referring still to FIG. 14, the inner conductive layer 506 (e.g., of layers 1302 or 1304) may be made of a metal such as 304 or 316 stainless steel, platinum, as well as carbon, or other suitable medical-grade electrode material, and the outer insulated 508 is made of a polymer such as polyimide, Pebax®, other suitable medical-grade insulators.

Referring still to FIG. 14, the distal end of the percutaneous lead 104*c* includes a ball tip 512. The ball tip 512 facilitates advancement of the percutaneous lead 104*c* into the tissue by minimizing the likelihood of it piercing and/or damaging a blood vessel or nerve trunk.

The percutaneous lead 104*c* includes a central stylet 510 that stiffens the elongated wall of the percutaneous lead (e.g., the first and second members 1302, 1304). In some embodiments, the central stylet 510 is fixably connected into a lumen of the percutaneous lead 104*c* (e.g., the inner surface of the first member 1302). In other embodiments, the central stylet 510 is removable having a clamp that fixes the central stylet 510 to the lumen of the percutaneous lead 104*c* (e.g., the inner surface of the first member 1302) when engaged.

Referring still to FIG. 14, the braided-coiled percutaneous lead 104*c* includes a first tube member 1304 formed of an inner conductive layer 506 and an outer insulated layer 508. The first tube member 1302 is hollow, forming a lumen for insertion of the central stylet 510. The outer insulated layer 508*a* includes one or more opening regions 1402 that each exposes the portions of inner conductive layer that form the electrode(s) (506*a*) and contact(s) 506*c*

Referring to FIG. 15, the braided percutaneous lead 104*c* includes a coiled member 1302 that is concentrically placed over the first tube member 1304 to form the braided-coiled percutaneous lead 104*c*. The second coiled member 1302 is also hollow, forming a lumen for placement of the first tube member 1304. The outer insulated layer 508*b* includes a set of first coiled regions 1502 having a first coil spacing that forms a set of electrodes and/or contact(s) and a second coiled region 1504 to provide a region of compliance to facilitate flexing of the percutaneous lead 104*c*, e.g., with movement of the tissue.

The second coiled member 1302 has a length that covers, e.g., only a central longitudinal section 1404 of the first tube member 1304, or a portion thereof, to provide access to the electrode regions 1402 of the first tube member 1304.

Indeed, the percutaneous lead 104*c* may be dimensioned with other suitable lengths and dimensions for other types of peripheral and target nerves discussed herein.

Each of the percutaneous leads (e.g., 104*a*, 104*b*, 104*c*) may be configured to facilitate fluid delivery through the central lumen (e.g., 706 or 1106). The percutaneous leads (e.g., 104*a*, 104*b*, 104*c*) may have a central opening at the non-implanted end proximal to the contact(s) for connecting to a syringe or adapter or mode of fluid injection.

In some embodiments, the percutaneous lead (e.g., 104*a*, 104*b*, 104*c*) has a central opening or opening(s) along the wall of the distal end, near the implanted electrode(s), for delivery of fluid to the target area.

In some embodiments, the percutaneous lead (e.g., 104*a*, 104*b*, 104*c*) has markings along its length to indicate depth of insertion.

In some embodiments, the percutaneous lead (e.g., 104*a*, 104*b*, 104*c*) has markings at its distal (implanted) tip to indicate that its full length has been removed from the body after completion of treatment.

In some embodiments, the percutaneous lead (e.g., 104*a*, 104*b*, 104*c*) is connected to a cable adapter that enables transmission of the treatment waveform from a waveform generator to the electrode(s). A cable adaptor may have a clear window to allow visual confirmation that the lead contacts have properly aligned/connected to adaptor contacts. The cable adapter may have a port to facilitate fluid delivery through the lead after the lead has been connected to the adapter. The cable adapter may have features that facilitate one-handed connection between adapter and lead, for example, a rubber component configured to hold the lead near the contacts so that a lid-closing motion can seat the electrode contacts in the adapter contacts.

Experimental Results of Method of Treatment by Placement of Percutaneous Electrode in Parallel Orientation to a Target Nerve and Stimulation via High-Frequency Electrical Stimulation A human study was conducted to investigate the effects of high-frequency electrical stimulation delivered percutaneously to the saphenous nerve in the adductor canal on acute pain in able-bodied subjects without use of direct contact of the electrodes to the nerve trunk, e.g., via cuff electrodes. Though a cuff electrode can reduce postamputation pain, the surgical implantation of a nerve cuff can considerably burden the use of high-frequency stimulation for acute applications.

FIGS. 16, 17A, 17B, and 17C show experimental results of a percutaneous method of treating pain via percutaneous electrodes placed in parallel orientation to a target nerve and stimulated via high-frequency electrical stimulation, in accordance with an illustrative embodiment.

The study was performed on able-bodied human subjects (N=5) and underwent multiple trials of electrical stimulation. Acute pain sensations were elicited by transcutaneous electrical stimulation of the saphenous nerve at the ankle (see FIG. 16). High-frequency electrical stimulation comprising a 10 kHz sinusoidal wave was simultaneously delivered to electrodes placed generally in parallel to the saphenous nerve at the adductor canal (see FIG. 16) via a percutaneous lead. Various high-frequency stimulation amplitudes (all ≤25 mA) and durations (seconds-to-minutes) were used. Outcome measures including acute pain score and muscle activity were recorded. In the study, subjects described their pain intensity on a 0-to-10 scale via a handheld potentiometer, where 3 was defined as the pain-threshold. Muscle activity was monitored both visually and by EMG recordings.

FIGS. 17A, 17B, and 17C show results of the high-frequency electrical stimulation delivered percutaneously to the saphenous nerve in the adductor canal, in accordance with an illustrative embodiment. All subjects in the study reported reduced pain scores when high-frequency electrical stimulation was applied. Painful sensations were completely abolished in 4 subjects (with reference to graph 2A in FIGS. 17A-17C), and were still present, but reduced in 1 subject (with reference to graph 2B in FIGS. 17A-17C). In all subjects of the study, it was observed that pain scores returned to baseline values within seconds after the stimulation was terminated (FIGS. 17A-17C). High-frequency electrical stimulation was well tolerated by all subjects and did not elicit EMG activity or visible contractions of the thigh muscles. No serious adverse effects were reported.

The study demonstrates the efficacy of high-frequency electrical stimulation of the saphenous nerve via a percutaneous electrode placed generally in parallel to the saphenous nerve in blocking acute pain sensations that were elicited distally and without eliciting unwanted contractions of the nearby muscles. The study further shows that blocking effects were titratable and reversible.

Indeed, the study provides that percutaneous high-frequency electrical stimulation of a sensory nerve in the adductor canal, when delivered via percutaneous electrodes placed generally in parallel of the sensory nerve, can reversibly block acute pain sensations in humans.

Experimental Results of Method of Treatment by Placement of Percutaneous Electrode in Parallel Orientation to a Target Nerve and Stimulation via Direct Current Stimulation An animal study was conducted to investigate the effects of direct-current electrical stimulation delivered to a target neve. In this second study, nervous signaling was generated by stimulation of a sciatic nerve in an anesthetized rat, and the nervous signaling was blocked using direct current from electrodes placed inside the body and generally in parallel to the sciatic nerve.

In the animal study, a male rat was anesthetized using isoflurane (3%), shaved on both sides, and placed on its side. While under ongoing isoflurane anesthesia, the sciatic nerve was surgically exposed along a 30 mm length in the upper portion of the right hind limb. Bipolar hook electrodes were placed in contact with the nerve at the proximal-most position, with the cathode oriented distally (roughly 2 mm cathode-anode separation). Evoked electromyography (EMG) was recorded via multi-polar subdermal needle electrodes placed within the gastrocnemius muscle. The stimulation threshold for the direct motor component of the evoked EMG was found to be 2 V (50 µs square pulses, delivered at 1 Hz), and the saturation threshold for the direct motor component of the evoked EMG was found to be 4 V. For all subsequent testing, stimulation was delivered at 16 V (four times the saturation threshold).

In the study, a 17 mm×3 mm platinum ribbon electrode was placed near the sciatic nerve inside the body, with the exposed platinum face in contact along the length of the nerve at a site distal to the bipolar hook electrodes. Importantly, the platinum ribbon electrode was oriented parallel to the nerve and to maximize surface area contact of the electrode with the nerve. A flap of muscle tissue was placed over the nerve in the 10-mm space intervening between the proximal edge of the platinum ribbon electrode and the bipolar hook cathode. A 19-Gauge needle was placed beneath the skin on the back of the animal, distant to the incision site, to serve as a monopolar return for the direct current.

Assessment of direct current nerve block was made by observing changes in the amplitude of the evoked EMG. Stimulation was delivered repeatedly via the bipolar hook electrodes at a rate of 1 Hz (up to 16 mA via a 50 µs square pulses). In each trial, direct current was delivered in a ramp-up, hold, ramp-down fashion, and the evoked EMG was compared before, during, and after delivery of each trial of direct current. Complete block was defined in this study as a reduction of greater than 80% in the peak-to-peak EMG amplitude relative to pre-trial EMG levels.

FIGS. 18A, 18B, and 19A-19E show experimental results from an animal study of a method of treating pain via electrodes placed in parallel orientation to a target nerve and stimulated via direct-current stimulation, in accordance with an illustrative embodiment.

Specifically, FIG. 18A shows two trials of direct current delivery (at −0.3 mA and −0.2 mA, respectively) (shown as time 1902 and 1904). FIG. 19B shows the recorded EMG before, during, and after each trial of direct current delivery (stimulation delivered at 1 Hz). Complete block of the evoked EMG is evident for the −0.3 mA trial (1902), while partial block was observed during the −0.2 mA trial (1904). FIGS. 19A-19E show representative traces of the evoked EMG at 5 time-points, representing: a) before the first trial (FIG. 19A), b) during the first trial (FIG. 19B), c) between trials (FIG. 19C), d) during the second trial (FIG. 19D), e) after the second trial (FIG. 19E). The stimulus artifact is apparent at the onset of each trace, followed by a biphasic motor response (or in the case of 19B, a lack of motor response).

Notably, in trials not shown here, direct current nerve block was also delivered by placing the platinum ribbon electrode perpendicular to the nerve. In this case complete block was not achieved at amplitudes less than −2 mA.

These results suggest that direct current stimulation delivered via an electrode with a long axis placed in parallel, or substantially in parallel to a long axis of a peripheral nerve facilitates direct current nerve block. Parallel or substantially parallel placement potentially facilitates direct current nerve block at lower, safer amplitudes, than perpendicular or non-parallel placement.

Percutaneously Blocking Painful Sensations Mediated by a Peripheral Nerve Without Eliciting Onset Activity and Co-excitation of Non-targeted Structures.

Another set of embodiments is directed to a system and method that can percutaneously block painful sensations from a target nerve (e.g., a peripheral nerve such as the saphenous nerve, the femoral nerve, brachial plexus nerves, the tibial nerve, the sciatic nerve, the ilioinguinal nerve, the intercostal nerve, the occipital nerve, or the pelvic nerve) without eliciting non-targeted motor and sensory activity, e.g., onset activity and/or co-excitation. The system includes one or more percutaneous electrodes and an electronic control system electrically attached to each electrode. The electronic control system delivers electrical stimulation to the target nerve via a stimulation waveform. The stimulation waveform has a frequency that is greater than about 1.5 kilohertz and less than about 75 kilohertz, and a ramp rate of less than about 2 milliamps/second is utilized to gradually increase an intensity at which the electrical stimulation is delivered until a desired or specified stimulation intensity is reached. In some embodiments, frequency stimulation up to 100 kHz may be used. In some embodiments, direct current stimulation can be used. A system and method of percutaneously blocking painful sensations in a target nerve (e.g., a peripheral nerve) without co-excitation of nearby muscle and without migration of the percutaneous electrode used to deliver the electrical stimulation is also disclosed.

Specifically, the system can include an external waveform generator (e.g., electrical stimulator 128) to deliver electrical energy to a target nerve or target nerve tissue through a percutaneously-placed lead and electrode. The external waveform generator and leads may be embodied in a handheld device that can be easily manipulated to deliver the therapy as well as portable. The external waveform generator and leads may be either reusable or disposable.

Figure 21:
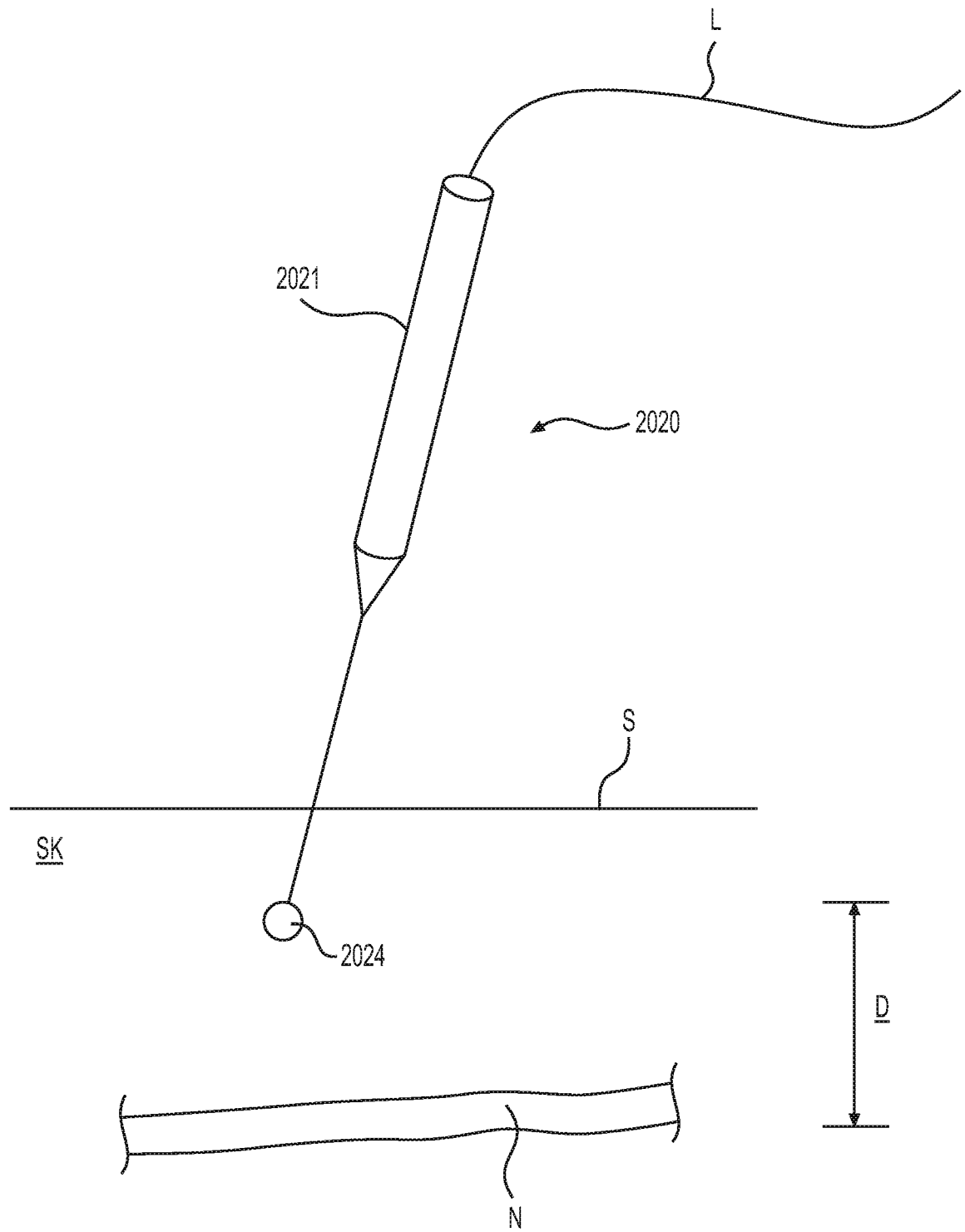
FIG. 21 is a perspective side view of an exemplary system for delivering electrical energy through the a patient's skin to a target nerve in order to percutaneously block painful sensations in the target nerve without eliciting non-targeted motor and/or sensory activity.

The electrode, electrode configuration, and interface embodiment can be designed to maximize and direct the electric field, deliver the therapeutic dose to the target nerve or target nerve tissue, and without unwanted motor or sensory stimulation of nearby tissue, and ensure reliable electrode/nerve placement for optimum therapeutic effect. Factors such as contact number, size, geometry, orientation, material, electrolytic medium, delivery fashion (i.e., monopolar, bipolar, multipolar), and return path may be considered. A cooling mechanism can also be incorporated into the electrode design to control temperature at the electrode-nerve interface. The electrode can also contain a thermistor for recording tissue temperature during stimulation, and for providing feedback information for efficacy and safety measures, and temperature control. FIG. 21, which is discussed in more detail below, shows an electrode can be used to practice methods of the present embodiment. For example, a single percutaneously placed electrode (e.g., in the parallel orientation discussed above) can deliver the desired or specified electrical stimulation to the target nerve or target nerve tissue. Further, independent current channels, electrolytic gel, and electrode insulation can be used to prevent co-excitation of surrounding tissues and to optimize the electrical field that is exposed to the target nerve. The percutaneous electrode can be placed through an introducer assembly or applicator (may include catheter-over-needle or needle-over-catheter approaches where the catheter may include electrical contacts for delivery of the stimulation waveform). The position of specific geometric features of the electrode (e.g., tip configuration, side configuration, number and location of electrode contacts, etc.) relative to the nerve can be optimized to provide the desired therapeutic effect without eliciting non-targeted motor and sensory activity in the target nerve, target tissue, nearby tissue, or a combination thereof.

In addition, the electrical stimulation can be delivered to the target nerve as a direct current stimulation. Further, the electrical stimulation can be a high-frequency stimulation having a sinusoidal waveform, a pulsed waveform, an impulse waveform, a noisy waveform, or a combination thereof. Moreover, the stimulation frequency can be a sinusoidal waveform that can have a constant current or a constant voltage. Further, the stimulation waveform can have a ramping functionality. In particular, the stimulation intensity or amplitude can be less than or equal to about 50 milliamps. For instance, the stimulation intensity or amplitude can range from about 2.5 milliamps to about 40 milliamps, such as from about 5 milliamps to about 30 milliamps, such as from about 7.5 milliamps to about 20 milliamps. In addition, the stimulation waveform, which can be sinusoidal, can have a frequency that is greater than about 1.5 kilohertz and can have a frequency that is less than about 75 kilohertz. Specifically, the stimulation waveform can have a frequency ranging from about 2 kHz to about 60 kHz, such as from about 2.5 kHz to about 50 kHz, such as from about 5 kHz to about 30 kHz, such as from about 7.5 kHz to about 20 kHz. Further, the stimulation waveform can be applied for a time frame ranging from about 1 hour to about 6 weeks, such as from about 2 hours to about 4 weeks, such as from about 3 hours to about 2 weeks. For instance, the stimulation waveform can be applied in post-surgical situations as an alternative to pain medications to treat acute and chronic pain.

In addition, the stimulation waveform can undergo filtering as it travels from the percutaneous electrode to the target nerve due to the distance between the percutaneous electrode and the target nerve as the electrode is not in direct contact with the target nerve. For instance, the distance between the tip of the percutaneous electrode that delivers the electrical energy to the target nerve in the form of a stimulation waveform and the target nerve can range from about 0.5 millimeters to about 15 millimeters, such as from about 0.75 millimeters to about 10 millimeters, such as from about 1 millimeter to about 5 millimeters. Without intending to be limited by any particular theory, the present inventors have found that such separation between the percutaneous electrode and the target nerve can result in filtering of the waveform or distortion of the waveform such that the original alternating current stimulation waveform is not the final waveform that reaches the target nerve. Instead, the target nerve receives a stimulation waveform that takes on a broader spectrum that may include frequency bands at the low frequency (DC) end of the frequency spectrum.

In addition, the stimulation amplitude or intensity can be applied via ramping until the desired or specified stimulation amplitude is achieved. Such ramping can minimize any patient pain or discomfort associated with the onset response that occurs at the initial application of the desired or specified amplitude or intensity of the electrical stimulation. For instance, the stimulation intensity can be applied at a ramp rate of less than about 2 mA/s, such as at a ramp rate ranging from about 0.01 milliamps/second to about 1.75 milliamps/second, such as from about 0.02 milliamps/second to about 1.5 milliamps/second, such as from about 0.03 milliamps/second to about 1.25 milliamps/second, such as from about 0.0.04 milliamps/second to about 1 milliamp/second, such as from about 0.05 milliamps/second to about 0.75 milliamps/second until the desired stimulation amplitude is achieved. Further, the stimulation intensity can be ramped downward at the same rate at which the stimulation intensity was ramped upwards at the end of the stimulation period. Without intending to be limited by any particular theory, it is observed that such ramping rates can completely eliminate or at least decrease the peak sensation or discomfort that may be experienced by a patient during the onset response associated with the application of the electrical stimulation, e.g., where the application of direct current (DC) is not required to eliminate the painful sensations that may be caused by the initial application of the full amplitude sinusoidal or alternating current (AC) electrical stimulation waveform.

Further, in addition to implementing a ramp rate as described above, it is to be understood that alternative or combination waveforms can be used to mitigate the onset response. That is, secondary to ramping, alternative waveforms including combinations of pulses, sinusoidal waveforms, and impulses can be applied until the desired stimulation intensity is reached in order to mitigate the onset response.

Moreover, the blocking effect caused by delivery of the electrical stimulation to the target nerve is reversible in that the block is temporary. Additionally, the block can be a complete block in which 100% of action potentials are blocked or a partial block of action potentials so long as the partial block is sufficient to block painful sensations associated with the target nerve. In addition, the intensity of the block facilitated by the system and method of the present embodiment is titratable in that the ability to increase or decrease the intensity of the block can be considered instantaneous or nearly instantaneous (e.g., the intensity can change within about 15 seconds, such as within about 10 seconds, such as within about 5 seconds, such as within about 2 seconds).

Furthermore, once electrical stimulation is no longer applied, a carry-over block effect can be observed for the particular stimulation waveforms contemplated by the present embodiment, where the carry over effect can be predicted from the block threshold, block amplitude, and block duration. For instance, the carry-over effect facilitated by the application of the electrical stimulation of the present embodiment can last for a period of time that is up to about 1000% of the time during which the electrical stimulation is applied, such as from about 2.5% to about 500%, such as from about 5% to about 250%, such as from about 7.5% to about 100% of the time during which the stimulation waveform is applied. Such an effect can be used to save power during the operation of the system, which can be an important consideration given that the system could be used for a time period ranging from about 1 hour to about 6 weeks or longer.

The system and method of the present embodiment, in some embodiments, includes determining a sensory threshold for each patient and utilizing the sensory threshold to estimate the threshold for painful sensations that can be elicited by the high frequency stimulation, estimate the complete and partial block thresholds, and estimate the optimal ramp rate (e.g., the ramp rate at which the patient does not experience discomfort due to the amplitude of the high frequency stimulation being delivered and does not experience pain due to an insufficient block). For instance, a sensory threshold (e.g., the threshold at which the patient feels a buzzing or tingling sensation) can be determined by delivering a sinusoidal waveform having a frequency of about 1.5 kilohertz to about 75 kilohertz, such as about 2 kilohertz to about 60 kilohertz, such as from about 2.5 kilohertz to about 50 kilohertz, such as from about 5 kHz to about 30 kHz, such as from about 7.5 kHz to about 20 kHz (e.g., about 10 kilohertz) to a patient for a time period ranging from about 0.05 milliseconds to about 5 seconds, such as from about 0.1 milliseconds to about 4 seconds, such as from about 0.2 milliseconds to about 3 seconds and determining the amplitude at which the sensory response is first detected when gradually increasing the amplitude of the waveform being delivered. For instance, the amplitude at which the sensory response is felt as determined via patient feedback can range from about 0.5 milliamps to about 25 milliamps, such as from about 1 milliamp to about 20 milliamps, such as from about 2 milliamps to about 10 milliamps.

In other embodiments, the sensory threshold can be determined by delivering a square waveform (rather than a high frequency sinusoidal waveform as described above) having a pulse width of about 0.05 milliseconds to about 5 seconds, such as from about 0.1 milliseconds to about 4 seconds, such as from about 0.2 milliseconds to about 3 seconds, and determining the amplitude at which the sensory response is felt by gradually increasing the amplitude of the square wave being delivered. For instance, the amplitude at which the sensory response is felt as determined via patient feedback can range from about 0.01 milliamps to about 2 milliamps, such as from about 0.05 milliamps to about 1.75 milliamps, such as from about 0.1 milliamps to about 1.5 milliamps. Then, the sensory response that is felt when a high frequency sinusoidal waveform is delivered can be determined or predicted from the amplitude at which the sensory response for the square waveform is felt. For instance, the sensory threshold in response to the delivery of the high frequency waveform can occur at an amplitude that is from about 1.1 times to about 25 times, such as from about 1.25 times to about 20 times, such as from about 1.5 times to about 15 times the amplitude at which the sensory response for the square waveform is felt. Thus, the delivery of a square waveform can be useful in confirming proper electrode placement while at the same time saving energy and battery life.

Further, regardless of the manner in which the sensory threshold is determined, such sensory threshold amplitude levels can be used to predict when a patient would experience painful sensations during the initial delivery of the high frequency stimulation, referred to as the onset response. Then, this information can be used to determine the optimal ramp rate for each patient so the patient does not feel pain during the ramping up of the stimulation waveform to the blocking amplitude level. In some embodiments, the blocking amplitude can range from about 110% to about 1000%, such as from about 125% to about 800%, such as from about 150% to about 600% of the amplitude of the sensory threshold determined for the patient.

Further, the system and method of the present embodiment can use the sensory threshold, pain threshold, and block duration to control the specific stimulation parameters for achieving a nerve block as quickly as possible, and without causing the patient discomfort or unnecessary co-excitation of nearby tissues. Additionally, the system and method of the present embodiment can prevent overstimulation and can decrease battery consumption by reducing duty cycle, thus improving the safety of the system.

The system and method of the present embodiment also contemplates utilizing nociceptive reflex activity as measured by EMG to aid in percutaneous electrode placement and to confirm efficacy of the block in patients who cannot provide sensory feedback. Specifically, accurate placement of the electrode ensures that co-excitation of the nearby muscle is prevented. Such a system and method involves measuring EMG activity in muscles near or adjacent the target nerve while a test stimulation is delivered from the percutaneous electrode and determining the amount of time between the end of the test stimulation and any elicited, short bursts of muscle activity. The absence of any short-bursts of muscle activity within about 5 milliseconds to about 15 milliseconds after delivery of the test stimulation confirms that muscles are not being directly activated by delivery of the stimulation waveform.

Due to the particular parameters of the stimulation system and stimulation waveform of the present embodiment, the resulting block of the painful sensations emanating from a target nerve or target nerve tissue can be accomplished in a reversible manner and without eliciting non-targeted motor and sensory activity. The system can include control logic and software that can guide the electrode contacts into proximity of the target nerve and ensure optimal placement of each geometrical aspect of the electrode relative to the nerve (e.g., via imaging such as ultrasound imaging or via electrical stimulation to verify proper placement). The control logic and software can also be used to program the various contact channels to assure maximum efficacy and/or electric field coverage of the target nerve, reduce electric field spread to ancillary tissues, and assure stimulation safety by thermal feedback. Further, the control logic and software can be adapted to coordinate the treatment and control the start/stop commands and waveform parameters. In addition, it is to be understood that control of the waveform parameters and application of the therapy may be performed by a caregiver or self-administered by the patient via an external programmer unit.

The system and method of the present embodiment can be used to apply electrical stimulation to the peripheral nerves. Further, it is to be understood that the system and method of the present embodiment can be used to treat acute pain, such as the pain experienced in the hours to weeks after a person has undergone a surgical procedure.

The method of the present embodiment can include identifying the target nerve such as via imaging (e.g., ultrasound) or by delivering low level electrical stimulation and observing the patient response to such stimulation. After the target nerve is identified, the skin can be numbed or anesthetized and one or more electrodes can be percutaneously positioned near the target nerve. Desirably, the electrodes can be attached to an external generator or can be fixed to a handheld stimulation device.

Further, traditional, low level electrical stimulation (e.g., at an amplitude ranging from about 0.1 milliamps to about 2 milliamps, such as from about 0.25 milliamps to about 1.75 milliamps, such as from about 0.5 milliamps to about 1.5 milliamps, such as from about 0.75 milliamps to about 1.25 milliamps can be delivered through the electrodes to assure sufficient tissue/nerve proximity and impedance measurements can be collected and used similarly. Additionally, assessed sensory thresholds can be used to optimize electrode placement and predict or estimate block performance, where the sensory threshold refers to the minimum amount of stimulation intensity that can be delivered to elicit a radiating sensation, for example. After the target nerve tissue is located via one or more of the methods described above, high-frequency electrical stimulation can be delivered to the target nerve (e.g., the saphenous nerve), where the stimulation amplitude or intensity can be slowly ramped upwards to the desired or specified blocking amplitude or intensity, where it is to be understood that the ramp does not have edges or transients, which could result in undesired nerve activation or discomfort for the patient. It is also to be understood that the ramping rate and other parameters can be controlled by the medical professional or can be programmed via software.

In addition, the system can be programmed to optimize channel selection, return electrode selection, and other stimulation parameters. Further, in some embodiments, chemical nerve block agents may be delivered through the electrode lead prior to delivering the therapy, which can mitigate onset response and improve patient comfort. Then, electrical stimulation can be delivered to the target nerve tissue and can temporarily and selectively reduce or abolish painful sensations without eliciting non-targeted motor and sensory activity. Thereafter, the percutaneously placed electrodes can be removed. Meanwhile, if implanted electrodes were used, such electrodes can remain inside the body for further usage and ongoing treatment. Desirably, the generator can be reused, and the electrodes/leads can be disposed.

Referring now to the drawings, the specific features of the system and method of the present embodiment will be discussed in more detail.

Figure 20:
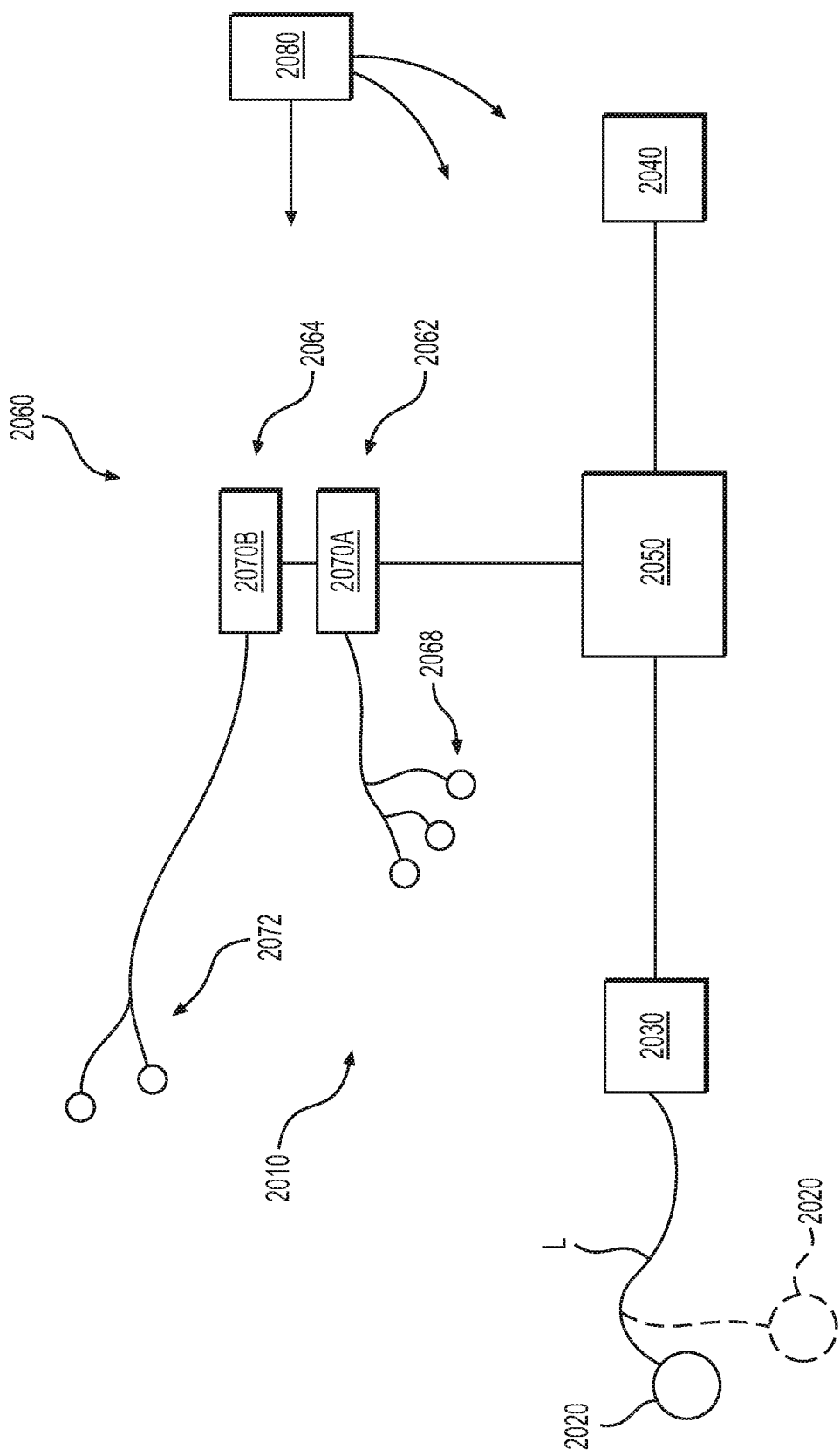
FIG. 20 is schematic diagram of another exemplary system for percutaneously blocking painful sensations in a peripheral nerve without eliciting non-targeted motor and/or sensory activity.

Overview of a System Configured to Deliver Electrical Stimulation Without Eliciting Onset Activity and/or Co-Excitation Referring now to FIG. 20, there is illustrated a system for delivering electrical stimulation for percutaneously blocking painful sensations in a peripheral nerve without eliciting non-targeted motor and sensory activity, e.g., on-set activity or co-excitation. Generally speaking, the electrical stimulation may be delivered to the target nerve utilizing an electrode that may be in the form of a percutaneous electrode assembly to temporarily and selectively block nerve fiber activity in a target nerve.

The system includes multiple devices to control and deliver predetermined electrical pulses at predetermined frequencies and amplitudes to one or more target nerve(s). As shown in FIG. 20, the system, referenced as the schematic system 2010, may include one or more electrode 2020 (shown diagrammatically in FIG. 20 and not in any specific detail) that is connected by an electrical lead "L" to the rest of the system 2010—which includes an external waveform generator 2030 (previously referenced as electrical stimulation system 102), a user interface 2040 (previously referenced as 136), and a controller 2050 (previously referenced as controller 134). The system may also include a patient monitor system 2060, and ultrasound imaging system, and an isolated power system. While an experimental-scale system is shown and described, it is contemplated that a more compact unit could be used to control and deliver the desired electrical stimulation.

Percutaneous Electrode Example #4

The one or more electrodes 2020 may be configured as a percutaneous electrode 2021 (see FIG. 21). The percutaneous electrode 2021 can be in the form of a paddle, cylindrical catheter or needle, wire form, or thin probe. In some embodiment, as can be seen in FIG. 21, there is illustrated a percutaneous electrode 2021 placed beneath the surface "S" of the skin "SK" near or adjacent a target nerve "N". The separation between the tip 2124 of the percutaneous electrode 2021 and the target nerve "N" is identified as distance "D". The distance "D" is on the order of millimeters, where larger distances require more intensive stimulation to achieve a nerve block. For instance, as mentioned above, the distance "D" between the tip 2024 of the percutaneous electrode 2021 and the target nerve "N" can range from about 0.5 millimeter to about 15 millimeters, such as from about 0.75 millimeters to about 10 millimeters, such as from about 1 millimeter to about 5 millimeters.

Figure 22:
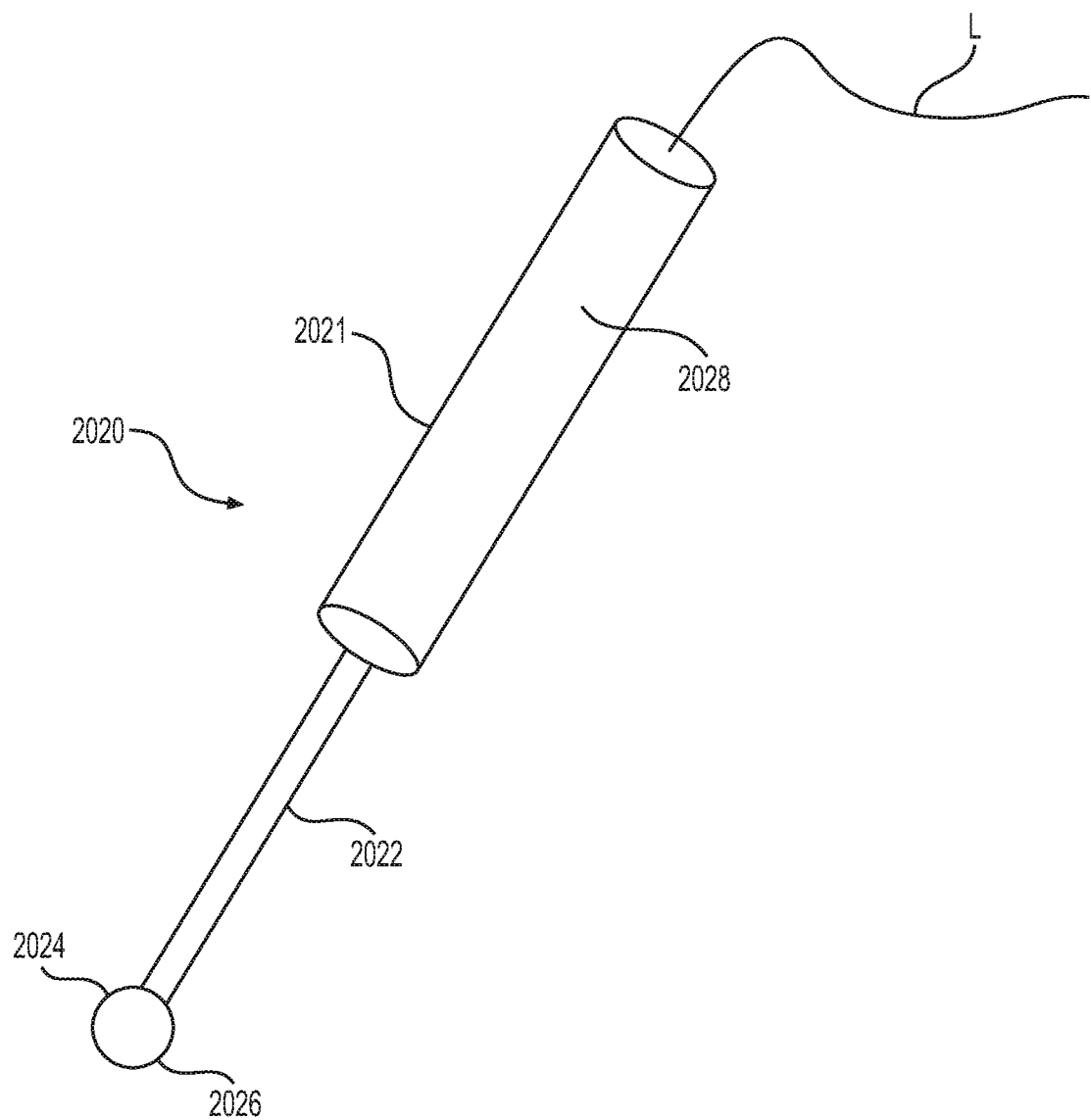
FIG. 22 is a perspective side view of an exemplary electrode utilized in a system of FIGS. 20 and 21 for delivering electrical energy through a patient's skin to a target nerve in order percutaneously block painful sensations in the target nerve without eliciting non-targeted motor and/or sensory activity.

Referring to FIG. 22, the overall shape of the one or more exemplary percutaneous electrodes 2021 is such that it allows an operator to precisely place the electrode tip in the proximity of a target nerve. In another aspect of the embodiment, the electrodes may include an elongated shaft 2022 having a tip 2024 defining a generally uniform tissue contacting surface 2026 at one end, and a support such as a handle 2028 at the opposite end. An electrical lead "L" may be integrated with the electrode 2021 or may be attached using a conventional electrical connector. The tissue contacting surface 2026 of the tip 2024 is an electrically conductive surface.

The percutaneous electrode 2021 may be constructed from a metal or carbon that is conductive and biocompatible, such as stainless steel. The handle 2028, if used, may be large enough for a clinician to comfortably grip, and may be made of material that will minimize the risk of accidental shock, e.g., non-conductive plastic. The percutaneous electrode 2021 is electrically connected to an external waveform generator 2030 by way of an electrical cable or lead-wire.

The tip 2024, in some embodiments, desirably has a blunt end, desirably spherical, spheroidal, hemi-spherical or hemi-spheroidal in shape. The shaft diameter, for a distance of at least about one inch from the tip, is less than or equal to the tip diameter.

In some embodiments, the percutaneous electrodes 2021 may desirably define a generally uniform tissue contacting surface 2026. In some embodiments, the tissue contacting surface 2026 of each percutaneous electrode 2021 has an area of from about 1.5 mm$^2$ to about 100 mm$^2$. In some embodiments, the tissue contacting surface 2026 has an area of from about 3.5 mm$^2$ to about 20 mm$^2$. The tip 2024 of the percutaneous electrode 2021 may have an oval, elliptical or circular cross-section. In some embodiments, the tip 2024 of the percutaneous electrode 2021 is circular and is less than 7 mm in diameter; or less than 5 mm in diameter, or most desirably is about 2.5 mm diameter. A smaller percutaneous electrode may be more controllable so it may be easier to position the electrode a desired or pre-defined distance from superficial muscle groups and non-target nerves.

In another aspect of the embodiment, the shaft 2022 may be coated with TEFLON® fluoropolymer or other conventional insulating material to create a higher field density at the tip 2024. The relatively small tip 2024 may provide a relatively large current density of about 942 mA/cm$^2$ (20 mA peak current; 1.5 mm$^2$ surface area), to 1 mA/cm$^2$ and most desirably, 140 mA/cm$^2$ (calculated with a 2.5 mm tip diameter; square-wave pulses; 50% duty cycle).

FIGS. 23A-23D each shows a perspective side view of an exemplary percutaneous electrode 2021 as illustrated in FIG. 22. Specifically, FIG. 23A illustrates an exemplary electrode tip 2024A extending from the shaft 2022 of the percutaneous electrode 2021. The electrode tip 2024A has a generally spherical shape to provide a generally uniform tissue contacting surface 2026. FIG. 23B illustrates another exemplary electrode tip 2024B extending from the shaft 2022 of the percutaneous electrode 2021. The electrode tip 2024B has a generally spheroidal shape (e.g., an oblate spheroid) to provide a generally uniform tissue contacting surface 2026. FIG. 23C illustrates yet another exemplary electrode tip 2024C extending from the shaft 2022 of the percutaneous electrode 2021. The electrode tip 2024C has a generally hemi-spherical shape to provide a generally uniform tissue contacting surface 2026. FIG. 23D is an illustration of still yet another exemplary electrode tip 2024D extending from the shaft 2022 of the percutaneous electrode 2021. The electrode tip 2024D has a generally hemi-spheroidal shape (e.g., about one-half of an oblate spheroid). Indeed, it is contemplated that a variety of other shapes and configurations may be utilized for the percutaneous electrodes contemplated by the present embodiment.

Figure 24A:
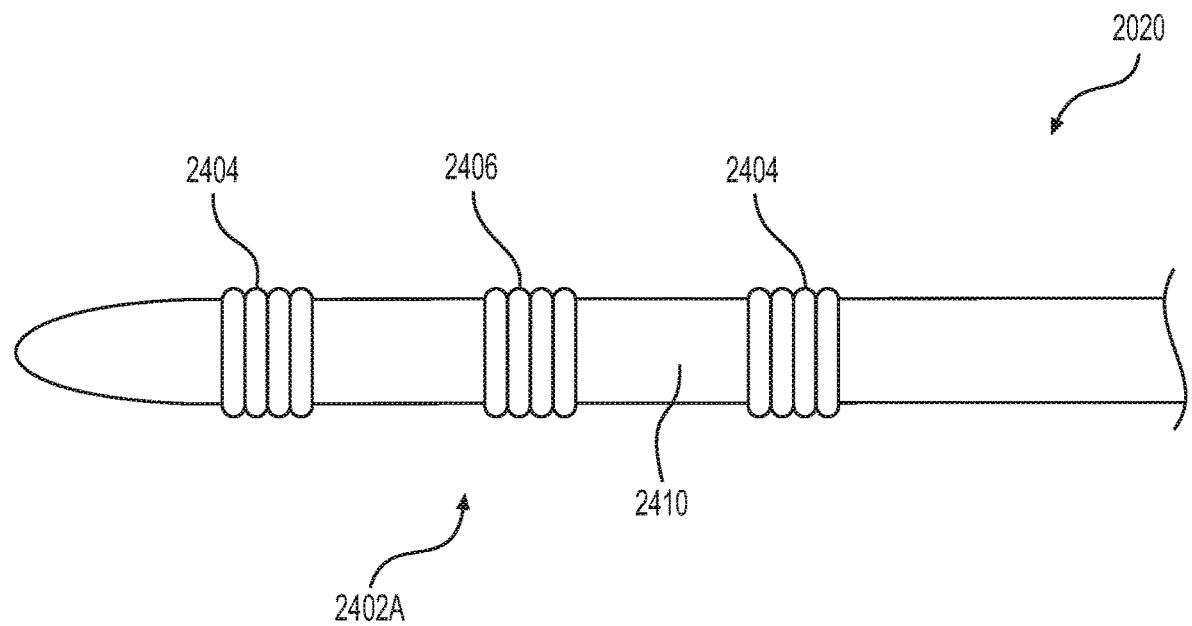
FIG. 24A is a side perspective view of an exemplary percutaneous electrode assembly utilized for delivering electrical stimulation to the vicinity of a target nerve in order to block painful sensations in the target nerve without eliciting non-targeted motor and/or sensory activity.

Referring generally to FIGS. 24A through 24D, and more specifically to FIG. 24A, there is illustrated in side perspective view of another exemplary electrode 2020 for delivering electrical stimulation to a target nerve, where the electrode 2020 is also in the form of a percutaneous blocking electrode(s) 2402A that is placed nearby a target nerve. Each blocking electrode 2402A used in a bipolar or multi-polar fashion has an anode 2404 and a cathode 2406 placed nearby a target nerve "N". Monopolar percutaneous blocking electrodes have a cathode 2406 located nearby a nerve, and a return electrode (i.e., anode) positioned some distance away (e.g., in the form of a patch electrode on the surface of the skin). Bipolar and multipolar electrode configurations include multiple contacts and thus have at least one cathode and one anode in the vicinity of the target nerve. The electrode shape and size, and inter-electrode spacing are specific to contouring the electrical field surrounding the nerve, to facilitate high frequency or direct current blocking that is selective for painful sensations and that does not block non-targeted motor and sensory activity (e.g., the sense of touch). For example, a suitable multipolar electrode may include a center cathode electrode 2406 that is flanked by two anodes 2404, where the anodic electrodes are connected together, effectively sharing a charge. The electrodes may be circumferential in shape (e.g., disposed radially at the surface of the electrode) and have a diameter ranging from 0.25 mm to 10 mm, and a width from 0.25 mm to 10 mm. For example, the electrodes may have a diameter ranging from about 0.25 mm to 5 mm, and a width from 0.25 mm to 5 mm. As another example, the electrodes may have a diameter ranging from about 0.25 mm to 3 mm, and a width from 0.25 mm to 3 mm. The inter-electrode spacing may have a range from 0.5 mm to 10 mm. Moreover, the electrodes may have varying impedances, to better contour the electric field that will block the nerve.

Figure 24B:
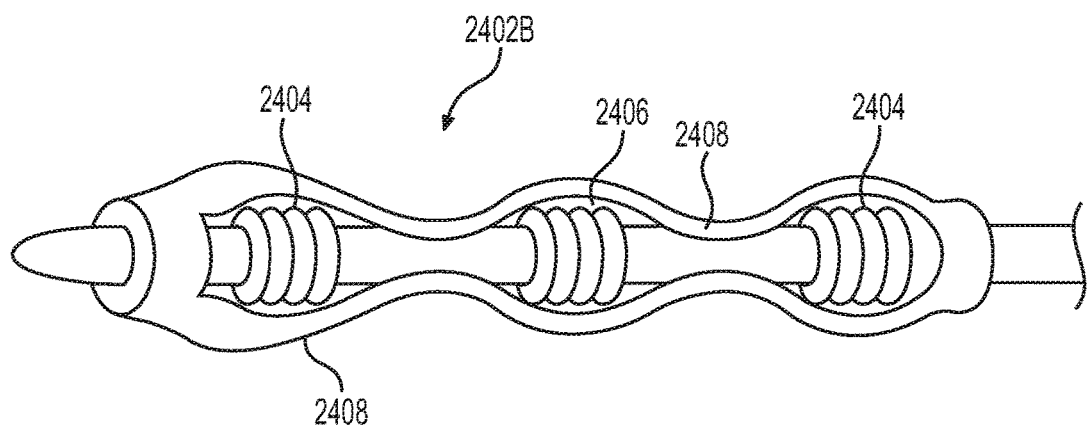
FIGS. 24B and 24C are side perspective views of exemplary percutaneous electrodes for delivering electrical energy to the vicinity of a target nerve in order to block painful sensations in the target nerve without eliciting non-targeted motor and/or sensory activity in which an anode and cathode are present on only a portion of the radial surface of the electrode.
Figure 24C:
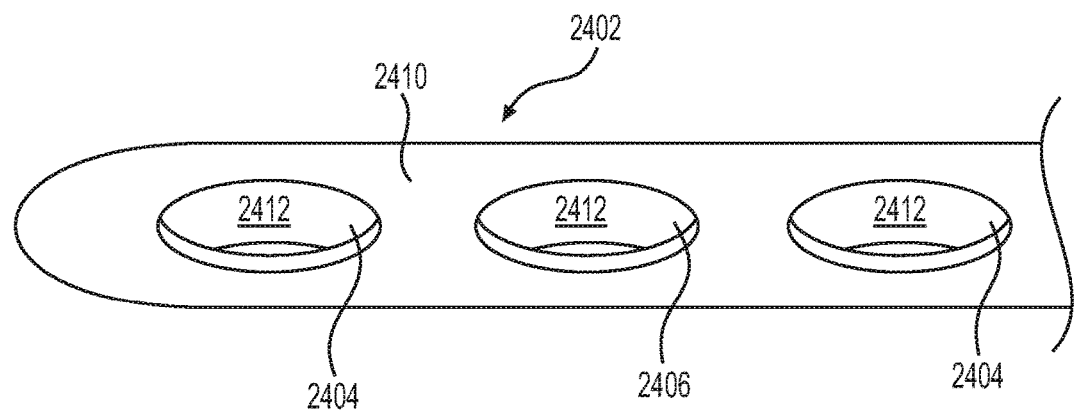

Referring now to FIG. 24B, there is illustrated a side perspective view of an exemplary percutaneous electrode 2402B for delivering electrical stimulation directly to the vicinity of a target nerve to selectively block nerve fiber activity and in which an anode 2404 and cathode 2406 are present on only a portion of the radial surface of the electrode assembly. As can be seen in FIG. 24B, shielding 2408 covers portions of the anode 2404 and cathode 2406 so the anode and cathode are present on only a portion of the radial surface of the electrode assembly. FIG. 24C illustrates anodes 2404 and a cathode 2406 in the form of small plates or tabs 2412 located on the radial surface 2410 of the percutaneous electrode 2402C. While FIGS. 24A-24C illustrate the exemplary percutaneous electrode in multipolar configuration, the electrode may have a bipolar or monopolar configuration.

Figure 24D:
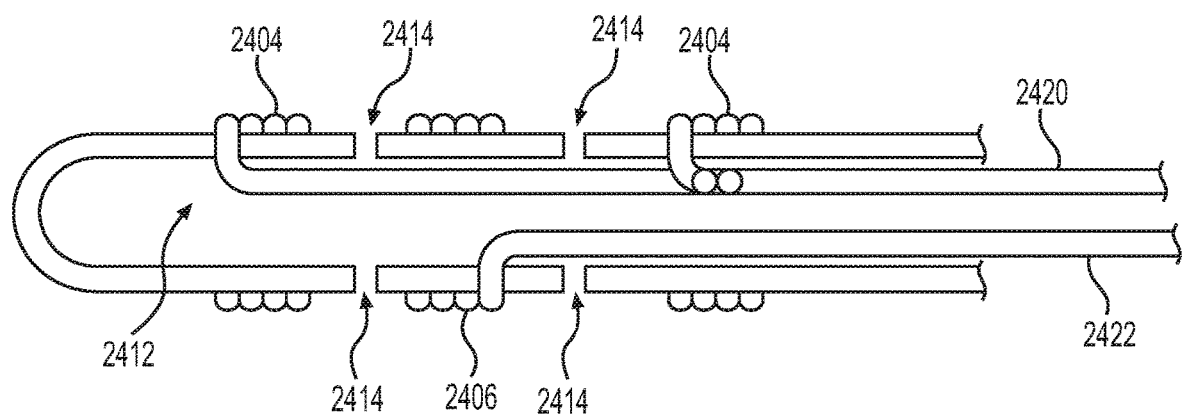
FIG. 24D is a side cross-sectional view of an exemplary percutaneous electrode assembly including a lumen or passageway for delivering fluid therethrough.

FIG. 24D is a side cross-sectional view of an exemplary percutaneous electrode 2402 (e.g., 2402A, 2402B, 2402C) including a lumen or passageway 2412 for delivering fluid therethrough. The percutaneous electrode 2402 (e.g., 2402A, 2402B, 2402C) may define a lumen or passageway 2412 through the electrode to channel a fluid through the electrode and may further define openings 2414 in communication with the lumen or passageway 2412 to deliver fluid out through the electrode. In some embodiments, the electrode assembly defines openings 2414 adjacent the anode 2404 and cathode 2406. However, these openings 2414 may be at other locations. The lumen or pathway 2412 may be integrated with or connected to a tube to deliver fluid to the lumen. The delivery tube can have a standard Luer connection or similar connection.

As can be seen in FIG. 24D, the anodes 2404 are paired or joined by a lead 2420 and the cathode 2406 is connected to a different lead 2422. The electrode assembly may be connected to a fluid flow path in communication with a fluid pump; the fluid flow path may be configured to deliver a fluid to be dispensed to a patient through the electrode assembly. Alternatively, and/or additionally, the electrode assembly may be connected to a bolus reservoir in communication with a bolus flow path. The bolus reservoir may be configured to selectively permit fluid to be dispensed to a patient through the electrode assembly. The arrangement may include a patient operable actuator configured to dispense fluid from the bolus reservoir. In such configuration, the percutaneous electrode can be used to deliver medicinal fluid such as liquid anesthetic in addition to nerve blocking electrical stimulation. The medicinal liquid may be a bolus of anesthetic or it may be an antibiotic material, antimicrobial material or an electrolytic solution to enhance delivery of electrical stimulation. Exemplary fluid pumps, fluid flow paths and bolus delivery configurations or systems are described in U.S. Pat. No. 6,981,967 issued Jan. 3, 2006 to Massengale et al., for "Large Volume Bolus Device and Method", incorporated herein by reference.

Similar lumen or passageway may be similarly implemented in the percutaneous leads 106a, 106b, 106c, and etc.

Turning now to FIGS. 25 and 26A-26D, other possible embodiments of a percutaneous electrode 2121 that can be particularly effective in reducing co-excitation of muscles near the target nerve due to volume conduction and that can prevent migration of the percutaneous electrode 2121 are shown.

Figure 25:
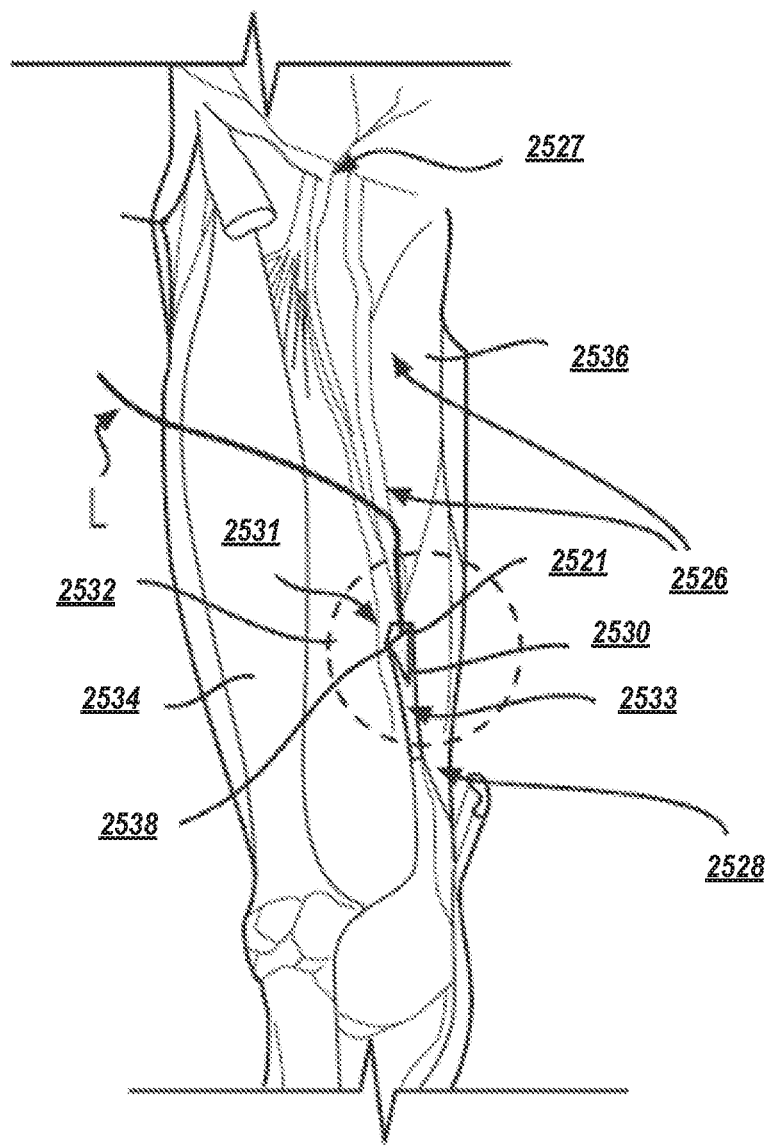
FIG. 25 is a perspective view of another exemplary percutaneous electrode utilized in a percutaneous nerve block system, where the electrode has been inserted into the adductor canal at and/or within the intermuscular septum.

Specifically, FIG. 25 is a view of a percutaneous electrode 2521 attached to a lead L that has been inserted into the adductor canal 2526 at a proximal end 2531 of the intermuscular septum 2530, where the proximal end 2531 is wider than a distal end 2533, and where the adductor canal 2526 is located under the sartorius muscle 2532 and borders the vastus medialis muscle 2534 and adductor longus muscle 2536. In particular, the percutaneous electrode 2521 can be inserted into a triangular-shaped cavity or pocket 2538 defined by the intermuscular septum 2530 such that the percutaneous electrode 2521 is in proximity to the saphenous nerve 2528.

Figure 26A:
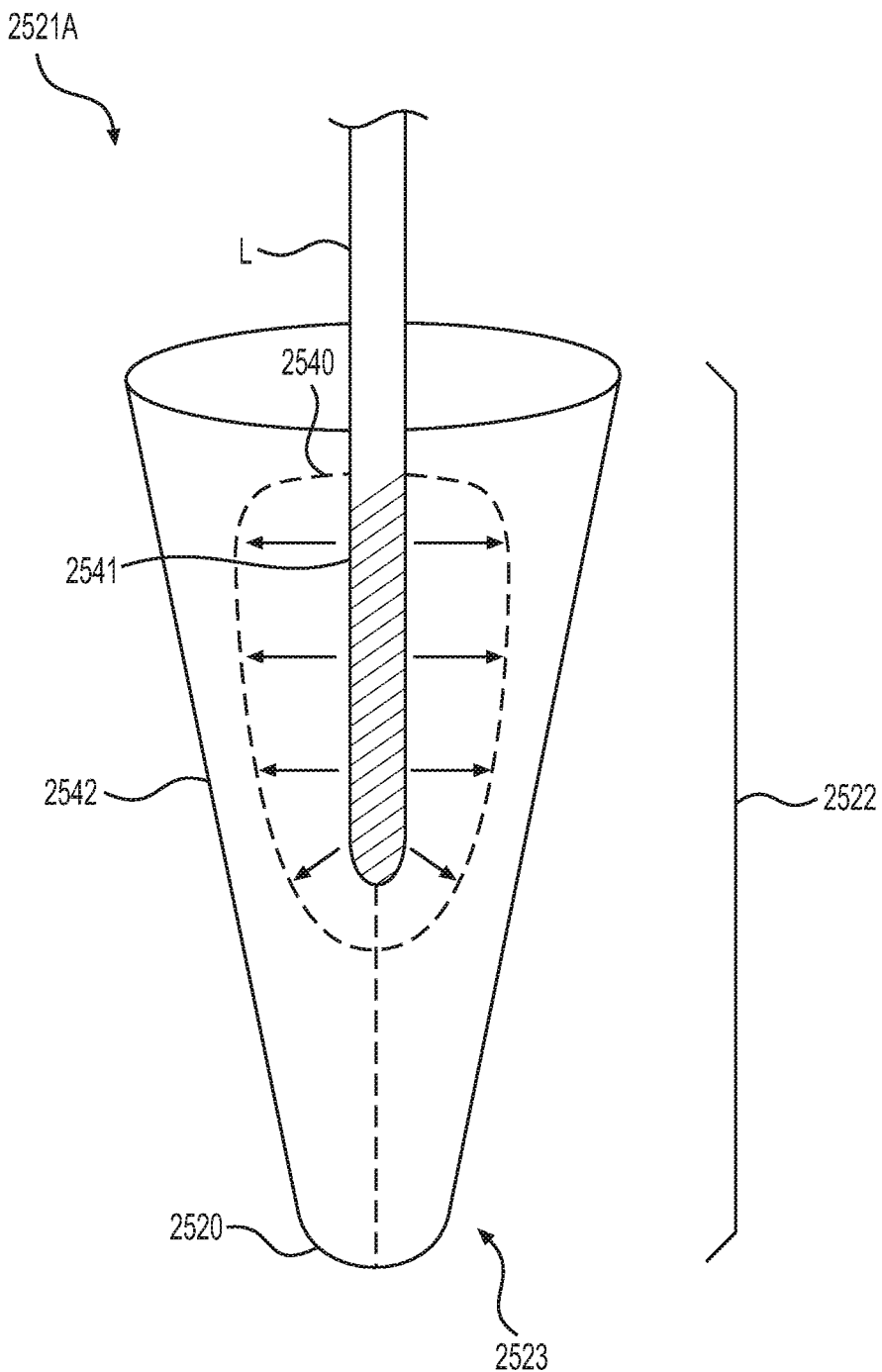
FIG. 26A is a perspective side view of the percutaneous electrode of FIG. 12.

FIG. 26A is a perspective side view of the percutaneous electrode 2521 (shown as 2521A) of FIG. 25. As shown in FIG. 26A, the electrode 2521A can be attached to a lead L and the electrode contact 2520 can be present at the tip 2523 of the electrode 2521A. Further, the electrode 2521A can include a fixation element 2542 (e.g., an inflatable material) that can be compressed against the lead L along a portion 2522 when first being inserted into the intermuscular septum 2530. Then, once the electrode 2521A is in proper position within the cavity or pocket 2538 defined by the intermuscular septum 2530, the fixation element 2542 (e.g., inflatable material) can be expanded, such as via an air source 2540, mechanical or electrical actuation, where the transition from the compressed state 2541 to the expanded or inflated state is represented by the arrows in FIG. 26A. A sufficient amount of air 2540 can be introduced into the percutaneous electrode 2521 so that the percutaneous electrode 2521 fits snugly within the cavity or pocket 2538 of the intermuscular septum 2530 without migrating and so that the percutaneous electrode embraces the contour of the target nerve (e.g., the saphenous nerve 2528). Then, once the stimulation is completed (e.g., after a time period ranging from about 1 hour to about 6 weeks), the percutaneous electrode 2521 (e.g., 2521A) can be removed (e.g., by a medical professional or a patient) from the cavity or pocket 2538 upon a release mechanism. In addition, although a single electrode contact 2520 is shown, it is to be understood that multiple electrode contacts can be used to deliver the electrical stimulation (e.g., one or more electrode contacts on a surface of the inflatable material 2542). Further, the entire surface of the fixation element 2542 can serve as a single electrode contact 2520.

Figure 26B:
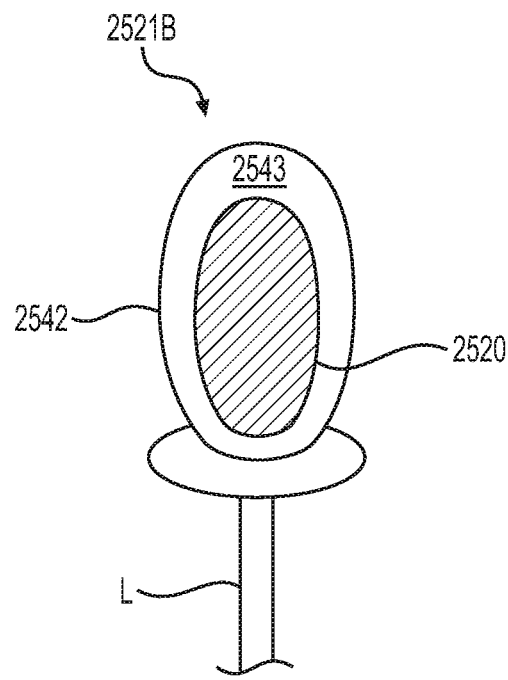
FIGS. 26B, 26C, and 26D each is a perspective side view of other exemplary percutaneous electrode utilized in a percutaneous nerve block system, where the electrode is designed for insertion into the adductor canal at and/or within the intermuscular septum.

FIG. 26B is a perspective side view of still another exemplary percutaneous electrode 2521 (shown as 2521B) utilized in a percutaneous nerve block system, where the electrode 2521B is designed for insertion into the adductor canal 2526 at the level of the intermuscular septum 2530. The percutaneous electrode 2521B shown in FIG. 26B is similar to that shown in FIG. 26A and can have an inflatable balloon-like shape where the electrode contact 2520 is present on an outer surface 2543 of the inflatable material 2542.

Figure 26C:
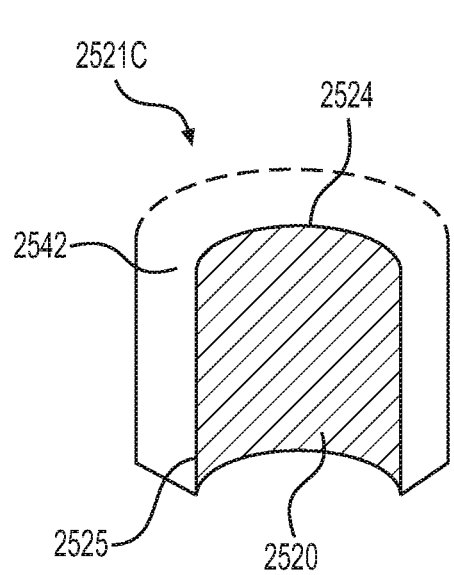

Meanwhile, FIG. 26C is a perspective side view of yet another exemplary percutaneous electrode 2521 (shown as 2521C) utilized in a percutaneous nerve block system, where the electrode 2521C is designed for insertion into the adductor canal 2526 at the level of the intermuscular septum 2530. As shown in FIG. 26C, the electrode 2521C can include an inflatable material 2542 having an arcuate or semi-circular portion 2524, where an electrode contact 2520 can be positioned on an interior surface 2525 of the arcuate or semi-circular portion 2524.

Figure 26D:
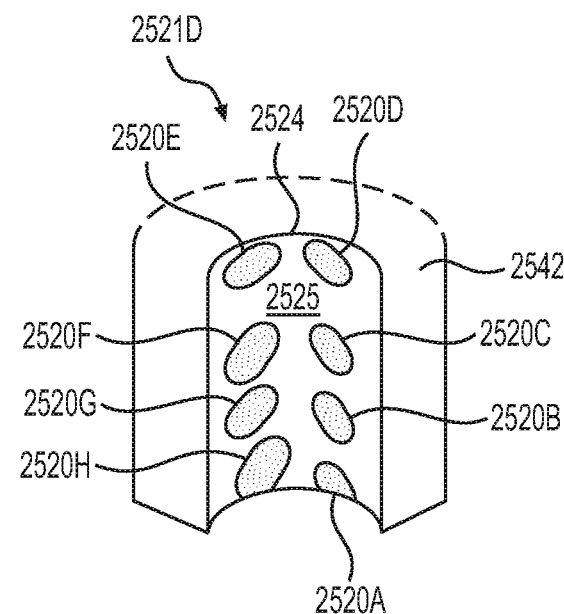

However, it is to be understood that as an alternative to a single electrode contact 2520, multiple electrode contacts (e.g., from about 2 to 20 contacts, such as from about 4 to 16 contacts, such as from about 6 to 12 contacts) can be utilized as shown in FIG. 26D, where electrode contacts 2520a, 2520b, 2520c, 2520d, 2520e, 2520f, 2520g, and 2520h can be disposed on the interior surface 2525 of the arcuate or semi-circular portion 2524. In addition, FIG. 26D is a perspective side view of one more exemplary percutaneous electrode 2521 utilized in a percutaneous nerve block system, where the electrode 2521 is designed for insertion into the adductor canal 2526 at the level of the intermuscular septum 2530.

Further, although the percutaneous electrodes 2521 of FIGS. 25 and 26A-26D are shown as being formed from an inflatable material, it is to be understood that any suitable electrode material can be utilized so long as the percutaneous electrode 2521 can snugly fit within the cavity 2538 of the intermuscular septum 2530. Further, in some embodiments, the percutaneous electrode 2521 may be inserted into the adductor canal space. In addition, although the percutaneous electrodes 2521 of FIGS. 25 and 26A-26D are shown as being placed in proximity to the saphenous nerve 2528, it is to be understood that the percutaneous electrodes 2521 of FIGS. 25 and 26A-26D (as well as other percutaneous leads designs provided herein) can be utilized in systems and method for blocking other nerves besides the saphenous nerve, such as the femoral nerve.

Without intending to be limited by any particular theory, the exemplary percutaneous electrode 2521 designs of FIGS. 25 and 26A-26D are particularly suitable for treating knee pain by blocking the saphenous nerve 2528 at the adductor canal 2526 via one or more electrodes 2520. Specifically, the percutaneous electrodes 2521 are configured to fit snugly within a cavity 2538 defined by the intermuscular septum 2530. Such an electrode configuration can allow for the delivery of an immediately reversible nerve block of the saphenous nerve 2528 without evoking motor activity of the muscles forming the adductor canal 2526 (e.g., the sartorius 2532, vastus medialis 2534 and adductor longus 2536) due to volume conduction, thus reducing or eliminating muscle co-excitation. In addition, such a configuration can also prevent migration of the percutaneous electrode 2521 within the adductor canal 2526. Moreover, because the percutaneous electrode 2521 requires placement in the proximity of the saphenous nerve 2528 via requires penetration through the sartorius muscle 2532, the risk of accidental removal of the percutaneous electrode 2521 by a patient is also mitigated, which is a concern in a system 2010 that is being used to deliver a block over a time period of up to about 6 weeks.

Generally, selective modulation and blocking of saphenous nerve activity can be tailored to the anatomy of the adductor canal 2026. The adductor canal presents 2526, as an aponeurotic tunnel, is located in the middle third of the front of the thigh. It is located under the sartorius muscle 2532 and borders with the vastus medialis 2534 and adductor longus/magnus muscles 2536. The adductor canal 2526 contains the saphenous nerve 2528, the femoral nerve, artery and vein 2527 (see FIG. 25), and lymph nodes (not shown). In the distal anteromedial third of the thigh, the adductor canal 2526 is covered by the intermuscular septum (subsartorial fascia) 2530, which extends from the vastus medialis 2534 to the adductor longus/magnus 2536 muscles creating a triangular-shaped cavity or pocket 2538. This cavity or pocket 2538 is located at the distal third of the thigh and is about 5 centimeters to 6 centimeters long with the proximal opening of about 2 centimeters providing enough space for safe placement of the percutaneous electrodes 2521 of FIGS. 25 and 26A-26D. Near this site, the saphenous nerve 2528 can have a diameter ranging from about 3 millimeters to about 4 millimeters. Structurally, the intermuscular septum 2530 is composed of connective tissue which may serve as an electrical isolator separating the saphenous nerve 2528 from surrounding excitable tissues. To this end, in preliminary EMG studies, high frequency electrical stimulation delivered to the saphenous nerve 2528 percutaneously at the intermuscular septum 2530 with large stimulation amplitudes up to 25 mA resulted in no co-excitation of nearby muscles.

As such, the percutaneous electrodes 2521 can be inserted into the triangular-shaped cavity or pocket 2538 of the intermuscular septum 2530 covering the adductor canal 2526, where the percutaneous electrodes 2521 can be inserted in a direction corresponding to a direction in which the saphenous nerve 2528 runs and at a location spaced a distance from the saphenous nerve 2528, such as a distance up to about 1.5 centimeters. The electrical stimulation to block painful sensations hosted by the saphenous nerve 2528 can be delivered to the saphenous nerve 2526 at the intermuscular septum 2530 of the adductor canal 2526, where the saphenous nerve 2526 can be selectively modulated and blocked by percutaneous electrical stimulation without co-activation of nearby nerves and muscles, while at the same time preventing electrode migration within the adductor canal 2526. Further, the percutaneous electrode design utilized in the exemplary system and method allows for an straightforward and safe electrode removal, which can be conducted by a physician or a patient, thus allowing the use of the present embodiment in a single, in-patient or out-patient procedure lasting seconds-to-minutes that can be performed before or after a surgical procedure, where the system and method can be designed to deliver electrical stimulation after a surgical procedure that can last for hours to weeks and may include a complete or partial block of the target nerve (e.g., the saphenous nerve) for alleviation of acute and/or chronic pain, such as acute and/or chronic pain arising from the knee and/or the medial aspect of the leg and foot.

Returning now to the percutaneous electrode design in general, regardless of its particular design, the percutaneous electrode ensemble may deliver stimulation in a monopolar fashion or mode. In this monopolar mode, one or more stimulating electrode(s) is positioned over the target nerve and a second dispersive electrode with a relatively larger surface area is positioned on a surface of the patient's body to complete the circuit. Alternatively, the stimulation may be delivered in a bipolar fashion or mode and the above-described system may further include one or more anodes, where each anode can be present on the percutaneous electrode or, alternatively, can be disposed on a skin contacting surface. When the stimulation is delivered in a bipolar fashion or mode, the one or more electrode(s) (also referred to as a "cathode(s)" is positioned near or adjacent the target nerve percutaneously and one or more anode(s) is positioned near or adjacent the target nerve percutaneously or, alternatively, on the skin over the target nerve to preferentially concentrate the delivery of electrical energy between the cathode(s) and anode(s). In either mode, the electrodes should be positioned a sufficient distance away from each other, to avoid shunting and a possible short-circuit. The tissue contacting surface or skin contacting surface of each anode will desirably have at least the same or greater surface area as the tissue contacting surface of the stimulating electrode(s).

External Waveform Generator/Stimulator

The electrode(s) 2020 or 2021 (e.g., percutaneous electrode(s)) can be connected to an external waveform generator 2030 through an electrical lead "L". In one embodiment, the external waveform generator 2030 can be a bipolar constant current stimulator. One exemplary stimulator is the DIGITIMER DS5 peripheral electrical stimulator available from Digitimer Ltd., England. Other constant current and constant voltage waveform generators can also be used. Exemplary generators may include Model S88x, S48, or SD9 Stimulators available from Grass Technologies, a subsidiary of Astro-Med, Inc., West Warwick, R.I., USA. Monopolar stimulation may also be used to block neural transduction.

User Interface

Referring back to FIG. 20, the system 2010 can also utilize a user interface 2040. This user interface 2040 may be in the form of a computer that interacts with the controller 2050 and is powered by an isolation system 2080, each described herein.

The computer operates software designed to record signals passed from the controller, and to drive the controller's output. Possible software includes Cambridge Electronic Design's (UK) SPIKE program. The software is programmable and can record and analyze electrophysiological signals, as well as direct the controller to deliver stimulation.

Patient Monitor System

Referring still to FIG. 20, an optional patient monitor system 2060 may be used in conjunction with the electrical stimulator 2030 and user interface 2040. The patient monitoring system 2060, in some embodiments, acquires, amplifies and filters physiological signals, and outputs them to the controller. The optional monitoring system 2060, in some embodiments, includes a heart-rate monitor 2062 to collect electrocardiogram signals, and muscle activity monitor 2064 to collect electromyography signals. The heart-rate monitor 2062 includes ECG electrodes 2068 coupled with an alternating current (AC) amplifier 2070A. The muscle activity monitor 2064 includes EMG electrodes 2072 coupled with an AC amplifier 2070B. Other types of transducers may also be used. As described, all physiological signals obtained with the patient monitoring system are passed through an AC signal amplifier/conditioner (2070A, 2070B). One possible amplifier/conditioner is Model LP511 AC amplifier available from Grass Technologies, a subsidiary of Astro-Med, Inc., West Warwick, R.I., USA.

Isolated Power System

All instruments are powered by an isolated power supply or system 2080 to protect them from ground faults and power spikes carried by the electrical main. An exemplary isolated power system is available is the Model IPS115 Isolated Medical-grade Power System from Grass Technologies, a subsidiary of Astro-Med, Inc., West Warwick, R.I., USA.

Ultrasound Imaging System

An ultrasound imaging system 2066 can be used to identify the target nerve that is to be electrically stimulated and assist a medical professional in properly placing the percutaneous electrode(s) near or adjacent the target nerve. However, it is also to be understood that the target nerve can alternatively and/or additionally be identified via applying low level electrical stimulation and observing for an appropriate sensory or motor response (e.g., muscle twitch).

Controller

A controller 2050, which can include control logic and software designed to deliver the desired electrical stimulation to a patient, records waveform data and digital information from the patient monitor system 2060 and can generate waveform and digital outputs simultaneously for real-time control of the external waveform generator 2030. The controller 2050 may have onboard memory to facilitate high speed data capture, independent waveform sample rates and on-line analysis. An exemplary controller 2050 may be a POWER 1401 data-acquisition interface unit available from Cambridge Electronic Design (UK).

The present embodiment also encompasses a kit for an electrical nerve block procedure. It should be appreciated that the kit need not contain all of the articles and/or components depicted in FIGS. 20 through 24D. In another embodiment, a kit may be provided for articles and/or components depicted in FIGS. 1 through 15 or combination thereof with those of FIGS. 20 through 24D. Indeed, components such as controller, external waveform generator, user interface, patient monitoring system, amplifiers or the like need not be included—although suitable electrodes such as the ECG and EMG electrodes may be included in the kit.

The kit may include a container that may be, for example, a suitable tray having a removable sealed covering in which the articles are contained. For example, an embodiment of the kit may include the container with one or more electrodes 2020 (e.g., percutaneous electrodes 2021 or percutaneous leads 104 (e.g., 104*a*, 104*b*, 104*c*)) and electrical leads "L" as discussed above. The kit may further include one or more anodes. Each anode desirably has at least the same (or greater) surface area as the tissue contacting surface of the stimulating percutaneous electrode.

The embodiments encompasses a kit with any combination of the items utilized to perform the procedure of delivering electrical stimulation utilizing percutaneous electrodes described herein. For example, other embodiments of a kit may include additional items, such as ECG electrodes 2068 (or percutaneous leads 104 (e.g., 104*a*, 104*b*, 104*c*)) and EMG electrodes 2072, as well as any combination of a drape, site dressings, tape, skin-markers and so forth. The kit may include one or more containers of electrically conductive liquids or gels, antiseptics, or skin-prep liquids. The kit may include pre-packaged wipes such as electrically conductive liquid or gel wipes, antiseptic wipes, or skin-prep wipes. The kit may contain medicinal liquids and/or electrolytic solutions. For example, the electrolytic solution may be or may include a bioresorbable gel material that is injected in liquid form but becomes substantially viscous or even solid-like after exiting the openings in the percutaneous electrode.

Electrical Stimulation Method to Avoid Onset Activity and Co-Excitation

The present embodiment also encompasses a method for temporarily and selectively blocking nerve fiber activity in a target nerve. For instance, electrodes can be positioned near the target nerve (e.g., in parallel, or substantially in parallel, to a target nerve over an overlapping region greater than about 3 mm), in a percutaneous fashion. Desirably, the electrodes can be positioned percutaneously and attached to an external generator, and/or can be fixed to a handheld stimulation device. Traditional electrical stimulation can then be delivered through the electrodes to assure sufficient tissue/nerve proximity, and impedance measurements can be collected and used similarly. The system can be programmed to optimize channel selection, return electrode selection, and stimulation parameters as discussed above. Chemical nerve block agents can also be delivered through the electrode lead prior to delivering the temporary and selective stimulation therapy such as to mitigate onset response and/or improve patient comfort. Stimulation can then be delivered to the target nerve in order to block pain for a period of hours-to-weeks. After the stimulation is delivered for the desired time frame post-surgery, the percutaneous electrodes can be removed. Desirably, the external waveform generator can be reused, and the leads can be disposed.

In particular, the method can involve the steps of: locating a target nerve; positioning one or more electrodes through the skin near the target nerve; and delivering electrical stimulation to the target nerve using one or more of the stimulation parameters discussed above. Further, in its simplest form, the method may rely on a patient's (e.g., the user) feedback of pain after delivery of nerve blocking stimulation to assess the effectiveness of the temporary and selective nerve block. Alternatively, and/or additionally, the method may rely on feedback collected by a recording electrode, such as the exemplary recording electrode described above, and/or electromyogram signals to assess the effectiveness of the temporary and selective nerve block, since the stimulation may occur during or immediately after a surgical procedure when the patient is not able to provide feedback.

The method of practicing the present embodiment may further include the use of coupling media such as, for example, an electrically conductive liquid, gel or paste that may be disposed within a sheath around a percutaneous probe to maximize and direct the electric field, deliver the therapeutic dose of stimulation, and ensure reliable electrode/nerve placement for optimum therapeutic effect. Examples of conductive pastes include Ten20™ conductive paste from Weaver and Company, Aurora, Colo., and ELEFIX Conductive Paste from Nihon Kohden with offices at Foothill Ranch, Calif. Examples of conductive gels include Spectra 360 Electrode Gel from Parker Laboratories, Inc., Fairfield, N.J., or Electro-Gel from Electro-Cap International, Inc., Eaton, Ohio.

Electrical Nerve-Blocking Stimulation

In some embodiments, the procedure for setting up a treatment comprises the following steps.

1. Setup stimulation system near a stable patient bed either before, during, or immediately after a surgical procedure.
2. Place patient into a comfortable supine position.
3. Place the optional ECG and EMG on patient.
4. Begin monitoring heart-rate and EMG.
5. Locate the target nerve, either by utilizing any suitable imaging system (e.g., an ultrasound imaging system) or by passing low-levels of stimulation through the stimulator that is used for blocking. A stimulus-elicited muscle twitch in a distal muscle group with low-stimulation amplitudes (single pulse) will indicate that the stimulation point is proximal enough for blocking of the target nerve.
6. Position the tip of the blocking percutaneous electrode in the vicinity of the nerve and maintain the stimulation electrode in this position.

sensory-threshold) that faded within seconds, and before the high-frequency stimulation was terminated. Sensory-threshold was determined as the weakest stimulation intensity (10 cycles of a 10-kHz sinewave; 1 ms stimulation duration) that the subject could detect. It was also observed that high-frequency stimulation with an intensity of about 150% of sensory-threshold (6 mA) elicited a sensation consistent with the subject's threshold for pain (sensory score of 3), which again faded to baseline before the stimulation was terminated.

Table 1 shows the average (±standard deviation) sensory response to high-frequency electrical stimulation in an able-bodied subject delivered percutaneously, and with various stimulation amplitudes. Table 1 also provides the various criteria used to describe the sensory response. Criteria includes: 1. Peak sensory score (11-point scale); 2. Response area (in units, mA*s); 3. Onset latency, or minimal time to feel the sensory response (in seconds); 4. Peak latency or time to feel the peak sensation/sensory score (in seconds), and 5. Offset time for the sensory response to cease (in seconds). Indeed, FIG. 27 and Table 1 show that the peak sensation and response area increased with the amplitude of the high-frequency electrical stimulation, while the onset latency decreased. Peak latency and offset latency were more variable. It was also observed that the elicited sensations always terminated within seconds of it being evoked.

TABLE 1

| Amplitude (mA) | Peak Sensation (0-11 Scale) | Response Area (mA*s) | Onset (seconds) | Peak Latency (seconds) | Offset (seconds) |
| --- | --- | --- | --- | --- | --- |
| 4 | 0.35 (±0.09) | 0.64 (±0.22) | 1.82 (±0.31) | 3.55 (±0.12) | 5.72 (±1.0) |
| 6 | 3.26 (±0.32) | 20.5 (±7.52) | 1.04 (±0.31) | 3.99 (±0.41) | 11.09 (±2.93) |
| 10 | 4.95 (±0.58) | 38.0 (±7.99) | 0.60 (±0.09) | 3.85 (±0.31) | 11.67 (±1.36) |
| 15 | 7.54 (±0.27) | 58.74 (±4.82) | 0.39 (±0.03) | 2.52 (±0.67) | 10.87 (±0.36) |

7. Apply electrical stimulation to the subject using the stimulating parameters described herein to temporarily and selectively block painful sensations without eliciting non-targeted motor and sensory activity.

Experimental Results

The present embodiment may be better understood by reference to the following examples.

Example #1

Figure 27:
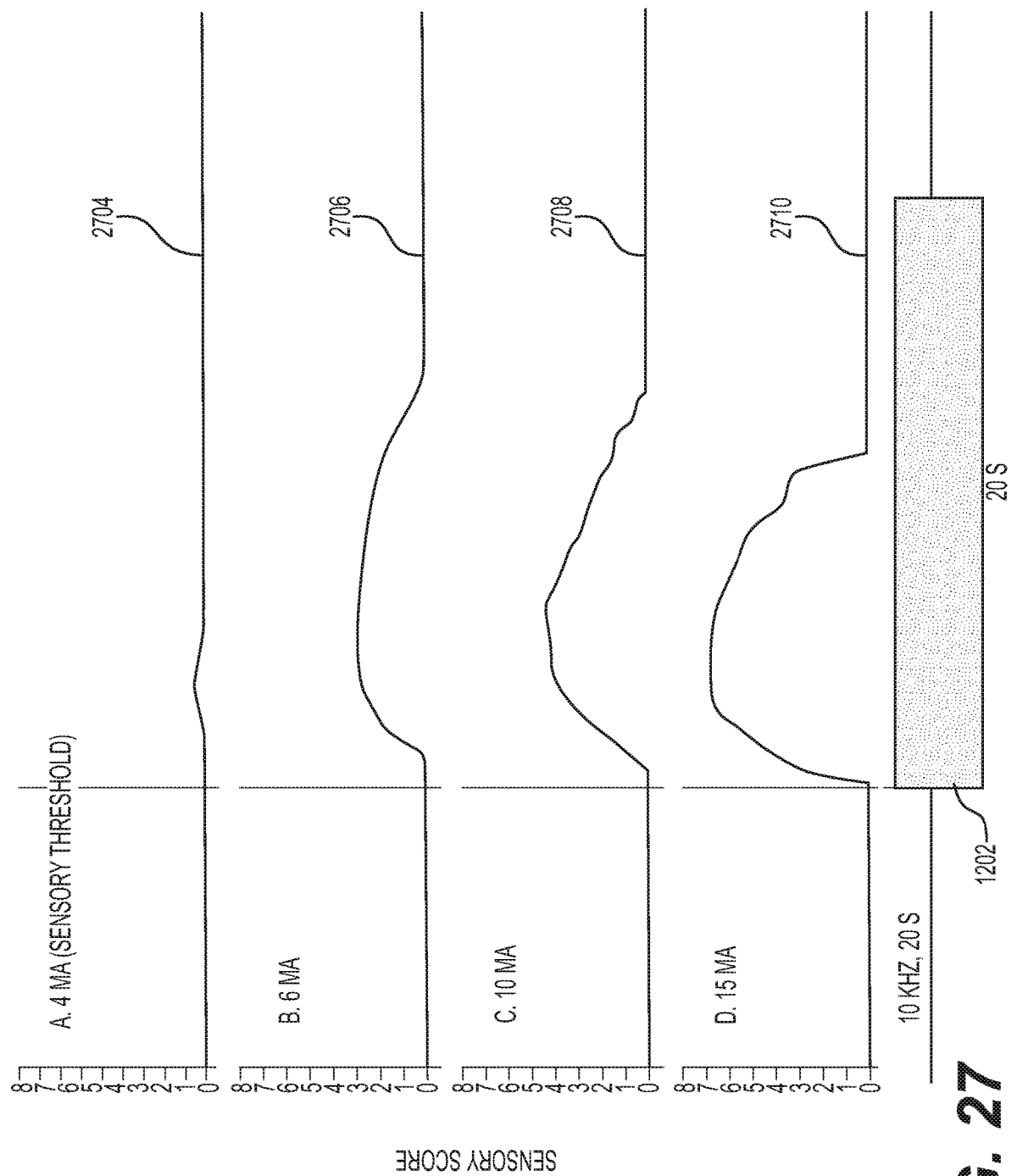
FIG. 27 is a diagram of experimental results illustrating a sensory response to a sinusoidal waveform delivered percutaneously to the saphenous nerve at various current amplitudes.

FIG. 27 demonstrates the sensory response in an able-bodied subject to a percutaneously delivered high-frequency electrical stimulation. The sensations are consistent with the onset response elicited by high-frequency stimulation of a sensory nerve. An S8 (Abbott) electrode was used to stimulate the saphenous nerve at a site 5-to-10 cm proximal to the ankle. The stimulation consisted of a constant-current, 10 kHz sinusoidal waveform, and it was delivered for a period of 20 seconds at various amplitudes, including 4 mA (A—see reference number 2704), 6 mA (B—see reference number 2706), 10 mA (C—see reference number 2708), and 15 mA (D—see reference number 2710). The subject verbally described the quality of the evoked sensations (e.g. light-touch or pain) and indicated the intensity of the sensation on an 11-point scale: levels 1 and 2 defined tactile sensation, level 3 defined the pain threshold, and levels 4-10 indicated a mild-to-severe painful sensation.

FIG. 27, it was observed that high-frequency stimulation delivered at 4 mA elicited a barely perceptible sensation (i.e.

Table 1 shows the average sensory response to 20 seconds of 10 kHz percutaneous electrical stimulation at varying current amplitudes (n=3, ±standard deviation).

As shown in Table 1, at a 4-mA stimulation intensity, the peak sensation ranking was 0.35 on the 11-point scale, and the subject described the sensory response as a vibration that fades. Further, it took an onset time of 1.82 seconds for the subject to indicate a sensory response was felt and took only 5.72 seconds of offset time for the subject to indicate the sensory response had ceased, and the latency or amount of time to feel the peak sensory response was 3.55 seconds. Further the response area was 0.64 (mA*s) indicating that the intensity of the sensory response was low.

At a 6-mA stimulation intensity, the peak sensation ranking was 3.26 on the 11-point scale, and the subject described the sensory response as a sensation that increased quickly. Further, it took an onset time of 1.04 seconds for the subject to indicate a sensory response was felt and 11.09 seconds of offset time for the subject to indicate the sensory response had ceased, and the latency or amount of time to feel the peak sensory response was 3.99 seconds. Further the response area was 20.5 mA*s, indicating that the intensity of the sensory response was increased compared to the 4-mA stimulation.

At a 10-mA stimulation intensity, the peak sensation ranking was 4.95 on the 11-point scale, and the subject described the sensory response as sharp at the beginning, although after some time the sharpness went away along with any other sensation. Further, it took an onset time of 0.60 seconds for the subject to indicate a sensory response was felt and took 11.67 seconds of offset time for the subject to indicate the sensory response had ceased, and the latency or amount of time to feel the peak sensory response was 3.85 seconds. Further the response area was 38 mA*s indicating that the intensity of the sensory response increased compared to both the 4-mA and 6-mA stimulation.

At a 15-mA stimulation intensity, the peak sensation ranking was 7.54 on the 11-point scale, and the subject described the sensory response as painful at the beginning but also indicated that the pain went away quickly. Further, it took an onset time of 0.39 seconds for the subject to indicate a sensory response was felt and took 10.87 seconds of offset time for the subject to indicated the sensory response had ceased, and the latency or amount of time to feel the peak sensory response was only 2.52 seconds. Further the response area was 58.74 mA*s, indicating that the intensity of the sensory response was increased compared to the 4 mA, 6 mA, and 10 mA stimulations.

Further, the 6-mA stimulation was determined to be the stimulation intensity at which the pain threshold was reached, where the pain threshold was also associated with a peak sensation/sensory score of greater than or equal to 3. Example #1 also indicated that as the stimulation intensity was increased, the sensory score increased, the sensory response area increased, and the onset latency decreased.

In addition, although the 15-mA stimulation was considered painful initially, it was determined that the 15-mA stimulation was successful at nerve blocking after the initial painful onset response, as indicated by the fact that the pain quickly went away. As such Example #2 was carried out to focus on minimizing the onset response at the 15-mA stimulation intensity, as discussed in more detail below.

Example #2

To determine if the onset response experienced when a 15-mA stimulation was delivered to the saphenous nerve could be minimized or eliminated, various ramping conditions were tested where the amplitude was allowed to gradually increase to the 15-mA level rather than being immediately set to 15-mA, after which time the 15-mA stimulation was delivered for a time period of 20 seconds. Specifically, the data from the 15-mA stimulation from Example #1 where no ramping was utilized was compared to two different ramping rates—(1) 1 milliamp/second and (2) 0.5 milliamps/second.

Figure 28A:
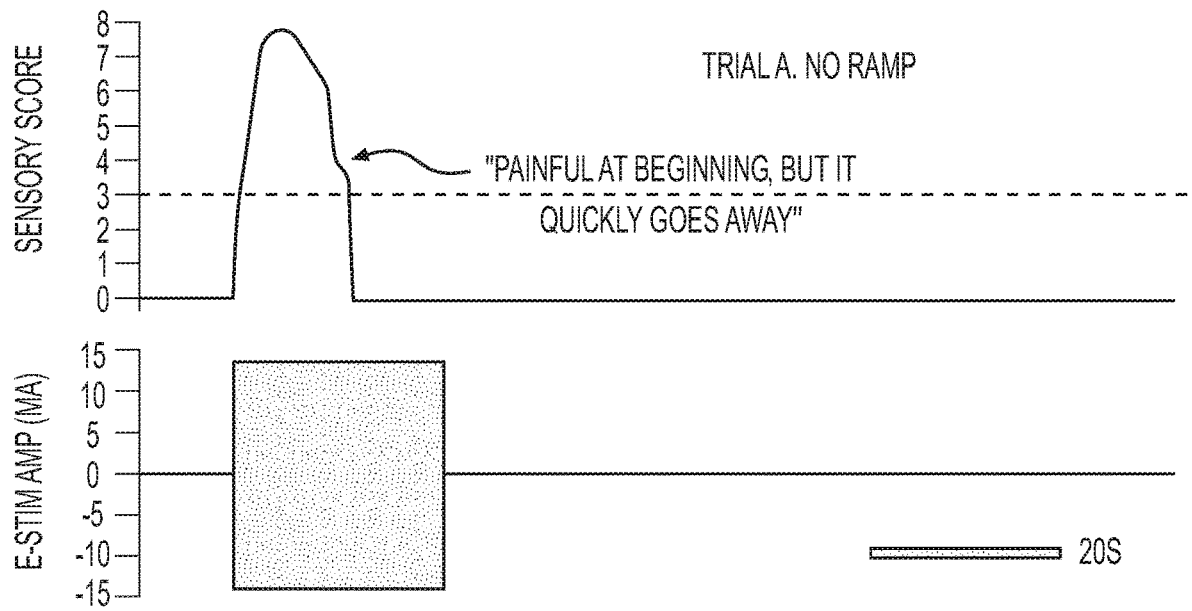
FIG. 28A is a diagram of experimental results illustrating a baseline sensory response to a sinusoidal waveform delivered percutaneously to the saphenous nerve.
Figure 28B:
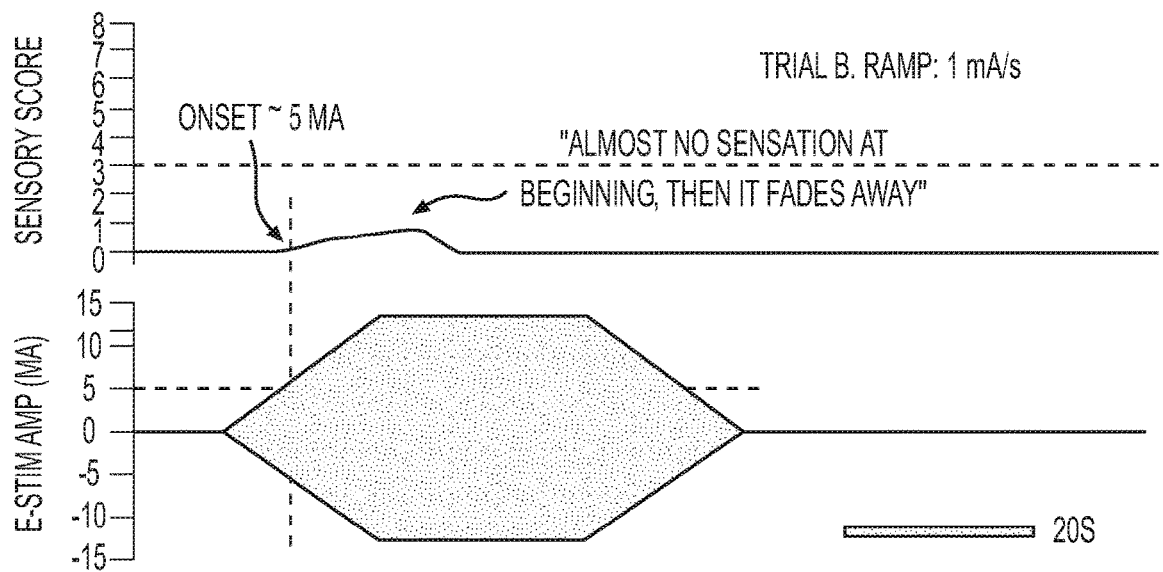
FIGS. 28B and 28C are diagrams of experimental results illustrating sensory responses to a sinusoidal waveform delivered percutaneously to the saphenous nerve where the waveform was adjusted at various a ramp rates.
Figure 28C:
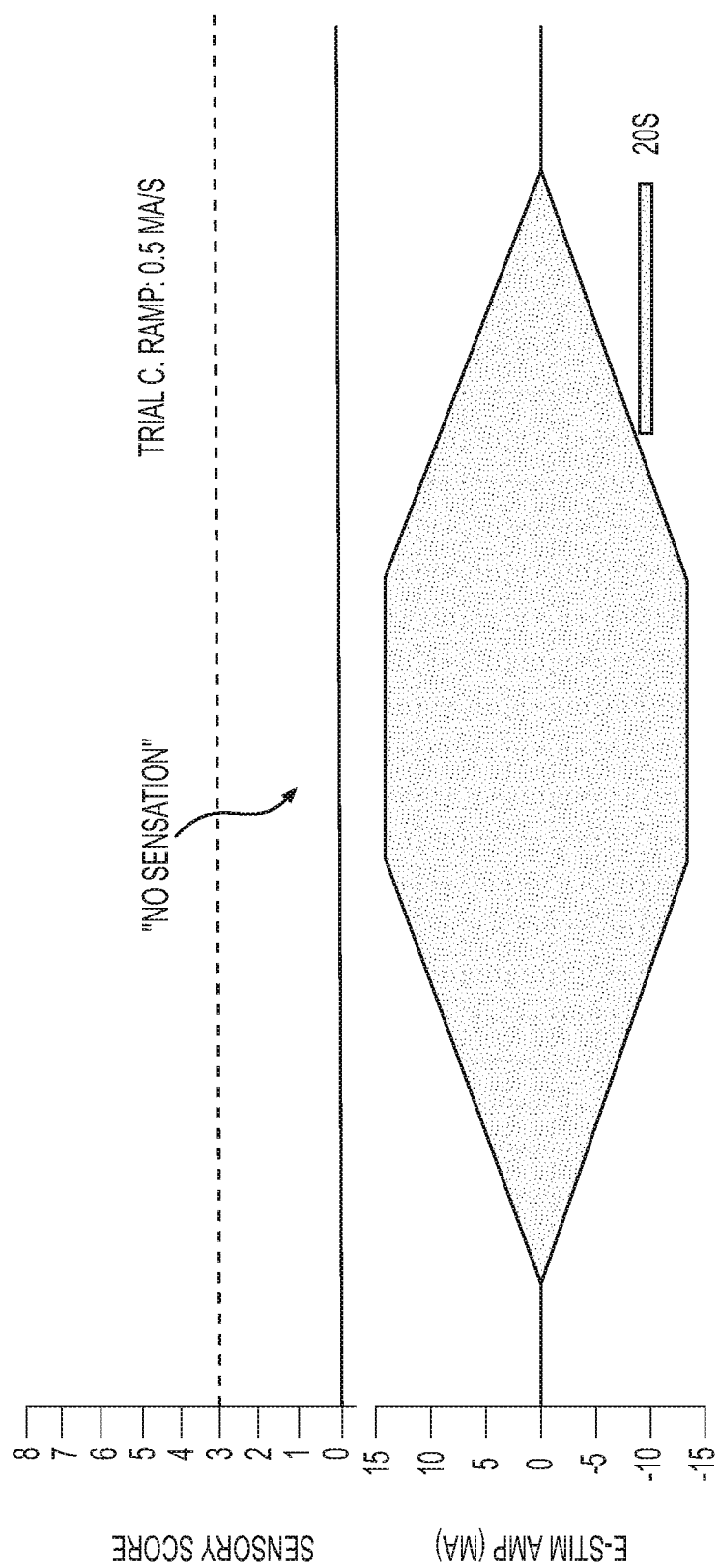

The results are shown in FIGS. 28A-28C and Table 2 below.

took 10.87 seconds of offset time for the subject to indicated the sensory response had ceased, and the latency or amount of time to feel the peak sensory response was only 2.52 seconds. Further the response area was 58.74 mA*s.

FIG. 28B shows results to an electrical stimulation in which a ramp rate of 1 milliamp per second was utilized to gradually increase the electrical stimulation to a desired 15-mA stimulation intensity was reached. As observed in FIG. 28B, the peak sensation ranking was reduced significantly to 0.81 on the 11-point scale, and the subject described the sensory response as feeling almost no sensation at the beginning, where the sensation quickly faded away. The sensory response was first felt when the amplitude reached about 5.3 mA. Further, it took an onset time of 5.89 seconds for the subject to indicate a sensory response was felt and took 20.67 seconds of offset time for the subject to indicate the sensory response had ceased, and the latency or amount of time to feel the peak sensory response was increased to 16.56 seconds. Further the response area was 7.08 mA*s.

FIG. 28C shows results to an electrical stimulation in which a ramp rate of 0.5 milliamps per second was utilized to gradually increase the electrical stimulation the until a desired 15-mA stimulation intensity was reached. It was observed that the peak sensation ranking was 0 on the 0 to 11 scale, and the subject described feeling no sensation at all for the sensory response, indicating that the presence of an offset response was completely eliminated. The sensory response was first felt when the amplitude reached about 5.3 mA. As such, all of the measured values are 0.

Indeed, it was observed that ramping the electrical stimulation gradually to a desired or pre-defined stimulation intensity or amplitude provided a peak sensation/sensory response level that is less than the baseline (same stimulation but without ramping); the response area is less than the baseline, the time to reach the onset response took longer than the baseline, the peak latency time took longer than the baseline; and the offset time took longer than the baseline.

Example #3

The following results shows the ability to block acute pain sensations with high-frequency electrical stimulation delivered in a percutaneous fashion.

Figure 29A:
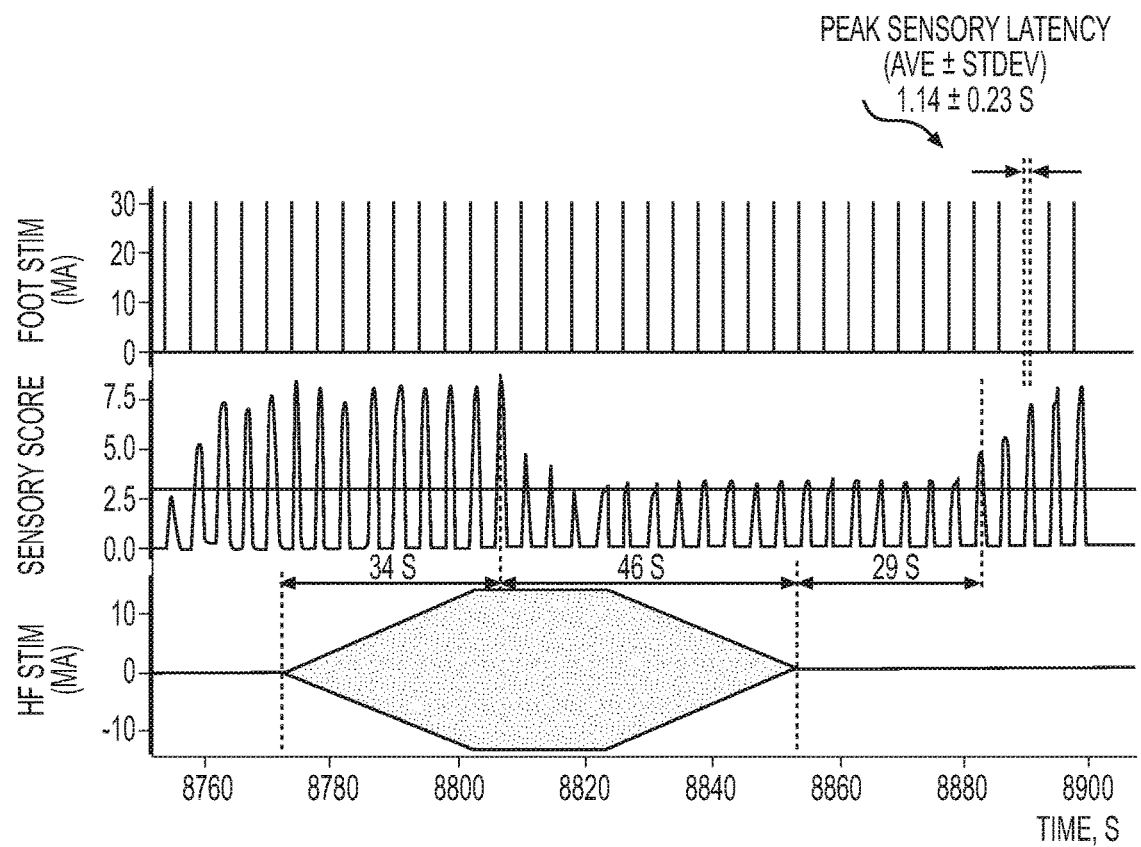
FIGS. 29A and 29B are diagrams of experimental results illustrating sensory responses to a sinusoidal waveform at various levels delivered percutaneously to the saphenous nerve, while pain inducing electrical stimulation was concurrently applied to the subject.
Figure 29B:
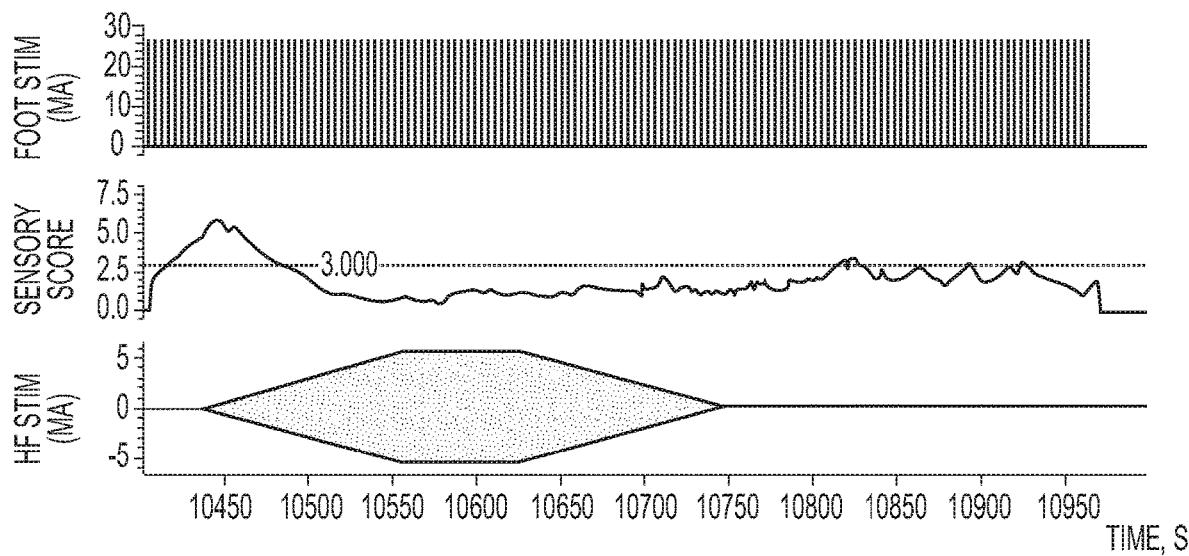

FIGS. 29A and 29B are diagrams of experimental results illustrating sensory responses to a sinusoidal waveform at various levels delivered percutaneously to the saphenous

TABLE 2

| Amplitude (mA) | Peak Sensation (0 to 8 Scale) | Response Area (mA*s) | Onset (seconds) | Peak Latency (seconds) | Offset (seconds) | Onset-Amp (mA) |
|---|---|---|---|---|---|---|
| 15 (no ramp) | 7.54 (±0.27) | 58.74 (±4.82) | 0.39 (±0.03) | 2.52 (±0.67) | 10.87 (±0.36) | NA |
| 15 (1 mA/s ramp) | 0.81 (±0.02) | 7.08 (±0.94) | 5.89 (±0.38) | 16.56 (±2.35) | 20.67 (±1.78) | 5.3 (±0.26) |
| 15 (0.5 mA/s ramp) | N/A | N/A | N/A | N/A | N/A | N/A |

Table 2 shows an average sensory response to a 20-seconds 10 kHz percutaneous electrical stimulation at 15-milliamps current amplitude (n=3, ±standard deviation).

In FIG. 28A, the no-ramp condition from Example #1 is reproduced, in which a high-frequency stimulation was delivered at a 15-mA stimulation intensity. As noted above, the observed peak sensation ranking was 7.54 on a 11-point scale, and the subject described the sensory response as painful at the beginning but also indicated that the pain went away quickly. Further, it took an onset time of 0.39 seconds for the subject to indicate a sensory response was felt and nerve, while pain inducing electrical stimulation was concurrently applied to the subject. Specifically, FIGS. 29A and 29B demonstrate the effect of high-frequency electrical stimulation in blocking acute pain sensations in 2 able-bodied subjects. In the experiment corresponding to FIG. 29A, a pain eliciting electrical stimulation (9 pulses train, 500 Hz, 1 millisecond pulse width, about 30 mA amplitude, inter-train interval of 4 seconds) was delivered to the subject's foot over-top of the saphenous nerve to elicit painful sensations to simulate/cause acute pain. Then, and as shown in FIG. 29A, a high-frequency (10 kHz) electrical stimulation was percutaneously delivered to the saphenous nerve at a site proximal to the ankle, and with a ramp rate of 0.5 mA/s, and a 15 mA plateau lasting 20 seconds. It was observed that, prior to application of the high-frequency stimulation to block the pain, the subject indicated a sensory score of about 7.5. As high-frequency stimulation was applied, the subject indicated a reduced score of about 3 (which is at the boundary of the pain threshold). In the experiment, the amplitude of the high-frequency electrical stimulation to block acute pain sensations was about 4 times the subject's sensory threshold (4 mA). Moreover, it was observed that the reduction in sensory score continued after termination of the high-frequency stimulation and lasted about 29 s.

In FIG. 29B, a pain-eliciting electrical stimulation (9 pulses train, 500 Hz, 1 millisecond pulse width, about 28 mA amplitude, inter-train interval of 4 seconds) was again delivered to the subject's foot over-top of the saphenous nerve to elicit painful sensations to simulate/cause acute pain. Then, and as shown in FIG. 29B, a high-frequency electrical stimulation was percutaneously delivered to the saphenous nerve at a site proximal to the ankle, and with a ramp rate of 0.05 mA/s, and a 5.5 mA plateau lasting 91 seconds. It was observed that, prior to application of the high-frequency stimulation to block the pain, the subjective sensory score was recorded with a maximum level of about 6 and, and during application of the high-frequency stimulation, a minimum level of about 1 was observed. Here, the amplitude of the high-frequency electrical stimulation was again approximately 4 times the sensory-threshold, or 1.3 mA. It was observed that the reduction in sensory score continued after termination of the high-frequency stimulation and for the duration of the trial that was about 270 seconds. Incidentally, the subject's sensory score recovered to 7.5 after a few minutes of rest and prior to the following trial.

Indeed, in the tested subjects, lower ramping rates were observed to provide longer lasting and more pronounced reduction in elicited painful sensations at the foot.

Example #4

Figure 30:
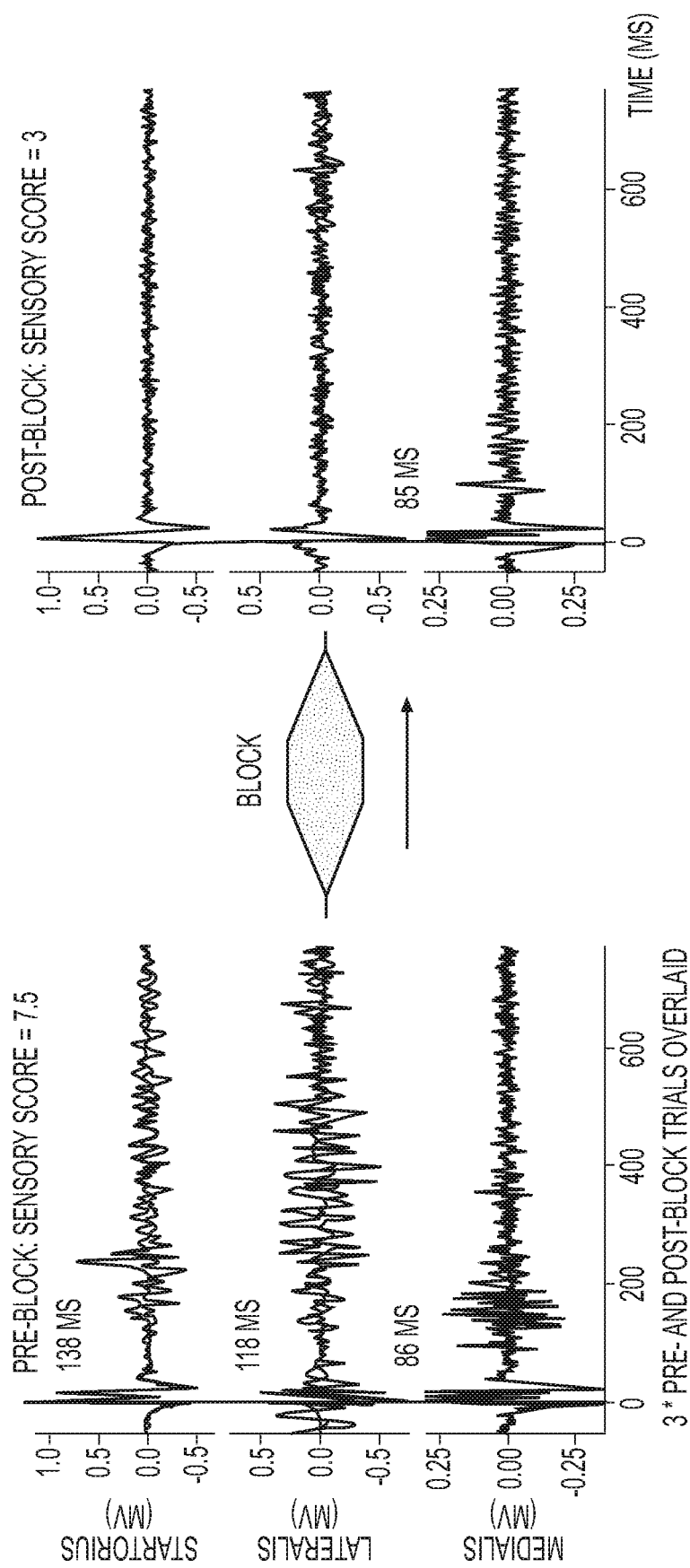

FIG. 30 further demonstrates results of percutaneous high-frequency electrical stimulation in blocking the nociceptive reflex. Electromyogram (EMG) signals were recorded from the vastus medialis, vastus lateralis and sartorius muscles in response to painful electrical stimulation that is delivered to the foot over-top of the saphenous nerve to simulate/cause acute pain. The resultant bursts of EMG, hosted by the nociceptive reflex, are considered a quantitative method for assessing pain in humans. The plots on the left side and right side of FIG. 30 show stimulus-elicited bursts of EMG before and after high-frequency electrical stimulation (10 kHz) were delivered percutaneously to the saphenous nerve at a site proximal to the ankle. Three overdrawn trials represent each data trace. Prior to high-frequency electrical stimulation, the nociceptive reflexes were elicited in all 3 muscles tested (left side plot) with latencies ranging from 85 to 160 ms. Stimulus-elicited bursts of EMG were largely absent immediately following the stimulation (right side plot). The average sensory score reported by the subject during the time periods describing EMG activity decreased from 7.5 to 3 (pain-threshold). Indeed, the measured data suggested that the mechanisms responsible for reductions in pain sensation may be attributed to nerve block, and not by higher-order processes.

Example #5

Figure 31:
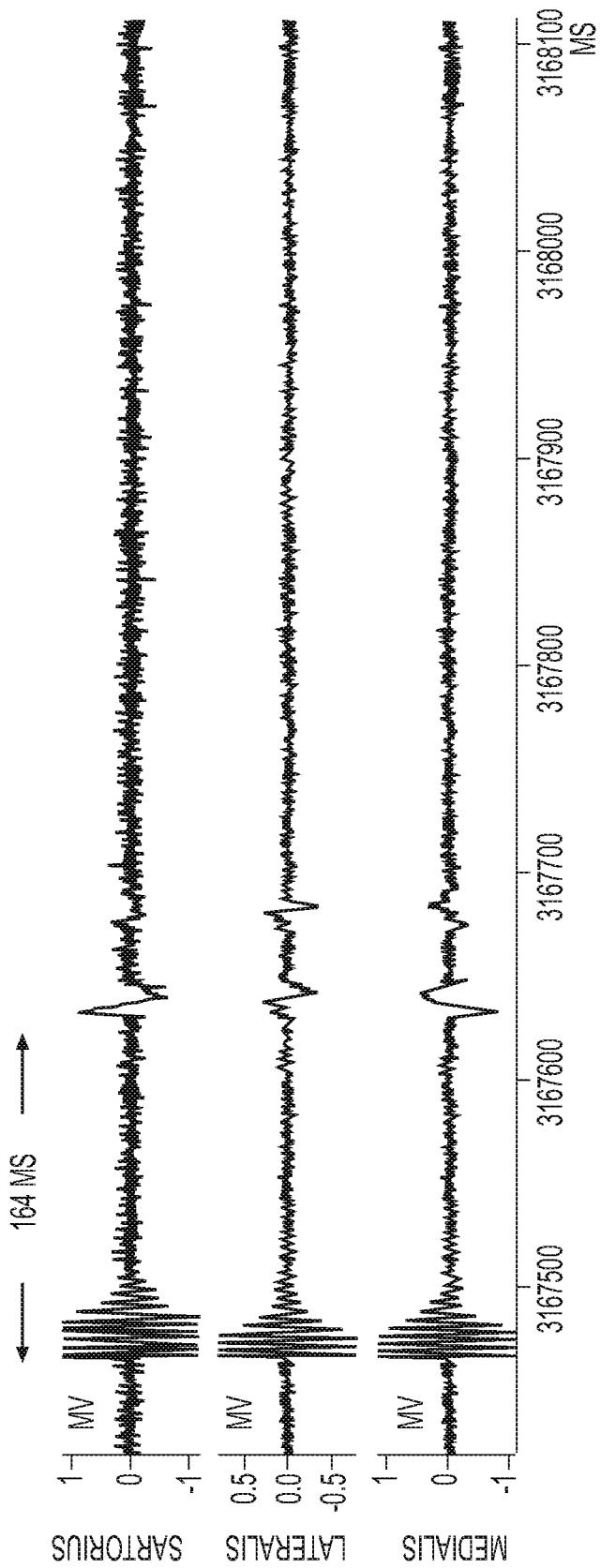
FIG. 31 is diagram of experimental results illustrating bursts of EMG activity elicited by short-pulses of high-frequency electrical stimulation (10 cycles, 10 kHz sine wave) to establish that placement of an electrode in the lumen of the intermuscular septum may provide a large window of electrical current that can be used to block saphenous nerve activity without causing co-excitation of nearby tissue.

FIG. 31 is diagram of experimental results illustrating bursts of EMG activity elicited by short-pulses of high-frequency electrical stimulation (10 cycles, 10 kHz sine wave) to establish that placement of an electrode in the lumen of the intermuscular septum may provide a large window of electrical current that can be used to block saphenous nerve activity without causing co-excitation of nearby tissue. Specifically, FIG. 31 show that the muscle activity elicited by short-bursts of high-frequency stimulation delivered to the intermuscular septum in the adductor canal is hosted by spinal reflexes and are not due to volume conduction or "co-excitation" of nearby muscle. To produce the results of FIG. 31, bursts of EMG activity were elicited by short-pulses of high-frequency electrical stimulation (10 cycles, 10 kHz sinewave). The stimulation was percutaneously delivered to the lumen of the intermuscular septum in the adductor canal via a cylindrical electrode (Model: Octrode; Abbott) operated in a monopolar fashion. Electromyogram (EMG) activity was recorded from the vastus medialis, vastus lateralis and sartorius muscles. Bursts of EMG were elicited with a minimum stimulation intensity of 25 mA (i.e., motor-threshold). Moreover, the bursts occurred about 164 ms post-stimulation. These data The exemplary method further established that placement of an electrode in the lumen of the intermuscular septum may provide a large window of electrical current that can be used to block saphenous nerve activity without causing co-excitation of nearby tissue.

Example #6

Figure 32A:
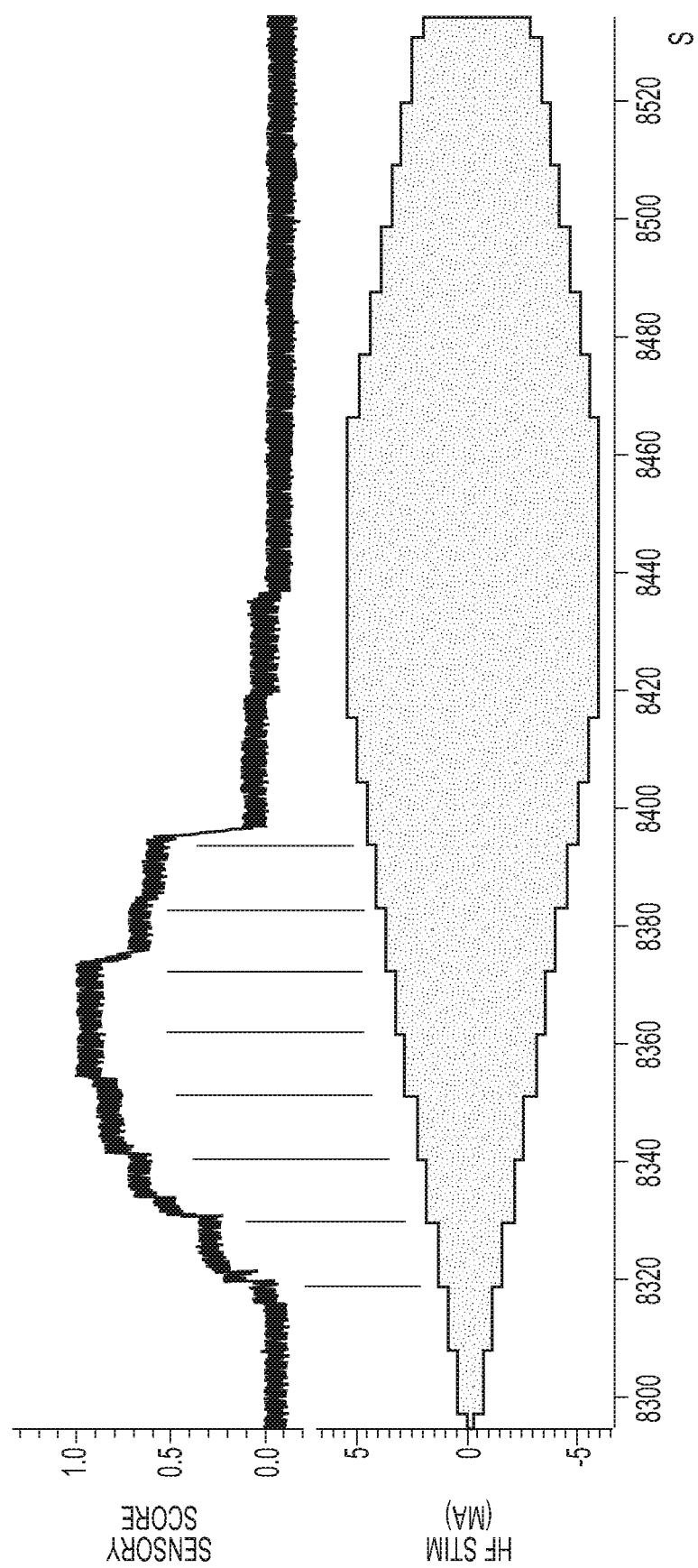
FIG. 32A is a diagram of experimental results illustrating the effect of discontinuity in a high frequency electrical stimulation waveform delivered to the saphenous nerve in an able-bodied subject.
Figure 32B:
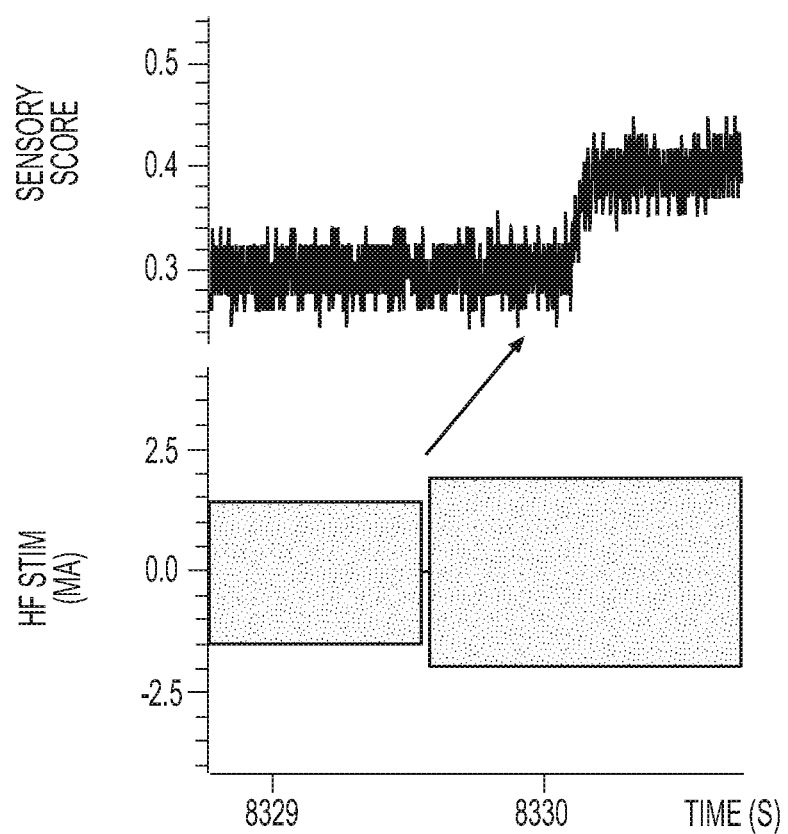
FIG. 32B is a zoomed-in view of the graph of FIG. 32A.
Figure 32C:
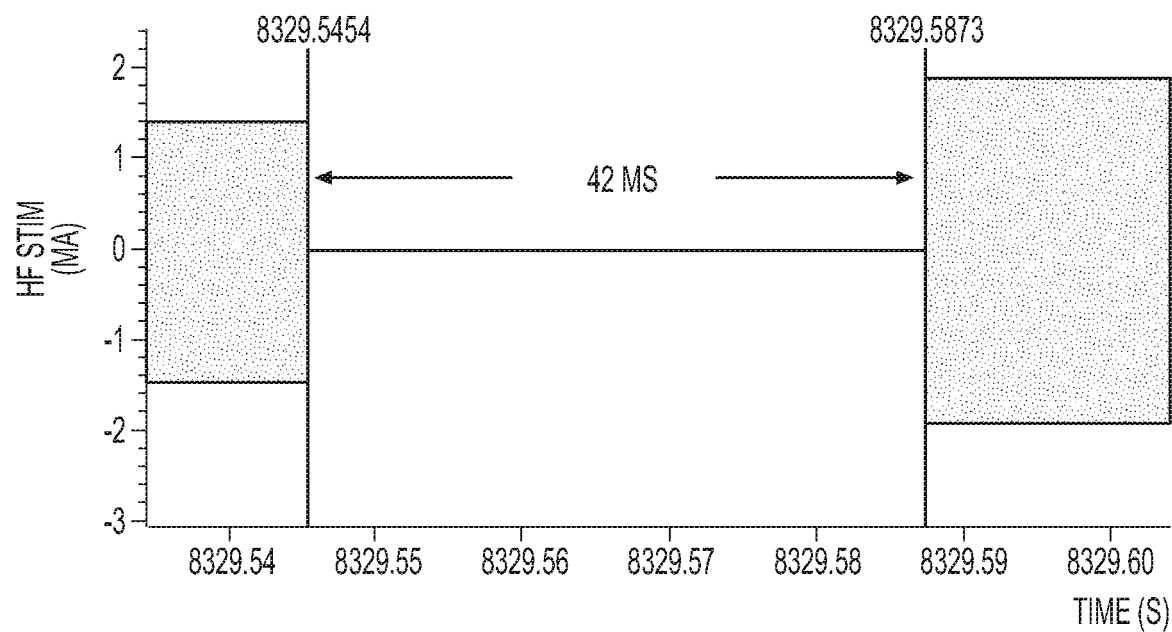
FIG. 32C is a zoomed-in view of the graph of FIG. 32B.

FIGS. 32A, 32B, and 32C demonstrate the effects of discontinuity in the application of a high-frequency electrical stimulation waveform being delivered to the saphenous nerve in an able-bodied subject. Indeed, as shown in FIG. 32A, discontinuity in waveform amplitude and time were reliably detected by the subject as indicated by abrupt changes in sensory score. FIG. 32B shows a zoomed version of the results of FIG. 32A, and FIG. 32C shows a further zoomed version of results of FIG. 32B. In FIG. 32C, it can be observed that the discontinuity in the delivery of the waveform lasted for about 42 milliseconds (ms). Indeed, a system and method that avoids such discontinuity (e.g., transient periods of discontinuity) is contemplated by the present embodiments.

The embodiments described above are intended to be exemplary only. The scope of the embodiment is therefore intended to be limited solely by the scope of the appended claims.

It is appreciated that certain features of the embodiment, which are, for clarity, described in the context of separate embodiments, may also be provided in combination in a single embodiment. Conversely, various features of the embodiment, which are, for brevity, described in the context of a single embodiment, may also be provided separately or in any suitable subcombination.

Although the embodiment has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present embodiment.

What is claimed is:

1. A method of operating a placement assembly to place a percutaneous lead into a treatment site of a subject to block nerve conduction, the method comprising:
   positioning a placement assembly into the treatment site;
   applying an electrical stimulation via the placement assembly to stimulate a target peripheral nerve and confirming placement of the placement assembly bar monitoring motor or sensory feedback; and
   percutaneously inserting a percutaneous lead through an entry port of the placement assembly, including:
      inserting the percutaneous lead at a first angle of insertion defined with respect to an associated surface of the treatment site, and wherein the first angle of insertion is between 10 degrees and 90 degrees,
      directing, via the placement assembly, the percutaneous lead to exit the placement assembly at a second angle that is parallel, or substantially parallel, to a long axis of the peripheral nerve and placing one or more electrodes of the percutaneous lead over an overlapping nerve region of the peripheral nerve so that the one or more electrodes cover at least 3 mm of the overlapping nerve region, and
      advancing the percutaneous lead so that the percutaneous lead exits and extends beyond the placement assembly and a leading point of the percutaneous lead penetrates through at least 1 cm of the tissue proximal to, and without contacting, the peripheral nerve, and so as to place the one or more electrodes at a predetermined distance away from one side of the long axis of the peripheral nerve; and
   blocking nerve conduction through the overlapping nerve region by applying an electrical field having a primary frequency harmonic between 1.5 kHz and 100 kHz between the one or more electrodes and the overlapping nerve region, thus preventing an action potential from forming at the overlapping nerve region.

2. The method of claim 1, further comprising:
   percutaneously placing the placing assembly into the treatment site, wherein during the placing a tip comprising an exit port of the placing assembly is placed at a pre-defined distance or pre-defined orientation from the peripheral nerve.

3. The method of claim 2, wherein the placement assembly establishes a path for insertion of the percutaneous lead into tissue to put the one or more electrodes in parallel, or substantially parallel, to the long axis of the peripheral nerve.

4. The method of claim 1, further comprising:
   percutaneously placing the placement assembly into the treatment site, wherein the placement assembly includes a fixed curve or includes a flexible region configured to be bent to direct the percutaneous lead from the first angle to the second angle.

5. The method of claim 1, further comprising:
   percutaneously placing a second placement assembly comprising a needle or introducer into the treatment site; and
   placing the placement assembly comprising a sheath through, or around, the second placement assembly, wherein retraction of the second placement assembly directs the placement assembly into a pre-defined angle configured to direct the percutaneous lead from the first angle to the second angle.

6. The method of claim 5, wherein the placement assembly is engaged to the second placement assembly, and wherein the placement assembly and second placement assembly are engaged to the second placement assembly.

7. The method of claim 1, further comprising:
   locking via a member of the percutaneous lead with the placement assembly, wherein the percutaneous lead is advanced with the placement assembly when the member is engaged.

8. The method of claim 1, wherein the percutaneous lead comprises a stylet inserted into a lumen of the percutaneous lead, the method further comprising:
   removing the stylet once the one or more electrodes of the percutaneous lead are placed over the overlapping nerve region.

9. The method of claim 1, comprising:
   receiving a portion of the percutaneous lead having a predominantly non-circular cross-section.

10. The method of claim 1, comprising:
    receiving a portion of the percutaneous lead having a circular cross-section, or near circular cross-section.

11. The method of claim 1, wherein the placing of the percutaneous lead into the treatment site is guided by an imaging system.

12. The method of claim 1, wherein the placing of the percutaneous lead into the treatment site is performed without prior incisions at the treatment site.

* * * * *

UNITED STATES PATENT AND TRADEMARK OFFICE
CERTIFICATE OF CORRECTION

PATENT NO. : 11,305,115 B2
APPLICATION NO. : 16/355670
DATED : April 19, 2022
INVENTOR(S) : Ryan Caldwell et al.

Page 1 of 1

It is certified that error appears in the above-identified patent and that said Letters Patent is hereby corrected as shown below:

In the Claims

In Column 57, Line 17 of Claim 1, the text --confirming placement of the placement assembly bar-- should be --confirming placement of the placement assembly by--

Signed and Sealed this
Second Day of August, 2022

Katherine Kelly Vidal
*Director of the United States Patent and Trademark Office*